United States Patent
O'Brien et al.

(10) Patent No.: US 11,439,696 B2
(45) Date of Patent: Sep. 13, 2022

(54) MODULATION OF PROPROTEIN CONVERTASE SUBTILISIN/KEXIN 9 EXPRESSION (PCSK9) WITH HSP 27 AND/OR HSP25

(71) Applicant: PEMI31 Therapeutics Inc., Calgary (CA)

(72) Inventors: Edward R. M. O'Brien, Calgary (CA); Chunhua Shi, Pearland, TX (US); Yong-Xiang Chen, Calgary (CA)

(73) Assignee: PEMI31 THERAPEUTICS INC., Calgary (CA)

( * ) Notice: Subject to any disclaimer, the term of this patent is extended or adjusted under 35 U.S.C. 154(b) by 211 days.

(21) Appl. No.: 15/756,282

(22) PCT Filed: Aug. 29, 2016

(86) PCT No.: PCT/CA2016/051018
§ 371 (c)(1),
(2) Date: Feb. 28, 2018

(87) PCT Pub. No.: WO2017/035641
PCT Pub. Date: Mar. 9, 2017

(65) Prior Publication Data
US 2018/0280486 A1    Oct. 4, 2018

Related U.S. Application Data

(60) Provisional application No. 62/211,190, filed on Aug. 28, 2015.

(51) Int. Cl.
| | | |
|---|---|---|
| *A61K 39/00* | (2006.01) | |
| *A61K 39/395* | (2006.01) | |
| *C07K 16/18* | (2006.01) | |
| *G01N 33/543* | (2006.01) | |
| *A61K 39/39* | (2006.01) | |
| *C07K 14/47* | (2006.01) | |
| *A61K 38/17* | (2006.01) | |
| *C12N 9/58* | (2006.01) | |
| *A61P 3/06* | (2006.01) | |

(52) U.S. Cl.
CPC ...... *A61K 39/0005* (2013.01); *A61K 38/1709* (2013.01); *A61K 39/39* (2013.01); *A61K 39/3955* (2013.01); *A61P 3/06* (2018.01); *C07K 14/47* (2013.01); *C07K 14/4703* (2013.01); *C07K 16/18* (2013.01); *C12N 9/58* (2013.01); *G01N 33/54326* (2013.01); *A61K 39/395* (2013.01); *A61K 2039/55505* (2013.01); *A61K 2039/55566* (2013.01); *G01N 2333/4703* (2013.01)

(58) Field of Classification Search
None
See application file for complete search history.

(56) References Cited

U.S. PATENT DOCUMENTS

2011/0124568 A1    5/2011 O'Brien et al.

FOREIGN PATENT DOCUMENTS

WO        WO0145738 A2    6/2001

OTHER PUBLICATIONS

Wax et al. (The Journal of Neuroscience, 2008, 28:12085-12096).*
Billiau et al. (Journal of Leukocyte Biology, 2001, 70:849-860).*
Attwood (Science 2000 290:471-473).*
Skolnick et al. (Trends in Biotech. 2000, 18:34-39).*
O'Brien, E. et al., "Novel Reduction of PCSK9 Expression: Mechanistic Insights into the Anti-Atherosclerotic & Hypolipidemic Effects of Heat Shock Protein 27", Aug. 29, 2015. Retrieved from the Internet: URL: https://www.ucalgary.ca/obrien/files/obrien/obrien_esc15_hot-line_pcsk9.pdf [retrieved on Mar. 18, 2019[.
O'Brien et al. "Novel reduction of PCSK9 expression: mechanistic insights into the anti-atherosclerotic and hypolipidemic effects of HSP27", Abstract, Eur Heart Journal, vol. 36, Issue supp_1, Aug. 2015, ESC Congress 2015, London, United Kingdom, Aug. 29-Sep. 2, 2015.
Raizman, J.E. et al. "Heat shock protein-27 attenuates foam cell formation and atherogenesis by down-regulating scavenger receptor-A expression via NFKB signaling", Biochem Biophys Acta. 2013, 1831 (12):1721-1728.
Seibert, T.A. et al. "Serum Heat shock protein 27 levels represent a potential therapeutic target for atheroscleosis", JACC, 2013, 62(16):1446-1454.
Shi, C. et al. "When auto-antibodies potentiate: The paradoxical signalling role of anti-HSP27 auto-antibody immune complexes improves athero-protection". Circulation, 2014, 130 (Suppl 2): A12771.

* cited by examiner

*Primary Examiner* — Sharon X Wen
(74) *Attorney, Agent, or Firm* — Bereskin & Parr LLP/S.E.N.C.R.L., s.r.l.; Micheline Gravelle

(57) ABSTRACT

The patent application pertains to compositions and methods for reducing Proprotein Convertase Subtilisin/Kexin 9 (PCSK9) expression and for reducing serum cholesterol in mammalian subjects. The exemplary compositions comprise heat0 shock protein HSP27 or fragments thereof and/or a HSP25, or fragments thereof in a mixture with an adjuvant. The compositions may optionally comprise anti-HSP27 antibody. The method for reducing serum cholesterol relate to the use of the compositions to increase the subject's levels of serum HSP27 and/or anti-HSP27 antibodies.

9 Claims, 37 Drawing Sheets
Specification includes a Sequence Listing.

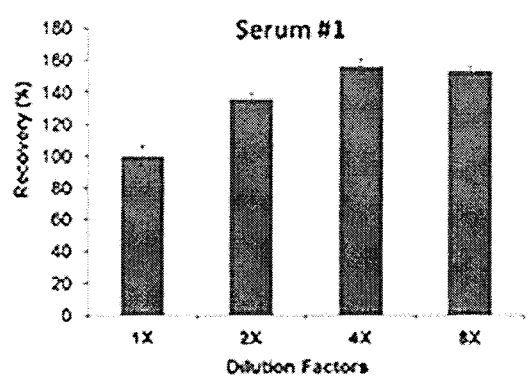
Fig. 2A
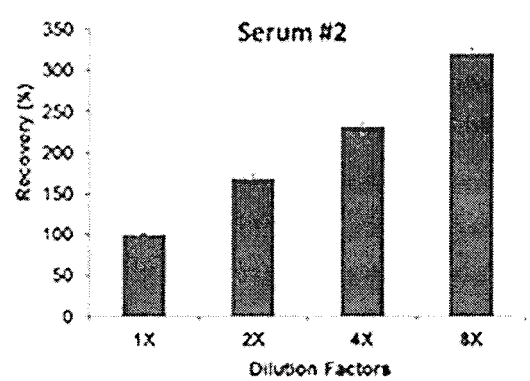
Fig 2B
Fig. 2

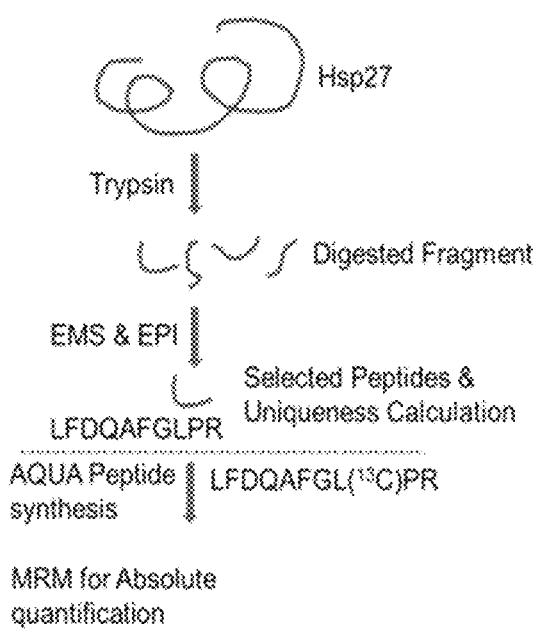 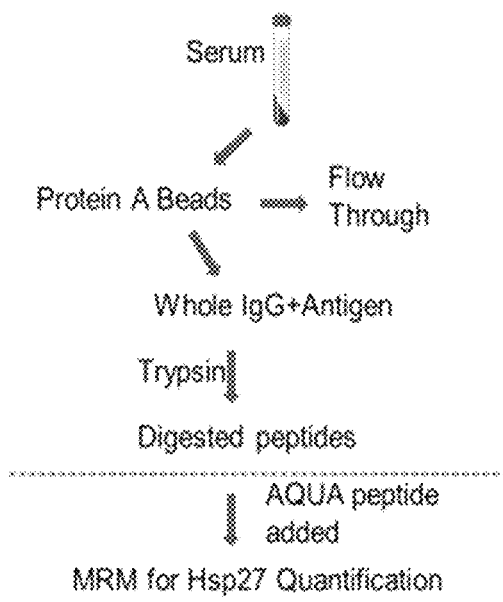
Fig. 3A         Fig. 3B
Fig. 3

Analytic Result:

Uniqueness of Top n transitions

| Transitions | Nr transitions | Combined Uniqueness |
|---|---|---|
| y8 | 1 | No |
| y8 + y5 | 2 | No |
| y8 + y5 + y4 | 3 | Yes |
| y8 + y5 + y4 + y6 | 4 | Yes |

⇐ These transitions combined are unique

Fig. 6

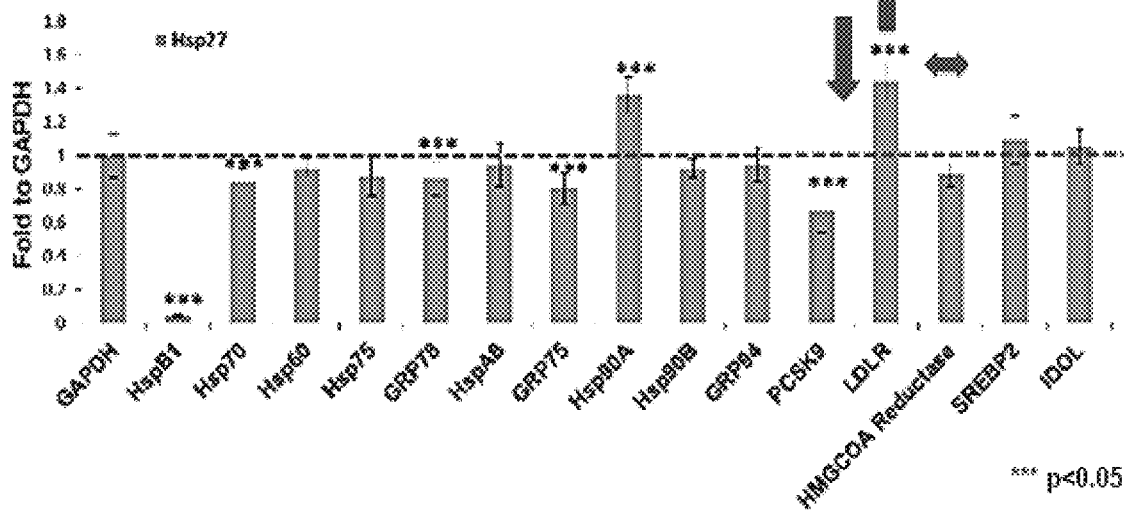
Fig. 9A
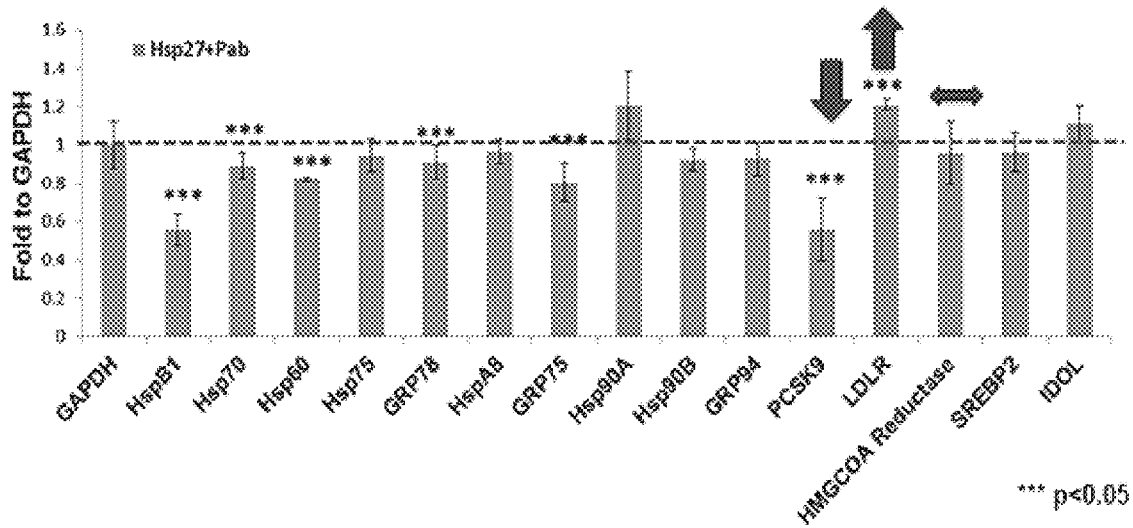
Fig. 9B
Fig. 9

Fig. 10A
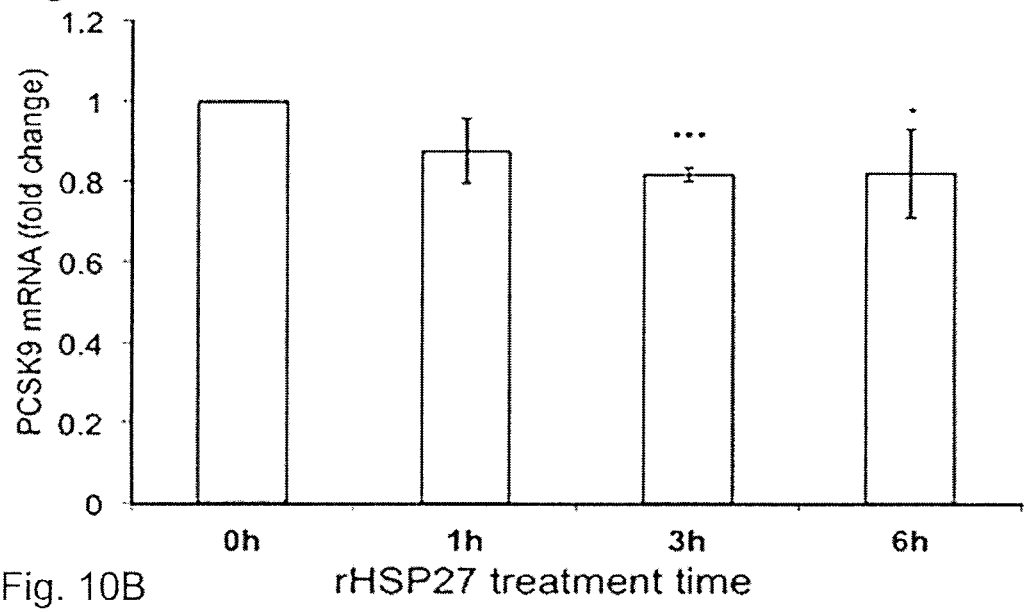
Fig. 10B
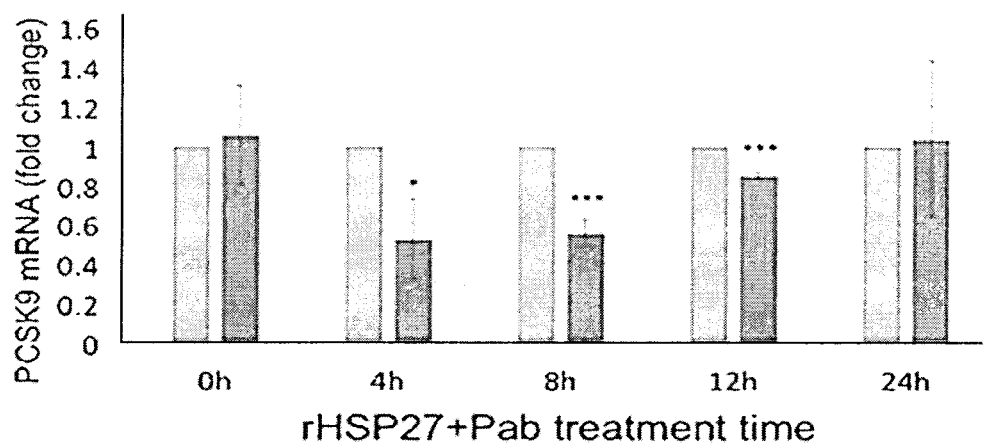
Fig. 10

Fig. 15A
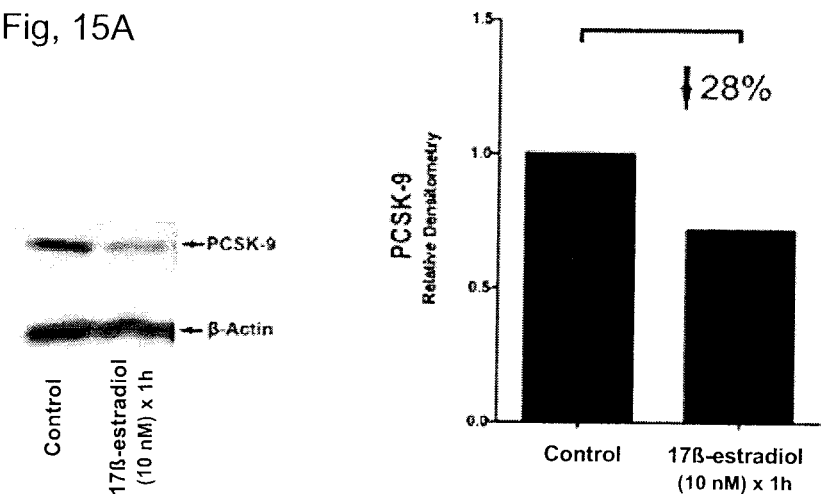
Fig. 15B
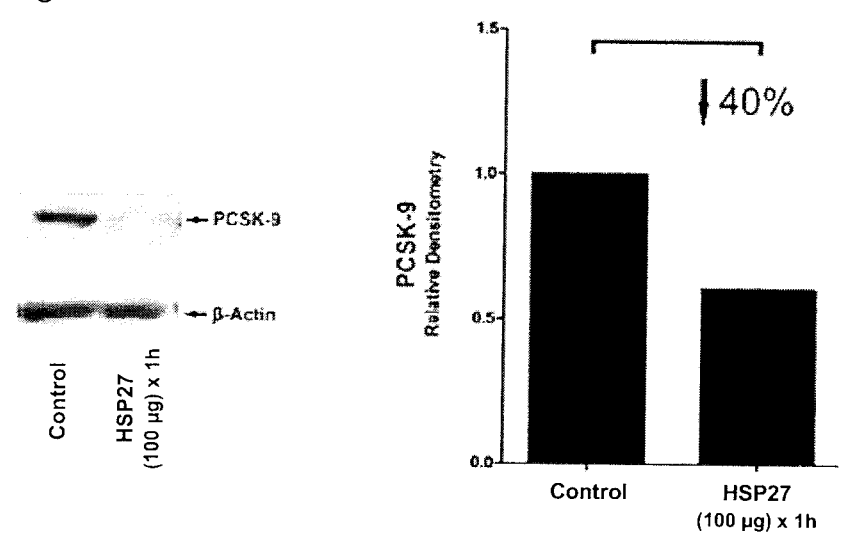
Fig. 15

Fig. 16A
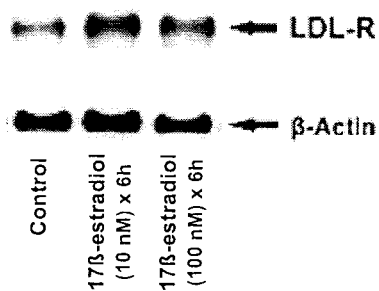
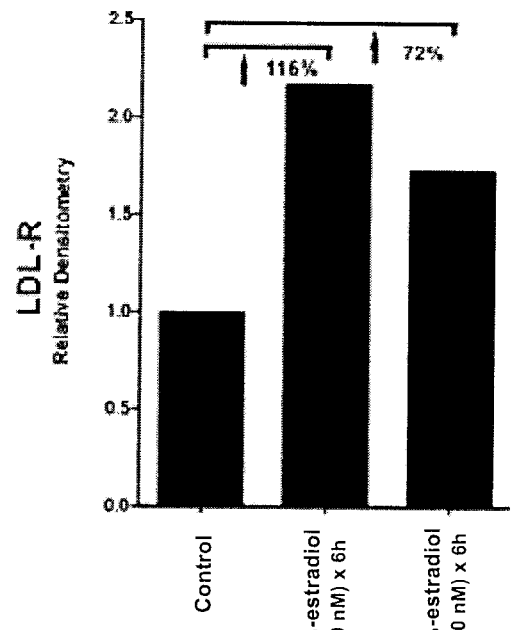
Fig. 16B
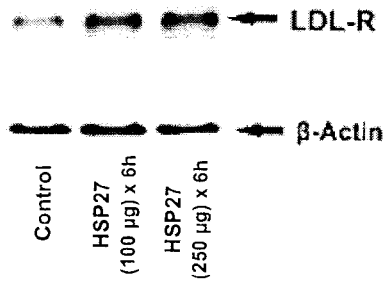
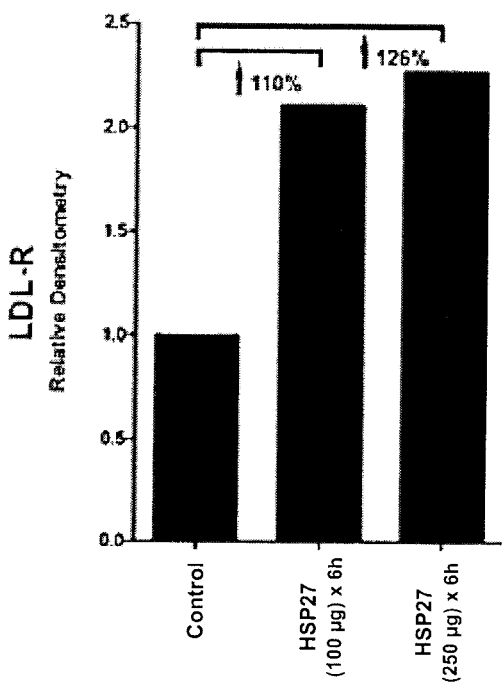
Fig. 16

Fig. 33

000

SEQUENCE LISTING

```
<160> NUMBER OF SEQ ID NOS: 6

<210> SEQ ID NO 1
<211> LENGTH: 678
<212> TYPE: PRT
<213> ORGANISM: Artificial Sequence
<220> FEATURE:
<223> OTHER INFORMATION: Recombinant HSP25 peptide

<400> SEQUENCE: 1

Cys Ala Thr Ala Thr Gly Cys Ala Thr Cys Ala Cys Cys Ala Thr Cys
1               5                   10                  15

Ala Thr Cys Ala Cys Cys Ala Cys Cys Ala Cys Cys Ala Thr Gly Ala
                20                  25                  30

Thr Gly Ala Cys Gly Ala Cys Gly Ala Cys Ala Ala Gly Ala Cys Cys
            35                  40                  45

Gly Ala Gly Cys Gly Cys Cys Gly Cys Gly Thr Gly Cys Cys Cys Thr
    50                  55                  60

Thr Cys Thr Cys Gly Cys Thr Gly Cys Thr Cys Gly Gly Ala Gly
65                  70                  75                  80

Cys Cys Cys Gly Ala Gly Cys Thr Gly Gly Ala Ala Cys Cys Ala
                85                  90                  95

Thr Thr Cys Cys Gly Gly Gly Ala Cys Thr Gly Gly Thr Ala Cys Cys
                100                 105                 110

Cys Thr Gly Cys Ala Cys Ala Cys Ala Gly Cys Cys Gly Cys Cys Thr
            115                 120                 125

Cys Thr Thr Cys Gly Ala Thr Cys Ala Ala Gly Cys Thr Thr Cys
    130                 135                 140

Gly Gly Gly Gly Thr Gly Cys Cys Cys Gly Gly Thr Thr Gly Cys
145                 150                 155                 160

Cys Cys Gly Ala Thr Gly Ala Gly Thr Gly Gly Thr Cys Gly Cys Ala
                165                 170                 175

Gly Thr Gly Gly Thr Thr Cys Ala Gly Cys Cys Cys Gly Cys Thr
            180                 185                 190

Gly Gly Gly Thr Gly Gly Cys Cys Cys Gly Gly Ala Thr Ala Cys Gly
    195                 200                 205
```

-continued

```
Thr Gly Cys Gly Cys Cys Cys Gly Cys Thr Gly Cys Cys Gly Cys
    210                 215                 220
Cys Gly Cys Gly Ala Cys Cys Gly Cys Cys Gly Ala Gly Gly Cys
225                 230                 235                 240
Cys Cys Cys Gly Cys Gly Gly Cys Gly Gly Thr Gly Ala Cys Cys
                245                 250                 255
Thr Gly Gly Cys Cys Gly Cys Ala Cys Ala Gly Cys Cys Thr Thr
            260                 265                 270
Cys Ala Gly Cys Cys Gly Ala Gly Cys Gly Cys Thr Cys Ala Ala Cys
            275                 280                 285
Cys Gly Ala Cys Ala Gly Cys Thr Cys Ala Gly Cys Ala Gly Cys Gly
        290                 295                 300
Gly Gly Gly Thr Cys Thr Cys Gly Gly Ala Gly Ala Thr Cys Cys Gly
305                 310                 315                 320
Ala Cys Ala Gly Ala Cys Gly Gly Cys Thr Gly Ala Thr Cys Gly Cys
                325                 330                 335
Thr Gly Gly Cys Gly Cys Gly Thr Gly Thr Cys Cys Thr Gly Gly
            340                 345                 350
Ala Cys Gly Thr Cys Ala Ala Cys Cys Ala Cys Thr Thr Cys Gly Cys
        355                 360                 365
Thr Cys Cys Gly Gly Ala Gly Gly Ala Gly Cys Thr Cys Ala Cys Ala
    370                 375                 380
Gly Thr Gly Ala Ala Gly Ala Cys Cys Ala Ala Gly Gly Ala Ala Gly
385                 390                 395                 400
Gly Cys Gly Thr Gly Gly Thr Gly Gly Ala Gly Ala Thr Cys Ala Cys
                405                 410                 415
Thr Gly Gly Cys Ala Ala Gly Cys Ala Cys Gly Ala Ala Gly Ala Ala
            420                 425                 430
Ala Gly Gly Cys Ala Gly Gly Ala Cys Gly Ala Ala Cys Ala Thr Gly
        435                 440                 445
Gly Cys Thr Ala Cys Ala Thr Cys Thr Cys Thr Gly Gly Thr Gly
    450                 455                 460
Cys Thr Thr Cys Ala Cys Cys Gly Gly Ala Ala Ala Thr Ala Cys
465                 470                 475                 480
Ala Cys Gly Cys Thr Cys Cys Thr Cys Cys Ala Gly Gly Thr Gly
                485                 490                 495
Thr Gly Gly Ala Cys Cys Cys Ala Cys Cys Cys Thr Ala Gly Thr
            500                 505                 510
Gly Thr Cys Cys Thr Cys Thr Cys Cys Cys Thr Ala Thr Cys Cys
        515                 520                 525
Cys Cys Thr Gly Ala Gly Gly Gly Cys Ala Cys Ala Cys Thr Thr Ala
    530                 535                 540
Cys Cys Gly Thr Gly Gly Ala Gly Gly Cys Thr Cys Cys Gly Thr Thr
545                 550                 555                 560
Gly Cys Cys Cys Ala Ala Ala Gly Cys Ala Gly Thr Cys Ala Cys Gly
                565                 570                 575
Cys Ala Gly Thr Cys Ala Gly Cys Gly Gly Ala Gly Ala Thr Cys Ala
            580                 585                 590
Cys Cys Ala Thr Thr Cys Cys Gly Gly Thr Thr Ala Cys Thr Thr
        595                 600                 605
Cys Gly Ala Gly Gly Cys Cys Cys Gly Cys Cys Cys Ala Ala
    610                 615                 620
Ala Thr Thr Gly Gly Gly Gly Gly Cys Cys Cys Ala Gly Ala Ala Gly
```

```
             625                 630                 635                 640
Cys Thr Gly Gly Gly Ala Ala Gly Thr Cys Thr Gly Ala Ala Cys Ala
                    645

```
            305                 310                 315                 320
Cys Cys Gly Cys Thr Gly Gly Cys Gly Cys Gly Thr Gly Thr Cys Cys
                325                 330                 335
Cys Thr Gly Gly Ala Thr Gly Thr Cys Ala Ala Cys Cys Ala Cys Thr
                340                 345                 350
Thr Cys Gly Cys Cys Cys Gly Cys Gly Ala Cys Gly Ala Gly Cys Thr
                355                 360                 365
Gly Ala Cys Gly Gly Thr Cys Ala Ala Gly Ala Cys Cys Ala Ala Gly
            370                 375                 380
Gly Ala Thr Gly Gly Cys Gly Thr Gly Gly Thr Gly Gly Ala Gly Ala
385                 390                 395                 400
Thr Cys Ala Cys Cys Gly Gly Cys Ala Ala Gly Cys Ala Cys Gly Ala
                405                 410                 415
Gly Gly Ala Gly Cys Gly Gly Cys Ala Gly Gly Ala Cys Gly Ala Gly
            420                 425                 430
Cys Ala Thr Gly Gly Cys Thr Ala Cys Ala Thr Cys Thr Cys Cys Cys
            435                 440                 445
Gly Gly Thr Gly Cys Thr Thr Cys Ala Cys Gly Cys Gly Gly Ala Ala
        450                 455                 460
Ala Thr Ala Cys Ala Cys Gly Cys Thr Gly Cys Cys Cys Cys Cys Cys
465                 470                 475                 480
Gly Gly Thr Gly Thr Gly Gly Ala Cys Cys Cys Ala Cys Cys Cys Cys
                485                 490                 495
Ala Ala Gly Thr Thr Thr Cys Cys Thr Cys Cys Thr Cys Cys Cys Thr
            500                 505                 510
Gly Thr Cys Cys Cys Cys Thr Gly Ala Gly Gly Gly Cys Ala Cys Ala
        515                 520                 525
Cys Thr Gly Ala Cys Cys Gly Thr Gly Gly Ala Gly Gly Cys Cys Cys
        530                 535                 540
Cys Cys Ala Thr Gly Cys Cys Ala Ala Gly Cys Thr Ala Gly Cys
545                 550                 555                 560
Cys Ala Cys Gly Cys Ala Gly Thr Cys Ala Ala Cys Gly Ala Gly
            565                 570                 575
Ala Thr Cys Ala Cys Ala Thr Cys Cys Ala Gly Thr Cys Ala
        580                 585                 590
Cys Cys Thr Thr Cys Gly Ala Gly Thr Cys Gly Cys Gly Gly Gly Cys
            595                 600                 605
Cys Cys Ala Gly Cys Thr Thr Gly Gly Gly Gly Cys Cys Cys Ala
        610                 615                 620
Gly Ala Ala Gly Cys Thr Gly Cys Ala Ala Ala Thr Cys Cys Gly
625                 630                 635                 640
Ala Thr Gly Ala Gly Ala Cys Thr Gly Cys Cys Gly Cys Cys Ala Ala
                645                 650                 655
Gly Thr Ala Ala Gly Ala Ala Thr Thr Cys
            660                 665

<210> SEQ ID NO 3
<211> LENGTH: 223
<212> TYPE: PRT
<213> ORGANISM: Homo sapiens

<400> SEQUENCE: 3

Met His His His His His His His Asp Asp Asp Asp Lys Met Thr
1               5                   10                  15
```

```
Glu Arg Arg Val Pro Phe Ser Leu Leu Arg Ser Pro Ser Trp Glu Pro
                20                  25                  30

Phe Arg Asp Trp Tyr Pro Ala His Ser Arg Leu Phe Asp Gln Ala Phe
             35                  40                  45

Gly Val Pro Arg Leu Pro Asp Glu Trp Ser Gln Trp Phe Ser Ala Ala
 50                  55                  60

Gly Trp Pro Gly Tyr Val Arg Pro Leu Pro Ala Ala Thr Ala Glu Gly
 65                  70                  75                  80

Pro Ala Ala Val Thr Leu Ala Ala Pro Ala Phe Ser Arg Ala Leu Asn
                 85                  90                  95

Arg Gln Leu Ser Ser Gly Val Ser Glu Ile Arg Gln Thr Ala Asp Arg
                100                 105                 110

Trp Arg Val Ser Leu Asp Val Asn His Phe Ala Pro Glu Glu Leu Thr
            115                 120                 125

Val Lys Thr Lys Glu Gly Val Val Glu Ile Thr Gly Lys His Glu Glu
            130                 135                 140

Arg Gln Asp Glu His Gly Tyr Ile Ser Arg Cys Phe Thr Arg Lys Tyr
145                 150                 155                 160

Thr Leu Pro Pro Gly Val Asp Pro Thr Leu Val Ser Ser Ser Leu Ser
                165                 170                 175

Pro Glu Gly Thr Leu Thr Val Glu Ala Pro Leu Pro Lys Ala Val Thr
                180                 185                 190

Gln Ser Ala Glu Ile Thr Ile Pro Val Thr Phe Glu Ala Arg Ala Gln
            195                 200                 205

Ile Gly Gly Pro Glu Ala Gly Lys Ser Glu Gln Ser Gly Ala Lys
210                 215                 220

<210> SEQ ID NO 4
<211> LENGTH: 219
<212> TYPE: PRT
<213> ORGANISM: Homo sapiens

<400> SEQUENCE: 4

Met His His His His His His His Asp Asp Asp Asp Lys Met Thr
 1               5                  10                  15

Glu Arg Arg Val Pro Phe Ser Leu Leu Arg Gly Pro Ser Trp Asp Pro
                20                  25                  30

Phe Arg Asp Trp Tyr Pro His Ser Arg Leu Phe Asp Gln Ala Phe Gly
             35                  40                  45

Leu Pro Arg Leu Pro Glu Glu Trp Ser Gln Trp Leu Gly Gly Ser Ser
 50                  55                  60

Trp Pro Gly Tyr Val Arg Pro Leu Pro Ala Ala Ile Glu Ser Pro
 65                  70                  75                  80

Ala Val Ala Ala Pro Ala Tyr Ser Arg Ala Leu Ser Arg Gln Leu Ser
                 85                  90                  95

Ser Gly Val Ser Glu Ile Arg His Thr Ala Asp Arg Trp Arg Val Ser
                100                 105                 110

Leu Asp Val Asn His Phe Ala Pro Asp Glu Leu Thr Val Lys Thr Lys
            115                 120                 125

Asp Gly Val Val Glu Ile Thr Gly Lys His Glu Glu Arg Gln Asp Glu
            130                 135                 140

His Gly Tyr Ile Ser Arg Cys Phe Thr Arg Lys Tyr Thr Leu Pro Pro
145                 150                 155                 160

Gly Val Asp Pro Thr Gln Val Ser Ser Ser Leu Ser Pro Glu Gly Thr
                165                 170                 175
```

```
Leu Thr Val Glu Ala Pro Met Pro Lys Leu Ala Thr Gln Ser Asn Glu
            180                 185                 190

Ile Thr Ile Pro Val Thr Phe Glu Ser Arg Ala Gln Leu Gly Gly Pro
        195                 200                 205

Glu Ala Ala Lys Ser Asp Glu Thr Ala Ala Lys
        210                 215

<210> SEQ ID NO 5
<211> LENGTH: 129
<212> TYPE: PRT
<213> ORGANISM: Artificial Sequence
<220> FEATURE:
<223> OTHER INFORMATION: Recombinant truncated form of HSP27 protein
      consisting of the biologically inactive C-terminus

<400> SEQUENCE: 5

Met His His His His His His His Asp Asp Asp Lys Gly Gly
1               5                   10                  15

Asp Arg Trp Arg Val Ser Leu Asp Val Asn His Phe Ala Pro Asp Glu
            20                  25                  30

Leu Thr Val Lys Thr Lys Asp Gly Val Val Glu Ile Thr Gly Lys His
        35                  40                  45

Glu Glu Arg Gln Asp Glu His Gly Tyr Ile Ser Arg Cys Phe Thr Arg
    50                  55                  60

Lys Tyr Thr Leu Pro Pro Gly Val Asp Pro Thr Gln Val Ser Ser Ser
65                  70                  75                  80

Leu Ser Pro Glu Gly Thr Leu Thr Val Glu Ala Pro Met Pro Lys Leu
                85                  90                  95

Ser Thr Gln Ser Asn Glu Ile Thr Ile Pro Val Thr Phe Glu Ser Arg
            100                 105                 110

Ala Gln Leu Gly Gly Pro Glu Ala Ala Lys Ser Asp Glu Thr Ala Ala
        115                 120                 125

Lys

<210> SEQ ID NO 6
<211> LENGTH: 10
<212> TYPE: PRT
<213> ORGANISM: Artificial Sequence
<220> FEATURE:
<223> OTHER INFORMATION: Signature peptide for HSP27

<400> SEQUENCE: 6

Leu Phe Asp Gln Ala Phe Gly Leu Pro Arg
1               5                   10
```

MODULATION OF PROPROTEIN CONVERTASE SUBTILISIN/KEXIN 9 EXPRESSION (PCSK9) WITH HSP 27 AND/OR HSP25

RELATED APPLICATION

This application is a national phase entry application of Patent Cooperation Treaty Application No. PCT/CA2016/051018, filed Aug. 29, 2016 (which designates the U.S.), which claims the benefit under 35 USC § 119(e) from U.S. Provisional Application No. 62/211,190, filed on Aug. 28, 2015, both of which are incorporated herein by reference in their entirety.

INCORPORATION OF SEQUENCE LISTING

A computer readable form of the Sequence Listing "21806-P55380US00_SequenceListing.txt" (20,480 bytes), submitted via EFS-WEB and created on Feb. 28, 2018, is herein incorporated by reference.

TECHNICAL FIELD

This disclosure generally relates to management and/or reduction of high cholesterol levels in mammalian subjects. More specifically, this disclosure pertains to use of heat shock protein 27 (HSP27) to reduce expression of proprotein convertase subtilisin/kexin type 9 (PCSK9) in mammalian subjects.

BACKGROUND

Proprotein convertase subtilisin/kexin type 9 (PSCK9) is a serine protease family member that binds to and regulates low density lipoprotein (LDL) receptor expression on the surface of cells. Inhibition of the LDL receptor-PCSK9 interaction is an attractive approach to the treatment of cholesterol disorders. Inhibition of interactions between large proteins (i.e., protein-protein interactions or PPI) by the use of antibodies or small molecule inhibitors is, however, generally regarded as being particularly difficult and challenging. Large proteins such as PCSK9, with a molecular weight of about 74 KDa, and LDLR, with a molecular weight of about 160 KDa (glycosylated on cell surface; 115 KDa in immature form), are likely to exhibit extensive intermolecular contacts over a large area. The existence of extensive contacts makes it unlikely that a given antibody or small molecule inhibitor will successfully block their binding.

One method for lowering LDL cholesterol levels is by administration of HMG-CoA reductase inhibiting drugs. These drugs antagonize HMG-CoA reductase and cholesterol synthesis in the liver and increase the number of hepatic LDL receptors on the cell-surface to enhance uptake and catabolism of LDL. A drawback of such an approach is that these drugs commonly suffer from a disadvantageous side-effect profile, including, for example, liver toxicity, and up-regulating SREBP-2 (the transcriptional factor that promotes synthesis of PCSK9).

SUMMARY

Some embodiments of the present disclosure relate to use of heat shock protein 27 (HSP27) to reduce the expression of proprotein convertase subtilisin/kexin type 9 (PCSK9) in mammalian subjects.

Some embodiments of the present disclosure relate to use of anti-HSP27 antibodies to supplement and/or to enhance the use of HSP27 to reduce the expression of PCSK9 in mammalian subjects.

Some embodiments of the present disclosure relate to compositions for enhancing the efficacy of HSP27 reduction of PCSK9 expression in mammalian subjects.

BRIEF DESCRIPTION OF THE FIGURES

The exemplary embodiments of the present disclosure will be described with reference to the following drawings in which:

FIG. 2A and FIG. 2(B) are charts showing the results of double dilution analyses with a commercial ELISA test kit wherein FIG. 2A shows the results for a first serum sample and FIG. 2B shows the results for a second serum sample;

FIG. 3A shows a schematic workflow diagram for a MRM-MS method according to an embodiment of the present disclosure, while FIG. 3B shows a schematic workflow diagram for quantification of HSP27 with the MRM-MS method shown in FIG. 3A;

FIG. 4A top panel shows an ion chromatogram of pure recombinant HSP27 after trypsin digestion by Enhanced Mass spectrum (EMS) mode while the bottom panel of FIG. 4A is the full scan of upper panel peak at 18.63 min; FIG. 4B top panel shows an ion chromatogram of ion product 582.6(++) by enhanced product ion (EPI) mode while the bottom panel of FIG. 4B is the full scan of upper panel peak at 18.63 min wherein the selected transition ions are circled; FIG. 4C top panel shows an ion chromatogram of synthesized AQUA peptide by EMS mode while the bottom panel of FIG. 4C is the full scan of upper panel peak at 18.63 min; and FIG. 4D top panel shows an ion chromatogram of ion product 585.9(++) by EPI mode while the bottom panel of FIG. 4D is the full scan of upper panel peak at 18.63 min wherein the selected transition ions from AQUA peptide are circled;

FIG. 5A and FIG. 5B show results obtained with the MRM-MS method shown in FIG. 3A, wherein FIG. 5A is a chart showing Protein G magnet beads pulled down HSP27 from human serum while FIG. 5B is a chart showing a standard regression curve using variable trypsin digested recombinant HSP27 and stable AQUA peptide; FIG. 5C and FIG. 5D show an example results obtained from human serum samples tested by the MRM method from FIG. 3A wherein FIG. 5C panel is the signal of each selected transitions from endogenous digested HSP27 while FIG. 5D is a chart showing the intensity of each selected transition from the spiked AQUA peptide; FIG. 5E is a chart showing calculated HSP27 levels in 10 human serum samples using the MRM-MS method from FIG. 3A;

FIG. 6 is a chart showing a uniqueness analysis of selected transitions using the SRM COLLIDER® program (COLLIDER is a registered trademark of Zyomed Corp, Pasedina, Calif., USA);

FIG. 7A-FIG. 7E are charts illustrating results obtained the MRM-MS method disclosed herein for quantification of HSP27 in serum samples wherein FIG. 7A shows the repeatability of the present MRM-MS assay, FIG. 7B shows the recovery of rHSP27 after spiking 100 ng/ml HSP27 with human serum, FIG. 7C shows the effects of 1×, 2×, 4×, and 8× double-dilution testing with the present MRM-MS method, FIG. 7D shows a parallelism test for the present MRM-MS method, and FIG. 7E show the stability of HSP27 in human serum at −20° C.;

FIG. 9A is a chart showing the effects of HSP27 on the accumulation of proteins and peptides in HepG2 liver cells, while FIG. 9B is a chart showing the effects of a mixture of HSP27 plus anti-HSP27 AAbs on the accumulation of proteins and peptides in HepG2 liver cells;

FIG. 10A is a chart showing the effects of 200 ug/ml rHSP27 on PCSK9 mRNA expression in HepG2 liver cells as measured by quantitative RT-PCR, while FIG. 10B is a chart showing the effects of co-treatment with rHSP27 (1 ug/ml) and Pab (5 ug/ml) (dark grey bars) compared to controls (light grey bars) on PCSK9 mRNA expression in HepG2 liver cells as measured by quantitative RT-PCR.

FIG. 11A shows the effects of 200 ug/ml rHSP27 on mRNA levels over 6 hr (top panel) and protein levels after 24 hr (bottom panel) of the PCSK9 transcription factor, HNF-1a. FIG. 11B is a chart showing the effects of co-treatment with rHSP27 (1 ug/ml) and Pab (5 ug/ml) (dark grey bars) compared to controls (light grey bars), on HNF-1a mRNA; FIG. 11C is a chart showing the effects of co-treatment with rHSP27 (1 ug/ml) and Pab (5 ug/ml) (dark grey bars) compared to controls (light grey bars), on α-trypsin mRNA; FIG. 11D is a chart showing the effects of co-treatment with rHSP27 (1 ug/ml) and Pab (5 ug/ml) (dark grey bars) compared to controls (light grey bars), on fibrinogen-β mRNA;

FIG. 15A shows Western blots of PSCK-9 and β-Actin with a chart showing the effects on PCSK9 expression in HepG2 (liver) cells after a 1-hr treatment with 17 β-pestradiol, while FIG. 15B shows Western blots of PSCK-9 and β-Actin with a chart showing the effects on PCSK9 expression in HepG2 (liver) cells after a 1-hr treatment with rHSP27;

FIG. 16A shows Western blots of LDL-R and β-Actin with a chart showing the effects on LDL-R receptor expression in HepG2 (liver) cells after a 6-hr treatment with 17 β-estradiol, while FIG. 16B shows Western blots of LDL-R and β-Actin with a chart showing the effects on LDL-R expression in HepG2 (liver) cells after a 6-hr treatment with rHSP27;

FIG. 18A is a chart showing HSP27 AAb levels in plasma after injection of rHSP27 without adjuvant; FIG. 18B is a chart showing HSP27 levels in plasma after injection of rHSP27 mixed with Freund's Incomplete Adjuvant; while FIG. 18C is a chart comparing the effects of adjuvant on HSP27 AAb levels over a 21-day period;

FIG. 27A is a chart showing serum PCSK9 levels in male apoE$^{-/-}$ mice in the non-fasting state after completing a 4 week high fat diet, while FIG. 27B is a chart showing serum PCSK9 levels in male apoE$^{-/-}$ mice in the fasting state after completing a 4 week high fat diet wherein the black bars show the effects of the alum adjuvant plus rHSP25 treatment while the grey bars show the effects of the alum adjuvant and rHSP27-C1 treatment (control);

FIG. 33A-FIG. 33F are charts showing age-matched and sex-matched comparisons of human serum HSP27 and anti-HSP27 autoantibody (AAb) levels stratified according sex and age wherein FIG. 33A is a chart comparing serum levels of HSP27 in females and males; FIG. 33B is a chart comparing serum levels of anti-HSP27 autoantibodies in females and males; FIG. 33C is a chart comparing serum levels of HSP27 in females aged≤60 yrs vs. females aged≥60 yrs; FIG. 33D is a chart comparing serum levels of anti-HSP27 autoantibodies in females aged≤60 yrs vs. females aged≥60 yrs; FIG. 33E is a chart comparing serum levels of HSP27 in males aged≤60 yrs vs. males aged≥60 yrs; FIG. 33F is a chart comparing serum levels of anti-HSP27 autoantibodies in males aged≤60 yrs vs. males aged>60 yrs.

DETAILED DESCRIPTION

Figure 1:
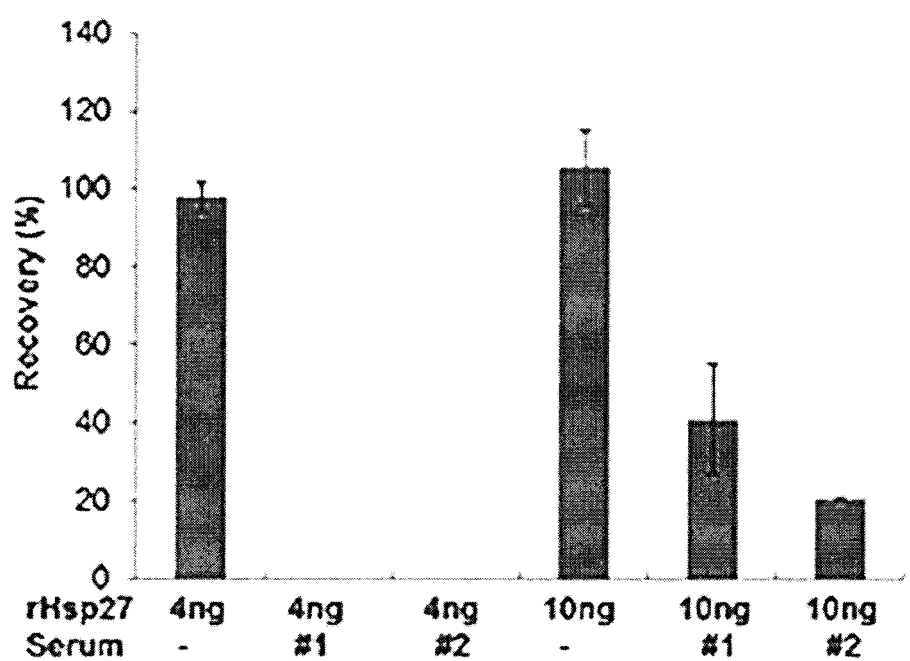
FIG. 1 is a chart showing the results of HSP27 recovery with results generated with a commercial ELISA test kit.

Unless defined otherwise, all technical and scientific terms used herein have the same meaning as commonly understood by one of ordinary skill in the art to which the disclosure belongs. Certain terms are discussed in the specification to provide additional guidance to the practitioner in describing the methods, uses and the like of embodiments of the disclosure, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Recital of one or a few synonyms or equivalents does not exclude use of other synonyms or equivalents, unless it is explicitly stated. Use of examples in the specification, including examples of terms, is for illustrative purposes only and does not limit the scope and meaning of the embodiments of the disclosure herein. Although any methods and materials similar or equivalent to those described herein can be used in the practice or testing of the present disclosure, the preferred methods and materials are now described.

To facilitate understanding of the disclosure, the following definitions are provided.

The word "comprise" or variations such as "comprises" or "comprising" will be understood to imply the inclusion of a stated integer or groups of integers but not the exclusion of any other integer or group of integers.

As used herein, the word "complexed" means attached together by one or more linkages.

The term "a cell" includes a single cell as well as a plurality or population of cells. Administering an agent to a cell includes both in vitro administrations and in vivo administrations.

The term "subject" as used herein includes all members of the animal kingdom, and specifically includes humans.

The term "about" or "approximately" means within 20%, preferably within 10%, and more preferably within 5% of a given value or range.

The term "homologous" in all its grammatical forms and spelling variations refers to the relationship between proteins that possess a "common evolutionary origin," including homologous proteins from different species. Such proteins (and their encoding genes) have sequence homology, as reflected by their high degree of sequence similarity. This homology is greater than about 80%, greater than about 85%. In some cases, the homology will be greater than about 90% to 95% or 98%.

The term "polypeptide" refers to a polymeric compound comprised of covalently linked amino acid residues. Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group. A polypeptide of the disclosure preferably comprises at least about 14 amino acids.

The term "protein" refers to a polypeptide which plays a structural or functional role in a living cell.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

The term "derivative" refers to a product comprising, for example, modifications at the level of the primary structure, such as deletions of one or more residues, substitutions of one or more residues, and/or modifications at the level of one or more residues. The number of residues affected by the modifications may be, for example, from 1 or 2 or 3 to 10 or 20 or 30 residues. The term derivative also comprises molecules comprising additional internal or terminal parts, for example, of a peptide nature or otherwise. The internal or terminal parts may be in particular active parts, markers, amino acids, such as methionine at position −1. The term derivative also comprises molecules comprising modifications at the level of the tertiary structure (e.g., N-terminal end and the like). The term derivative also comprises sequences homologous to the sequence considered, derived from other cellular sources and in particular, from cells of human origin or from other organisms, and possessing activity of the same type or of substantially similar type. Such homologous sequences may be obtained by hybridization experiments. The hybridizations may be performed based on nucleic acid libraries using as probe, the native sequence or a fragment thereof, under conventional stringency conditions or preferably under high stringency conditions.

The term "antibody" as used herein refers to a glycoprotein comprising at least two heavy (H) chains and two light (L) chains inter-connected by disulfide bonds. Each heavy chain is comprised of a heavy chain variable region (abbreviated herein as HCVR or VH) and a heavy-chain constant region. The heavy-chain constant region is comprised of three domains: CH1, CH2, and CH3. Each light chain is comprised of a light-chain variable region (abbreviated herein as LCVR or VL) and a light-chain constant region. The light-chain constant region is comprised of one domain:

CL. The VH and VL regions can be further subdivided into regions of hypervariability termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy chains and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding fragment" of an antibody as used herein, refers to one or more portions of an antibody that retain the ability to specifically bind to an antigen. It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., 1989, *Binding activities of a repertoire of single immunoglobulin variable domains secreted from Escherichia coli*. Nature 341:544-546) which consists of a VH domain; and (vi) an isolated complementarity determining region (CDR). Furthermore, although the two domains of the Fv fragment, V and VH, are coded for by separate genes, they can be joined, using recombinant methods, by a synthetic linker that enables them to be made as a single protein chain in which the VL and VH regions pair to form monovalent molecules (known as single chain Fv (scFv) using for example, methods taught by Bird et al. (1988, *Single chain antigen binding proteins*. Science 242:423-426) and Huston et al. (1988, *Protein engineering of antibody binding sites: recovery of specific activity in an anti-digoxin single-chain Fv analogue produced in Escherichia coli*. Proc. Natl. Acad. Sci. USA 85:5879-5883). Such single chain antibodies are also intended to be encompassed within the term "antigen-binding portion" of an antibody. These antibody fragments are obtained using conventional procedures, such as proteolytic fragmentation procedures, as described in *Monoclonal Antibodies: Principles and Practice* (James Gooding (Ed.) 1983, N.Y. Academic Press, pp 98-118). The fragments are screened for utility in the same manner as are intact antibodies.

An "isolated antibody", as used herein, is intended to refer to an antibody which is substantially free of other antibodies having different antigenic specificities. As used herein, "specific binding" refers to antibody binding to a predetermined antigen. Typically, the antibody binds with an affinity that is at least two-fold greater than its affinity for binding to a non-specific antigen (e.g., BSA, casein) other than the predetermined antigen or a closely-related antigen.

The term "complementarity determining regions" as used herein refers to the regions within antibodies where these proteins complement an antigen's shape. The acronym CDR is used herein to mean "complementarity determining region".

The embodiments of the present disclosure generally relate to use of heat shock proteins to reduce the expression of proprotein convertase subtilisin/kexin type 9 (PSCK9) in mammalian subjects thereby reducing their levels of low-density lipoprotein (LDL) cholesterol.

Heat shock proteins are involved in a wide variety of processes, both physiological and pathological. Heat shock protein 27 (HSP27) is a member of the small heat shock protein family, which comprises members ranging from 15 to 30 kDa in size and which may be phosphorylated or oligomerized under various conditions. HSP27 is principally described as an intracellular chaperone capable of binding and stabilizing the actin cytoskeleton in response to stress. In addition, HSP27 can bind cytochrome c and prevent downstream caspase activation, making it a potent anti-apoptotic protein. Although multi-faceted, the functions described for HSP27 have been solely thought to be within the confines of the cell membrane. However, extracellular release of HSP27 may be regulated and may have important effects on steps leading to the development of atherosclerosis. For example, increasing HSP27 levels in a mammalian subject may decrease plaque cholesterol and inflammatory cell content and/or may decrease serum cholesterol levels when it is over-expressed.

We have discovered that HSP27 directly interferes with expression of the PCSK9 proteins. Accordingly, one aspect of this disclosure pertains to the use of HSP27 and/or compositions comprising HSP27 to controllably reduce the expression of PCSK9 proteins in mammalian subjects. Another aspect of this disclosure pertains to methods for the use of HSP27 and/or compositions comprising HSP27 to controllably reduce the expression of PCSK9 proteins in mammalian subjects.

We have also discovered that the efficacy of HSP27 in reducing the expression of PCSK9 proteins in mammalian subjects can be significantly augmented by increasing anti-HSP27 antibodies through the use of adjuvants. Accordingly, some embodiments of this disclosure pertain to pharmaceutical compositions comprising mixtures of one or more of HSP27 proteins and adjuvants, use of the pharmaceutical compositions to reduce expression of PCSK9 proteins in mammalian subjects, and to methods for the use of the pharmaceutical compositions to reduce expression of PCSK9 proteins in mammalian subjects.

We have also surprisingly discovered that the expression of PCSK9 proteins in mammalian subjects can be reduced by co-administration of anti-HSP27 antibodies and HSP27. Accordingly, some embodiments of the present disclosure pertain to pharmaceutical compositions comprising anti-HSP27 antibodies, use of the anti-HSP27 antibody compositions, and methods for the use of the anti-HSP27 antibody compositions. Other embodiments of the present disclosure pertain to pharmaceutical compositions comprising a mixture of HSP27 and anti-HSP27 antibodies, use of the HSP27/anti-HSP27 antibody compositions, and methods for the use of the HSP27/anti-HSP27 antibody compositions.

Accordingly, one embodiment of the present disclosure pertains to pharmaceutical compositions for interfering with and reducing expression of PCSK9 proteins in mammalian cells. The compositions may comprise HSP27 proteins or fragments thereof and an adjuvant. The compositions may comprise HSP25 proteins or fragments thereof and an adjuvant. The compositions may comprise recombinant HSP25 peptides, referred to herein as rHSP25 peptides, and/or recombinant HSP27 peptides, referred to herein as rHSP27 peptides, and a suitable adjuvant. Suitable adjuvants are exemplifed by Freund's complete cdjuvant, by Freund's incomplete adjuvant, by an alum adjuvant comprising aluminum hydroxide for example ALHYDROGEL® (ALHY- DROGEL is a registered trademark of Brenntag Biosector A/S, Ballerup, DK), aluminum phosphate, squalene, mineral oil, paraffin oil, and the like.

An example of a suitable rHSP25 petide is shown in SEQ ID NO:1. Other rHSP25 peptides suitable for incorporation into the pharmaceutical compositions disclosed herein will have an 80% or more homology with SEQ ID NO: 1, an 85% or more homology with SEQ ID NO: 1, a 90% or more homology with SEQ ID NO: 1, or a 95% or more homology with SEQ ID NO: 1.

An example of a suitable rHSP27 petide is shown in SEQ ID NO: 2. Other rHSP27 peptides suitable for incorporation into the pharmaceutical compositions disclosed herein will have an 80% or more homology with SEQ ID NO: 2, an 85% or more homology with SEQ ID NO: 2, a 90% or more homology with SEQ ID NO: 2, or a 95% or more homology with SEQ ID NO: 2.

An example of a suitable HSP25 protein is shown in SEQ ID NO:3. Fragments of HSP25 proteins suitable for incorporation into the pharmaceutical compositions disclosed herein will have an 80% or more homology with SEQ ID NO: 3, an 85% or more homology with SEQ ID NO: 3, a 90% or more homology with SEQ ID NO: 3, or a 95% or more homology with SEQ ID NO: 3.

An example of a suitable HSP27 protein is shown in SEQ ID NO: 4. Fragments of HSP27 proteins suitable for incorporation into the pharmaceutical compositions disclosed herein will have an 80% or more homology with SEQ ID NO: 4, an 85% or more homology with SEQ ID NO: 4, a 90% or more homology with SEQ ID NO: 2, or a 95% or more homology with SEQ ID NO: 4.

According to one embodiment, an example of a pharmaceutical composition for disrupting and or reducing the expression of PCSK9 in mammalian cells comprises one of a HSP27 protein or fraction thereof, a HSP25 protein or fraction thereof, a rHSP25 peptide or a rHSP27 peptide in a mixture with Freund's adjuvant. Another example of a suitable pharmaceutical composition of a mixture comprising a rHSP25 peptide, a rHSP27 peptide, and Freund's incomplete adjuvant. Suitable ratios of peptide/adjuvant are in the ranges of 1:1, 1:2, 1:3, and therebetween.

According to another to another embodiment, an example of a pharmaceutical composition for disrupting and or reducing the expression of PCSK9 in mammalian cells comprises one of a HSP27 protein or fraction thereof, a HSP25 protein or fraction thereof, rHSP25 peptide, or a rHSP27 peptide in a mixture with an adjuvant comprising aluminum hydroxide. Another example of a suitable pharmaceutical composition is a mixture comprising a rHSP25 peptide, a rHSP27 peptide, and an aluminum hydroxide adjuvant. A suitable aluminum hydroxide adjuvant is a wet gel formulation exemplified by ALHYDROGEL®. Suitable ratios of peptide/adjuvant are in the ranges of 1:1, 1:2, 1:3, and therebetween.

The pharmaceutical compositions disclosed herein may be formulated for delivery by injection. In addition to the mixture of (i) a HSP27 protein or fraction thereof, a HSP25 protein or fraction thereof, a rHSP25 peptide and/or a rHSP27 peptide, and (ii) adjuvant, the injectable pharmaceutical compositions may additionally comprise a carrier such as sterile water, buffered saline solutions, buffered phosphate solutions, and the like at physiological pH. The carrier solution may comprise in a total amount by weight of about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4%, about 5.5%, about 5.6%, about 5.7%, about 5.8%, about 5.9%, about 6.0%, about 6.1%, about 6.2%, about 6.3%, about 6.4%, about 6.5%, about 6.6%, about 6.7%, about 6.8%, about 6.9%, about 7.0%, about 7.1%, about 7.2%, about 7.3%, about 7.4%, about 7.5%, about 7.6%, about 7.7%, about 7.8%, about 7.9%, about 8.0%, about 8.1%, about 8.2%, about 8.3%, about 8.4%, about 8.5%, about 8.6%, about 8.7%, about 8.8%, about 8.9%, about 9.0%, about 9.1%, about 9.2%, about 9.3%, about 9.4%, about 9.5%, about 9.6%, about 9.7%, about 9.8%, about 9.9% or about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, or about 95%.

According to one aspect, the injectable pharmaceutical compositions may additionally incorporate one or more non-aqueous solvents exemplified by propylene glycol, polyethylene glycol, vegetable oils such as olive oil, and injectable organic esters exemplified by ethyl oleate.

According to another aspect, the injectable pharmaceutical compositions may additionally incorporate one or more of antimicrobials, anti-oxidants, chelating agents, and the like.

The injectable pharmaceutical compositions may be presented in unit-dose or multi-dose containers exemplified by sealed ampules and vials.

The pharmaceutical compositions disclosed herein may be formulated for oral administration. The oral pharmaceutical compositions may be provided as capsules or tablets, as powders or granules, as solutions, syrups or suspensions (in aqueous or non-aqueous liquids), comprising therein one of a HSP27 protein or fraction thereof, a rHSP25 peptide, or a rHSP27 peptide. The oral pharmaceutical compositions may comprise a mixture of a rHSP25 peptide and a rHSP27 peptide. Tablets or hard gelatine capsules may comprise, for example, lactose, starch or derivatives thereof, magnesium stearate, sodium saccharine, cellulose, magnesium carbonate, stearic acid or salts thereof. Soft gelatine capsules may comprise, for example, vegetable oils, waxes, fats, semi-solid, or liquid polyols, etc. Solutions and syrups may comprise, for example, water, polyols and sugars. The HSP27 protein or fraction thereof, a rHSP25 peptide and/or a rHSP27 peptide may be coated with or admixed with a material (e.g., glyceryl monostearate or glyceryl distearate) that delays disintegration or affects absorption of the active agent in the gastrointestinal tract. Thus, for example, the sustained release of an active agent may be achieved over many hours and, if necessary, the active agent can be protected from being degraded within the gastrointestinal tract. Taking advantage of the various pH and enzymatic conditions along the gastrointestinal tract, pharmaceutical compositions for oral administration may be formulated to facilitate release of an active agent at a particular gastrointestinal location.

The pharmaceutical compositions described herein are used in a "pharmacologically effective amount." A "pharmacologically effective amount" is the amount of a HSP27 protein or fraction thereof, a HSP25 protein or fraction thereof, a rHSP25 peptide, and/or a rHSP27 peptide in the composition which is sufficient to deliver a therapeutic amount of the active agent during the dosing interval in which the pharmaceutical composition is administered. Accordingly, the amount of the pharmaceutical composition administered to deliver a therapeutically effective amount of a HSP27 protein or fraction thereof, a HSP25 protein or fraction thereof, a rHSP25 peptide, and/or a rHSP27 peptide is about 0.01 g, about 0.05 g, about 0.1 g, about 0.2 g, about 0.3 g, about 0.4 g, about 0.5 g, about 0.6 g, about 0.7 g, about 0.8 g, about 0.9 g, about 1 g, about 1.1 g, about 1.2 g, about 1.3 g, about 1.4 g, about 1.5 g, about 1.6 g, about 1.7 g, about 1.8 g, about 1.9 g, about 2 g, about 2.1 g, about 2.2 g, about 2.3 g, about 2.4 g, about 2.5 g, about 2.6 g, about 2.7 g, about 2.8 g, about 2.9 g, about 3 g, about 3.1 g, about 3.2 g, about 3.3 g, about 3.4 g, about 3.5 g, about 3.6 g, about 3.7 g, about 3.8 g, about 3.9 g, about 4 g, about 4.1 g, about 4.2 g, about 4.3 g, about 4.4 g, about 4.5 g, about 4.6 g, about 4.7 g, about 4.8 g, about 4.9 g, about 5 g, about 5.1 g, about 5.2 g, about 5.3 g, about 5.4 g, about 5.5 g, about 5.6 g, about 5.7 g, about 5.8 g, about 5.9 g, about 6 g, about 6.1 g, about 6.2 g, about 6.3 g, about 6.4 g, about 6.5 g, about 6.6 g, about 6.7 g, about 6.8 g, about 6.9 g, about 7 g, about 7.1 g, about 7.2 g, about 7.3 g, about 7.4 g, about 7.5 g, about 7.6 g, about 7.7 g, about 7.8 g, about 7.9 g, about 8 g, about 8.1 g, about 8.2 g, about 8.3 g, about 8.4 g, about 8.5 g, about 8.6 g, about 8.7 g, about 8.8 g, about 8.9 g, about 9 g, about 9.1 g, about 9.2 g, about 9.3 g, about 9.4 g, about 9.5 g, about 9.6 g, about 9.7 g, about 9.8 g, about 9.9 g or about 10 g.

Another embodiment disclosed herein relates to a sensitive, selective, and high-throughput multiple-reaction-monitoring (MRM) based MS method for separating out and quantifying HSP27 proteins and anti-HSP27 auto-antibodies (HSP27 AAb) from serum samples. An example of the MRM-MS method disclosed herein comprises the steps of: (i) diluting a serum sample in a buffered solution, (ii) adding a pre-determined amount of protein G magnet DYNABEADS® (DYNABEADS is a registered trademark of Invitrogen Dynal AS Corp. Smestad, Norway) onto which has been coated an AQUA peptide comprising the peptide sequence set forth in SEQ ID NO: 6, to the diluted serum sample, (iii) after a mixing period of 1-h at room temperature, washing the magnet beads twice with fresh buffer solution, (iv) adding ABC buffer with 20 mM DTT to the washed beads and mix well, (v) boil the beads at 100° C. for 20 min to denature proteins that were pulled down onto the DYNABEADS® and then cool to room temperature, (vi) add trypsin in ABC buffer to the cooled beads and incubate at 37° C. for 48 hours to digest the pulled down proteins, (vii) stop the reaction by addition of 2% formic acid, (viii) separating the solution from the beads, (ix) analysing the solution with LC-MS/MS, and (x) correlating the data generated by the LC-MS/MS analysis with a reference to a known HSP27 standard.

The present disclosure will be further elaborated in the following examples.

EXAMPLES

Example 1

Development of a Multiple-Reaction-Monitoring Based Method for the Quantification of HSP27 and anti-HSP27 AAbs in Human Serum Similar to other heat shock proteins, HSP27 and HSP25 act as auto-antigen and induces B-cell and T-cell immunological responses, thereby innately producing a natural antibody directly against the HSP27 that is present in human circulation. It is known that rather complex patterns of interference by heterophilic anti-immunoglobulin antibodies results in questionable and unreliable data with standard ELISA methods (Hennig et al. 2000, *The influence of naturally occurring heterophilic anti-immunoglobulin antibodies on direct measurement of serum proteins using sandwich ELISAs*. J. Immunol. Methods 235(1-2):71-800). Furthermore, a recent study demonstrated that a large number of commercial ELISA kits generated conflicting and unreliable data pertaining to HSP27 levels in serum (Zimmermann et al., 2014, *Circulating heat shock protein 27 as a biomarker for the differentiation of patients with lung cancer and healthy controls—a clinical comparison of different enzyme linked immunosorbent assays*. Clin. Lab. 60(6):999-1006). Accordingly, a new method is disclosed herein for precise and accurate detection and quantification of HSP27 and anti-HSP27 AAbs in serum samples.

Reagents and Chemicals:

All chemicals were from LC-MS grade quality or from the highest analytical grade available. Water, ACN, DL-dithiothreitol (DTT), Iodoacetamide (IAA), Ammonium bicarbonate (ABC) and formic acid were from Sigma-Aldrich (St. Louis, USA). Sequencing-grade modified porcine trypsin (T6567) from Sigma (St. Louis, US) was used for all experiments. Serum samples were obtained from University of South Alabama.

Instruments:

The LC-MS/MS analyses were performed using a DIONEX® 3000 chromatographic system (DIONEX is a registered trademark of Dionex Corp., Sunnyvale, Calif., USA) coupled to a QTRAP® 4500 triple quadrupole mass spectrometer (QTRAP is a registered trademark of AB SCIEX Pte. Ltd., Singapore). The analytical column, THERMO SCIENTIFIC® Acclaim PepMap300 C18, 5 μm Particle Size, 150 mm×1.0 mm I.D., with 5 μm particle size (THERMO SCIENTIFIC is a registered trademark of Thermo Fisher Scientific inc., Waltham, Mass., USA) was protected by a Polaris C18-A guard column, 10 mm×2.0 mm I.D. with 5 μm particle size (Varian Inc., Palo Alto, Calif., USA).

LC-MS/MS Conditions:

Formic acid (0.1%, v/v) in water was used as eluent A and ACN with 0.1% formic acid was as eluent B. The flow rate was set to 50 μl/min and column temperature to 25° C. During 10 min after injection, eluent B was increased from 30 to 40% for 20 minutes, followed by an increase to 70% for 5 minutes for wash and 2% for 5 minutes for re-equilibration. MS signal was collected after 10 min of sample injection. The digested recombinant HSP27 were used to determine retention times and optimize MRM settings. Collision energy (CE) and De-clustering potential (DP) were optimized by measuring selected transitions peak areas at CE and DP values varying from the theory CV and DP calculated by Skyline software using scheduled MRM mode with CV and DP optimization. In general, double charged $[M^{+2H}]^{2+}$ ions of selected peptide and AQUA peptide were selected as precursor ions, whereas single charged y-ions ($y^{8+}$, $y^{6+}$, $y^{5+}$ and $y^{4+}$) of both light peptide from rHSP27 and AQUA peptide with optimal MS response were selected as product ions for quantitation.

Recombinant Protein Preparation:

N-terminal His-tagged HSP27 overexpression plasmid was constructed into a pET-21a vector, and the plasmids were transformed into an *Escherichia coli* expression strain (DE3) following the methods taught by Raizman et al. (2013, *Heat shock protein-27 attenuates foam cell formation and atherogenesis by down-regulating scavenger receptor-A expression via NF-kappaB signaling.* Biochim. Biophys. Acta 1831(12):1721-1728). Recombinant proteins were purified by with a Ni-NTA resin and Q-SEPHAROSE® (SEPHAROSE is a registered trademark of GE Healthcare Bio-Sciences AB Ltd., Uppsala, Sweden). Endotoxin was removed by High-Capacity Endotoxin Removal Resin (Pierce). The purity of the final recombinant proteins were determined to be more than 99% by SDS-PAGE with a concentration lower than 2 endotoxin units/mg protein by Limulus Amebocyte Lysate PYROGENT® 125 Plus (PYROGENT is a registered trademark of Lonza Walkersville Inc., Walkersville, Md., USA).

Peptide Selection and AQUA Peptide Preparation:

Initially the peptide was selected from recombinant HSP27 with trypsin digestion based on their MS intensity using enhanced mass spectrum mode. Ion products of higher MS abundant peptides were detected using enhanced product ions mode. The peptide LFDQAFGLPR (SEQ ID NO: 6) was finally selected as the signature peptide of HSP27 for quantification. The selected peptide and transitions were confirmed by human serum samples using MRM. AQUA peptide of LFDQAFGLPR (SEQ ID NO: 6) was synthesized by ThermoFisher Scientific (German) with L34 (13C6, 15N) wherein the second leucine was labelled with $^{13}C$ and the purity of AQUA peptide was assessed by reversed-phase HPLC and MALDI-TOP-MS. The sequences of AQUA peptide was confirmed by enhanced product ion analysis.

Digestion (Denaturation/Reduction, Alkylation and Tryptic Digestion):

75 ul human serum was diluted to 225 μl PBS buffer and then added to 50 μl protein G magnet DYNABEADS®. The solution was mixed at room temperature for 1 h and then washed twice by 1 ml PBS. 75 μl of ABC buffer with 20 mM DTT was finally added to the drained beads and mixed well at room temperature for 30 min. Then, the samples were boiled at 100° C. for 20 min to denature proteins. After the samples were boiled, the beads were cooled down at room temperature for 30 minutes. 25 μl of trypsin (120 ug/ml) in 50 mM ABC buffer was finally applied to the beads. The total reaction volume was 100 μl. Digestion of the pulled-down proteins was performed at 37° C. for 48 hours. The digestion reaction was stopped by addition of 5 μl 2% formic acid (v/v) in ACN. AQUA peptides (Stock solution: 5.8 μg/ml, 1:100 dilution, v/v) were added immediately after the reaction was stopped.

Method Validations:

The assay was fully validated according to the U.S. Food and Drug Administration (FDA) Bioanalytical method validation guideline (www.fda.dov/downloads/Drugs/GuidanceComplianceRegulatoryInformation/Guidances/UCM070107). Nine calibration standards of trypsin-digested recombinant HSP27 were prepared by serial dilution in concentrations of 1000; 500; 250; 125; 62.5; 31.25; 15.625; 7.8 and 0 ng/ml. The limit of detection (LOD) was calculated as the smallest detectable peak above baseline noise (signal-to-noise ratio>3:1). Calculating target peptide: AQUA peptide ratios of the peak area for each concentration level. Standard curves were constructed by linear regression analysis by excel. The same samples were analyzed 7 times and the repeatability was compared. Extraction efficiency and recovery were performed by comparing concentrations between samples without and with standard rHSP27. Matrix effect was assessed using double dilution test for the linearity when serum samples were 1, 2, 4 and 8 times diluted. Parallelism test was also applied to estimate matrix effect. Stability of HSP27 in human serum was estimated for 21 days at −20° C.

Data Analysis:

Data processing was performed with Skyline software to obtain relative transition ions intensity ratios (unlabeled peptide/AQUA peptide). Standard curves with known different concentrations of trypsin digested rHsp27 and stable AQUA peptide were constructed by linear regression fit from 1000 ng/ml to 7.8 ng/ml HSP27. The tested HSP27 concentration in human serum with same quantity AQUA peptide was directly back-calculated from the calibration line.

RESULTS

Assessment of a Commercial ELISA Kit for a Serum HSP27 Assay

A commercial ELISA kit (Abcam) was validated by a standard HSP27 recovery and double dilution test. Less than 40% and 20% recoveries were found when spiking 10 ng/ml HSP27 to these two human serum samples (FIG. 1). FIG. 2A and FIG. 2B are charts showing the results of double dilution analyses with a commercial ELISA test kit wherein FIG. 2A shows the results with a first serum sample and FIG. 2B shows the results with a second serum sample. The unexpected increase of tested HSP27 values in the dilution test indicated HSP27 was complexed in serum samples (FIG. 2A, FIG. 2B). The data in FIG. 5A-FIG. 5E indicated no recovery was found when spiking 4 ng/ml HSP27 to representative both human serum samples, HSP27 is an autoantigen and induces B-cell and T-cell immunological responses of the host, and anti-Hsp27 AAbs are considered to be natural autoantibodies in the human vascular systems. Accordingly, it is likely that HSP27 in serum was associated with its anti-HSP27 AAbs thereby causing the confounding results observed with the ELISA assay.

Figure 4A:
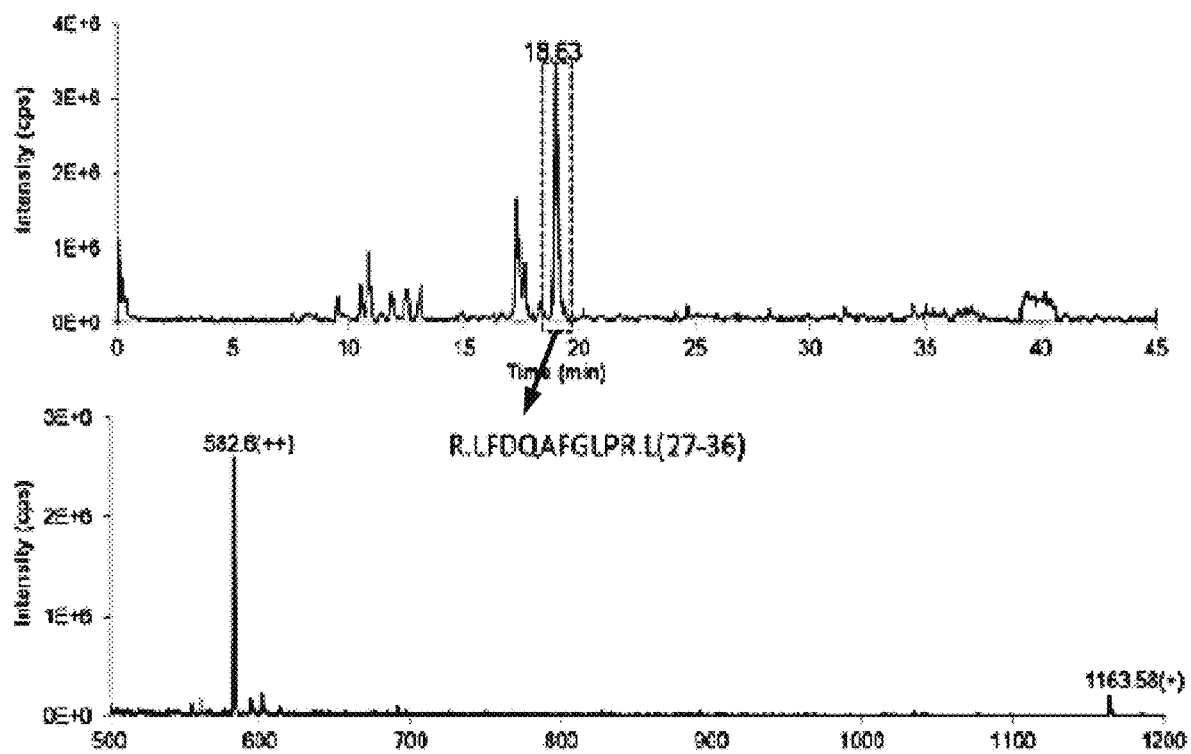
Figure 4B:
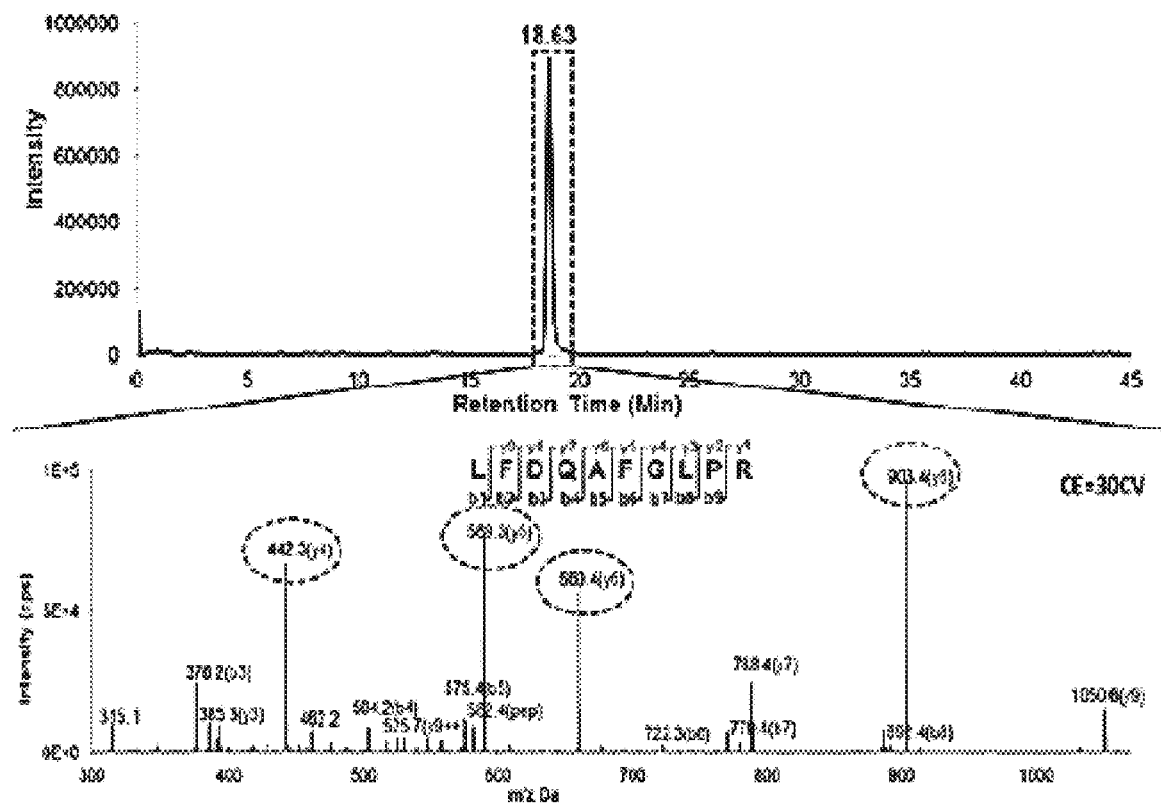

Peptide Selection:

The detection of an endogenous HSP27 tryptic peptide by MRM-MS required the establishment of a unique peptide MRM signature based on its reversed-phase retention time and MRM spectrum. Enhanced Mass Spectrum (EMS) mode was used for the preliminary screening for trypsin digested recombinant HSP27 peptides (FIG. 3A, FIG. 3B). The peak with MS of 582.6 (++), which had the highest intensity, was selected for further analysis. Enhanced ion product (EPI) analysis of ion m/z=582.6 indicated the sequences of this ion was LFDQAFGLPR (SEQ ID NO: 4) (FIG. 4B). Four transitions of this precursor peptide, 582.6>903.4, 582.6>660.4, 582.6>589.3 and 582.6>442.3 were finally selected to set up MRM method to screen whether this peptide was also available in human serum.

Protein G beads was applied to pull down HSP27-autoantibody complex (FIG. 3B). MRM of both protein G beads fraction and flow through fraction indicated that HSP27 was located in protein G beads fraction only, but not in the flow through (FIG. 5A), indicating HSP27 was not only existed but all associated with its autoantibody in serum. Further uniqueness analysis was applied by SRMCollider (http://www.srmcollider.org/srmcollider/srmcollider.py), a program that will take our selected transitions and compare them to all other transitions in human proteome and find whether interferences occurred. Selected transitions 582.6>903.4+660.4+589.3+442.3 are unique in human proteome database (FIG. 6).

Exome variant analysis was done by Exome Variant Server (http://evs.gs.washington.edu/EVS/), which indicated selected peptide LFDQAFGLPR (S) had two possible mutations, R26P and R36Q, which will affect the production of selected endogenous peptide, while both mutants are at very low ratio (1 of 4011 in European American (EA) and 1 of 1993 for African American (AA) for R26P; 0 of 3983 in EA and 1 of 2002 in AA), which indicates less than 0.1% samples would have possible interferences by these two mutations.

Figure 4C:
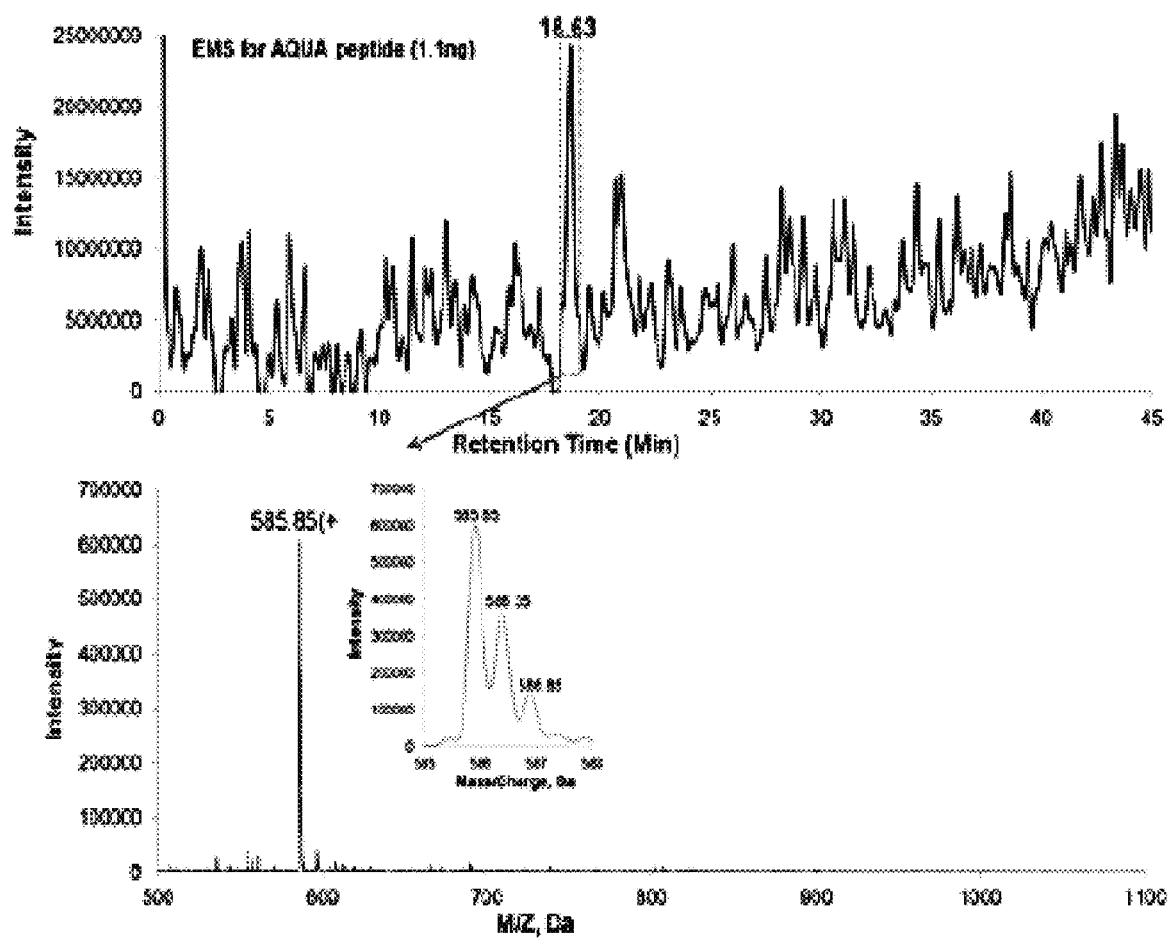
Figure 4D:
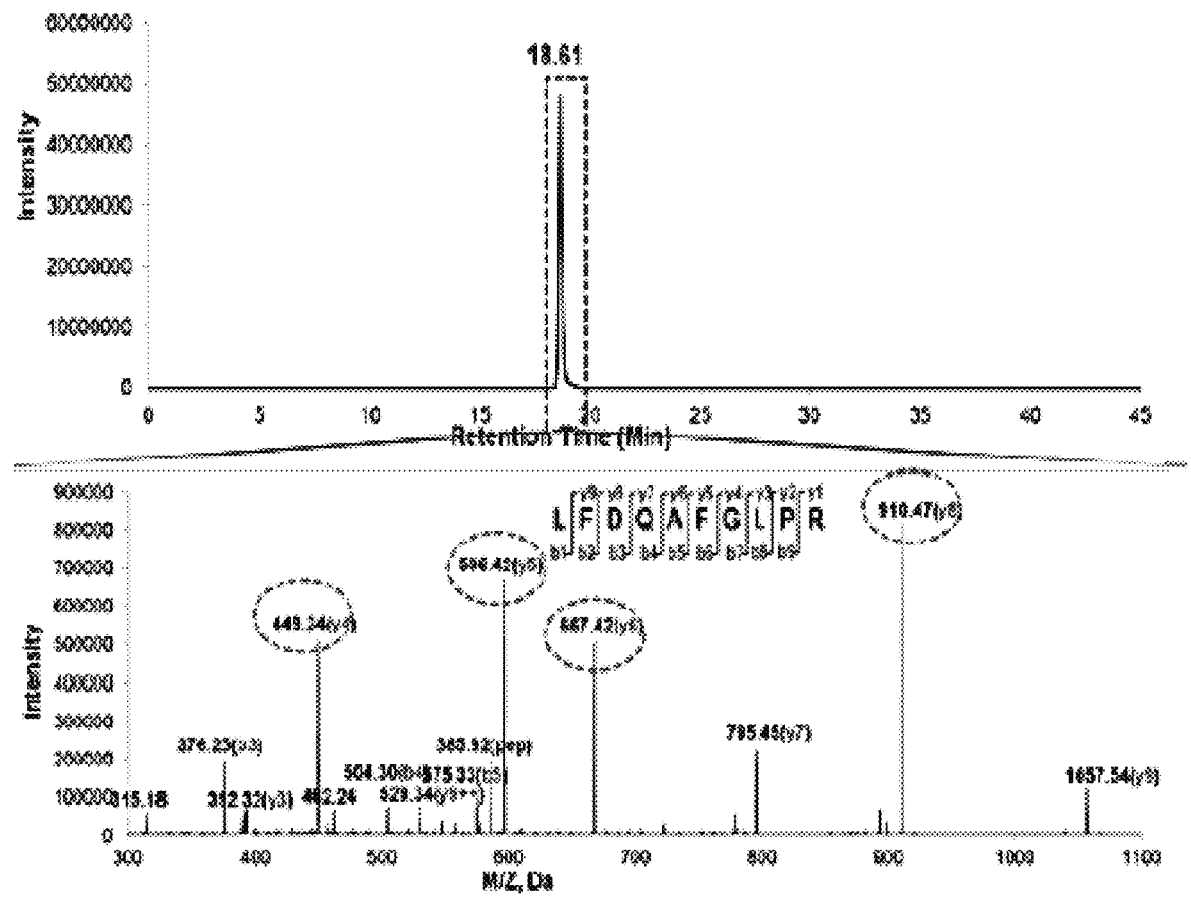

AQUA peptide LFDQAFGL(13C6 15N)PR was finally synthesized as the future internal references. EMS of this AQUA peptide indicated its m/z value was 585.9 with double charged and the retention time (18.6 min) was as same as the selected light peptide from recombinant HSP27 (FIG. 4C), further supporting our former conclusion. Transitions of 585.9>910.4+667.4+596.4+449.3 from EPI of this AQUA peptide (FIG. 4D) were finally selected for the quantification of HSP27.

Standard Curves for Establishment and Quantification of Endogenous HSP27 in Patients' Serum:

Using established MRM, a range of concentrations of trypsin-digested recombinant HSP27 peptides were mixed with a fixed concentration of AQUA peptide (58 ng/ml) in 0.1 formic acid and 5% ACN. The observed peaks area ratios for 4 selected transitions (y8, y6, y5 and y4) were subsequently plotted against the known recombinant HSP27 concentrations. An excellent linear correction was established ($R2=0.9981$) with linear equator of $y=0.0006028x+0.0009$ where y is the ratio of 4 transitions area and x (ng/ml) is the real concentration of trypsin digested recombinant HSP27 (FIG. 5B), which demonstrated that AQUA peptide would serve as a suitable internal standard for the detection of the corresponding endogenous HSP27 in patient serum.

Figure 5:
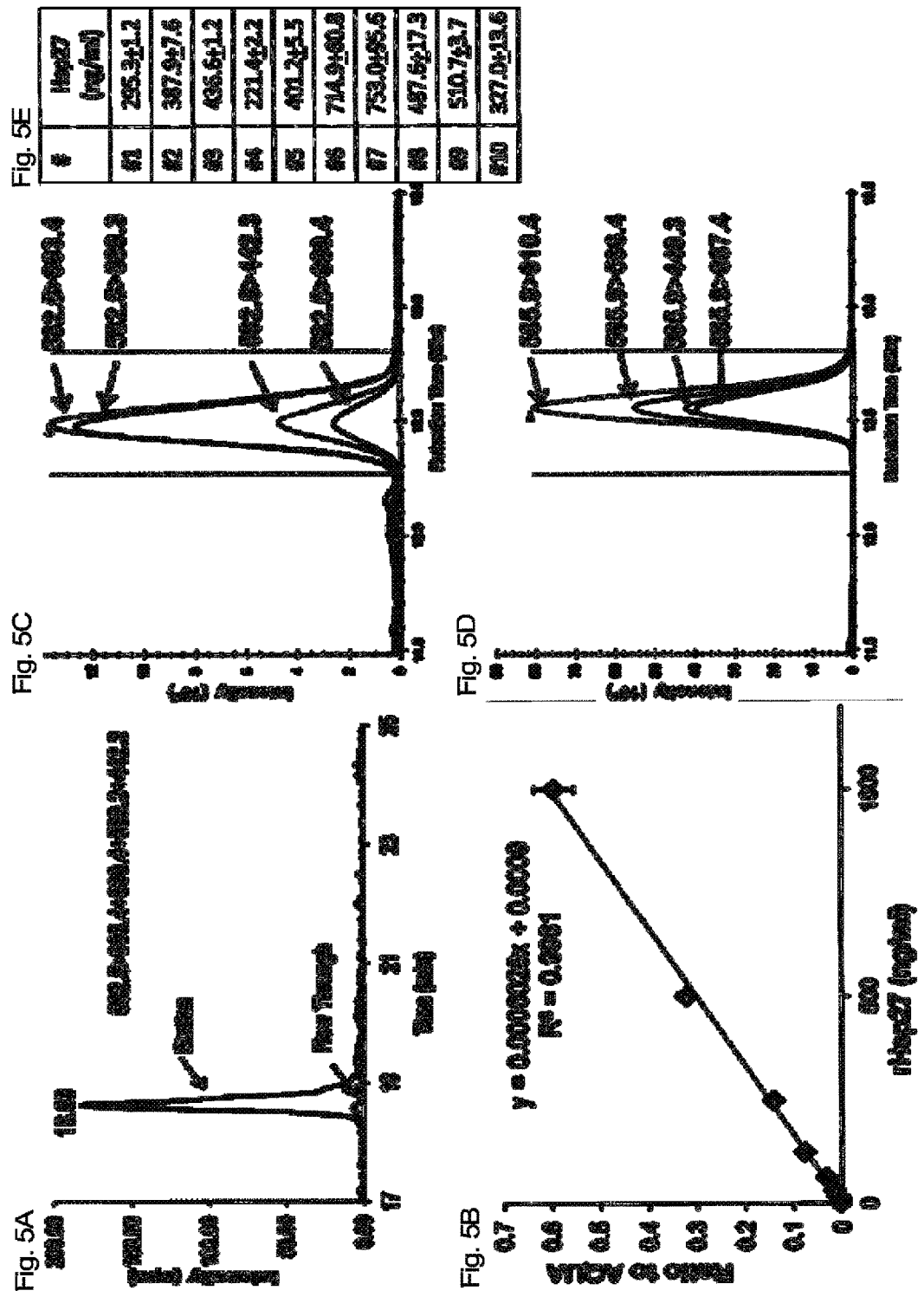

The ratio of 4 selected transition ions derived from the endogenous peptide from trypsin digested HSP27 and spiked same amount isotope-labeled peptides provided a quantitative measure of HSP27 in human serum samples based on the standard curves above. FIG. 5C) shows one example result of human serum HSP27 assay using Skyline software, which was used to calculate the ratio of 4 transition ion. HSP27 level in human serum using MRM-MS method are among hundreds ng per ml range (10 human serum samples data was listed in FIG. 5D). The level of HSP27 in human serum tested by MRM-MS is much higher (~100 times) than the reported value by commercial ELISA kit. As indicated above, antibody-antigen based ELISA was biased by the association of HSP27 with its autoantibody. MRM-MS may give HSP27 level close to its real value.

Figure 7:
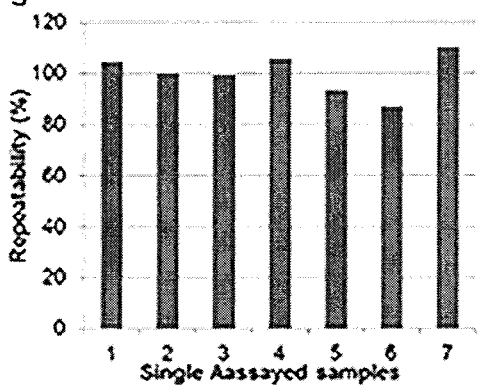
Figure 7:
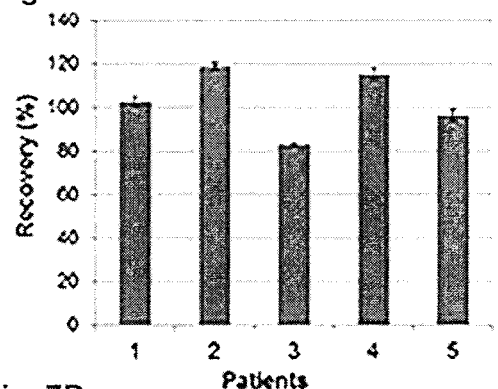
Figure 7:
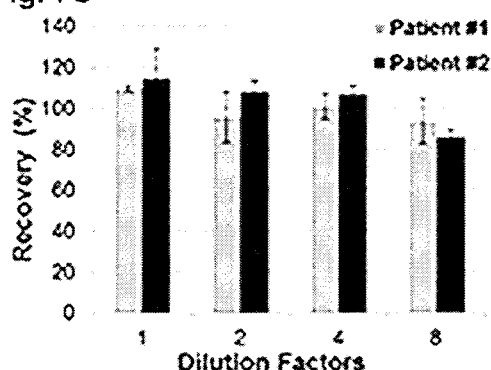
Figure 7:
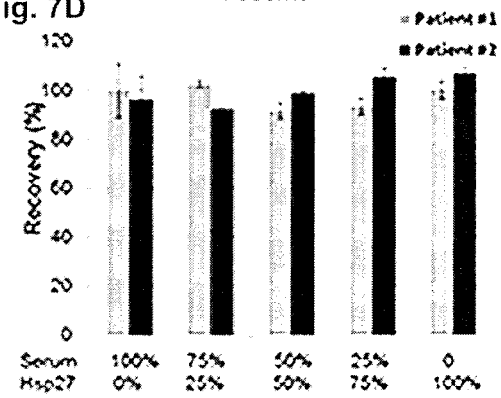
Figure 7:
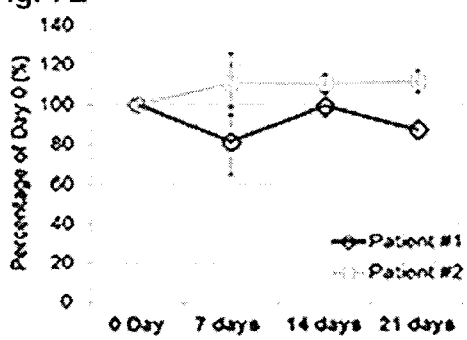

Validations of MRM Method to Test HSP27 in Serum:

The assay was fully validated according to the U.S. Food and Drug Administration (FDA) Bioanalytical method validation guideline (www.fda.gov/downloads/Drugs/GuidanceComplianceRegulatoryInformation/Guidances/UCM070107). Repeatability of established MRM-MS method was analyzed for one serum sample with 7 independent treatment and assay. FIG. 7A shows that a good repeatability between 80% to 120% was achieved with the setup MRM-MS.

A recovery test was run after spiking 100 ng/ml trypsin-digested standard HSP27 to human sera and 5 individual sera was tested with recovery between 80% to 120% (FIG. 7B). Double dilution assay of 2 representative sera also indicated good linear relationship with R2 (n=3) of 0.9958 and 0.9988 respectively (FIG. 7C). Parallelism test after different ratio mix between known endogenous HSP27 serum and the same concentration of rHSP27 (0% serum+100% rHsp27, 25% Serum+75% rHsp27, 50% serum+50% rHsp27, 75% serum+25% rHsp27 and 100% serum+0% rHsp27) was shown in FIG. 7D). The final total HSP27 levels tested by established MRM-MS were varied between 90% to 110%. The stability assay of HSP27 in serum samples was estimated using two representative sera with 3 weeks length. Serum samples were divided to different aliquots to test the stability of HSP27 after different time of storage at −20° C. After 3 weeks storage, endogenous HSP27 from both sera were 111+6% and 87+5% of fresh sera after collection, respectively (FIG. 7E).

DISCUSSION

In the clinical chemical laboratories, there are increasing interests to test Hsp27 levels in human fluid samples, since from its foe side, high level of HSP27 has anti-apoptosis role and resists chemotherapy of drugs for cancer cells apoptosis (Hsu et al., 2011, Chemoresistance of lung cancer stemlike cells depends on activation of Hsp27. Cancer 117(7):1516-1528), and from its friendly side, High Hsp27 levels are anti-inflammatory and associated with less risk to have a myocardial infarction, stroke or cardiovascular death (Seibert et al., 2013, Serum heat shock protein 27 levels represent a potential therapeutic target for atherosclerosis: observations from a human cohort and treatment of female mice. J. Am. Coll. Cardiol. 62(16):1446-1454).

Hsp27 serum level was first reported in 2004 using standard ELISA method with mouse anti-Hsp27 monoclonal antibody as capture antibody and rabbit anti-Hsp27 polyclonal antibody as the primary antibody (De et al., 2004, Detection of the soluble heat shock protein 27 (hsp27) in human serum by an ELISA. J. Immunoassay Immunochem. 25(2):159-170). It was reported that the median Hsp27 of 28 serum samples was 3.27 ng/ml, while 10 serum samples were not detectable for their HSP27 level in serum. Zimmermann et al., (2014) measured HSP27 serum concentrations in 40 NSCLC cases and 40 healthy controls by different ELISA kits from R&D, Enzo Life Sciences, Invitrogen, Abcam, and MyBioSource, and found that obtained HSP27 levels by the different assays had up to 10-fold differences of serum concentrations with correlation coefficients of pair-wise assay comparisons that ranged from 0.184-0.938. They finally concluded these ELISA kit couldn't be used for diagnosis purpose in lung cancer and possibly in other diseases too (Zimmermann et al., 2014).

Usually sandwich ELISA is applied in antigen tests in which captured antibodies are coated to capture antigen in the samples, and the primary antibody is used to bind the captured antigen. While HSP27 is naturally associated with its auto-antibodies (FIG. 4B), and antibody-antigen interaction based ELISA will be definitely affected by the natural complex of Hsp27-autoantibody, which will bias the real value of HSP27 in the samples (FIGS. 1, 2) and can't be applied for diagnostic use in the presence of anti-HSP27 AAbs.

Disclosed herein is a MRM-MS method for quantification of HSP27 levels in human serum. MRM (also referred to as "Selected Reaction Monitoring"—SRM) is a method based on tandem mass spectrometry, particularly on triple quadrupole mass spectrometers, in which an ion of a particular mass is isolated by mass-resolving Q1, the selected ion product is fragmented in Q2 collision cells and the fragments is detected in Q3, which is particularly useful when predetermined sets of proteins, such as candidate biomarkers, need to be measured across multiple samples in a consistent, reproducible and quantitatively precise manner. Based on MRM-MS techniques, recombinant HSP27 was trypsin-digested and their fragment precursor peptides were screened by Enhanced Mass Spectrum mode (EMS). The selected precursor peptide LFDQAFGLPR (SEQ ID NO: 6) fragments were determined by Enhanced Product Ion mode (EPI). Final 4 transitions of this precursor (582.6>903.4+ 660.4+589.3+442.3) was confirmed by uniqueness and Exome variations, using SRMCollider and Exome Variant Server (FIG. 4A, FIG. 4B). MRM-MS method per se is not a quantitative technique, and the most popular used approach relies on the gold standard, isotopically labeled reference peptides that are chemically identical to the light native peptides (AQUA peptides), for absolute quantification. The synthesized AQUA peptide LFDQAFGL(13C6 15N)PR (transitions of 585.9>910.4+667.4+596.4+449.3) from EPI of this AQUA peptide (FIG. 4C, FIG. 4D) were applied as the gold standard in the assay.

The present MRM-MS method exploits the characteristics of HSP27 association with its anti-HSP27 AAbs, and precipitates HSP27 by pulling down whole IgG using Protein A magnet beads to enrich HSP27 (FIG. 3, FIG. 5A). At the same time, other abundant proteins were removed from serum/plasma. This high-throughput purification method can be also applied to other biomarkers, which have abundant antibodies in serum/plasma.

Validation of an established method is a critical step to get high-confident and high-quality research data necessary to answer the studied questions. Typically, validation takes into account the criteria such as linearity, accuracy, sensitivity, specificity, reproducibility, range of use, limit of detection and variability et al. The reproducibility of the sample preparation and assay methods and observed a CV of 7.76% (n=7) is shown in FIG. 7A. The stability of HSP27 stored at −20° C. is shown in FIG. 7E.

Quantitative linearity of the MRM-MS method using both recombinant standards (FIG. 5B) indicates the linearity of the assay can be reached between 1000 ng/ml and 7.8 ng/ml with LOQ<=7.8 ng/ml. No wider range was probed since the human serum HSP27 levels are among the linear ranges (FIG. 5D). Double dilution test of representative sera also indicated linearity of the MRM-MS method (FIG. 7C), indicating the good quantitative linearity of established MRM-MS method. Parallelism test (FIG. 7D) was also applied for the specificity studies to test the medium complexity, indicating good specificity of the method.

In summary, a novel MRM-MS based method was developed for the quantitation of a heat shock protein HSP27 in human serum. The double charged peptide LFDQAFGLPR (SEQ ID NO: 4) and its transition ions (y8+y6+y5+y4) enabled accurate quantification of HSP27 in serum samples. In this method, a simple HSP27 precipitation by pulling down HSP27-autoantibody complex using protein G magnet beads for trypsin digestion followed by a gradient HPLC with MRM-MS detection offered sufficient quantification and selectivity for analysis of clinical samples.

Example 2: Reduction of PCSK9 Expression with HSP27 and Anti-HSP27 AAbs

HepG2 liver cells ($0.5 \times 10^6$ cells/60 mm well) were incubated on H-Glucose DMEM medium containing 10% FBS and 1×penicillin/streptomycin in the presence or absence of rHsp27 (200 µg) for specified time periods at 37° C. At the end of incubation period, the medium was removed and centrifuged at 4,000 rpm for 10 min at 4° C. to remove a small amount of residual cells and debris. The supernatant fraction was stored at 4° C. until analyzed.

Figure 8:
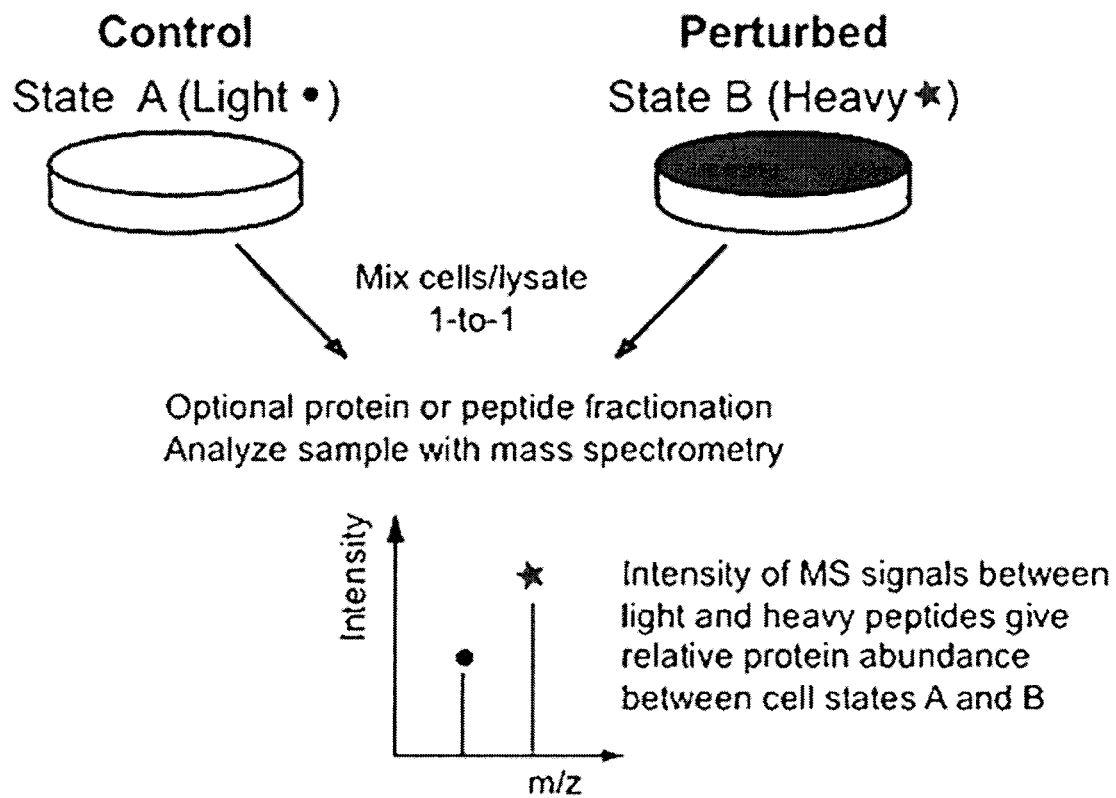
FIG. 8 is a flowchart illustrating a SILAC-MS method disclosed herein.

A first subset of the cultured HepG2 liver cells were treated with 100 µg/mL of HSP27 for 24 h. A second subset of the cultured HepG2 liver cells were treated for 24 h with a mixture of 1 µg/mL of HSP27 plus 5 µg/mL of anti-HSP27 AAbs. The cells were then lysed and their protein/peptide contents were separated, quantified and assessed using a SILAC-MS method disclosed by Oda et al. (Accurate quantitation of protein expression and site-specific phosphorylation. Proc. Natl. Acad. Sci. USA 96(12):6591-6) and outlined in FIG. 8 (SILAC is an acronym for "stable isotope labelling using amino acids in cell culture"; MMS is an acronym for mass mass spectrometry).

The data in FIG. 9A show that the HSP27 treatment significantly reduced the levels of PCSK9 while concurrently significantly increasing the levels of LDLR. The data in FIG. 9B show that treatment with the mixture of HSP27 plus anti-HSP27 AAbs treatment had even a greater effect on significantly reducing the levels of PCSK9 while concurrently significantly increasing the levels of LDLR.

Example 3: Reduction of PCSK9 Expression with HSP27

The hypothesis tested in this example was that HSP27 augments hepatic LDL-C uptake via reductions in PCSK9 levels and therefore, preserves LDL-R cell surface recycling. This hypothesis was tested in vitro by examining the expression of PCSK9 mRNA and protein in HepG2 liver cells. As well, atherosclerosis-prone apoE$^{-/-}$ mice treated were with a recombinant HPS27 protein referred to herein as "rHSP27" and its effect on the abundance of PCSK9 in the liver and serum were examined.

Reagents:

DMEM, trypsin EDTA, PBS and FBS were purchased from Gibco (a subsidiary of ThermoFisher Scientific, Grand Island, N.Y., USA). Disposable culture dishes were purchased from Greiner Bio-One North America (Monroe, N.C., USA). Filters were purchased from Millipore (Billerica, Mass., USA). Molecular weight protein standards and ECL were purchased from Life Technologies Inc. (Grand Island, N.Y., USA). SDS, TEMED, ammonium persulfate, Tris, NaCl, PMSF, paraformaldehyde and organic solvents were purchased from Sigma Aldrich (St. Louis, Mo., USA). Acrylamide solution (30% T, 2.6% C) was purchased from National Diagnostics (Atlanta, Ga., USA). TLC silica gel 60 plates were purchased from General GlassBlowing Company, Inc. (Richmond, Calif., USA). Lipid standards were purchased from Avanti Polar Lipids, Inc. (Alabaster, Ala., USA).

The following antibodies were used for the western blot analysis: rabbit polyclonal anti-PCSK9 (H-160), rabbit polyclonal anti-LDLR (H-120), rabbit polyclonal anti-HMGCR (H-300), rabbit polyclonal anti-SREBP-2 (H-164), Mouse Monoclonal anti β-Actin (9), all purchased from Santa Cruz Biotechnology Inc. (Dallas, Tex., USA), anti-mouse, anti-goat and anti-rabbit peroxidase-conjugated secondary antibodies, all purchased from Abcam Inc. (Cambridge, Mass., USA).

Production of Recombinant HSP27:

Recombinant HSP27 (rHSP27; SEQ ID NO: 2), rHSP25 (SEQ ID NO: 1) and rHSP27-C1 (SEQ ID NO: 5) (the truncated C-terminus form of the full length HSP27 peptide) were produced following the methods taught by Seibert et al. (2013, Serum heat shock protein 27 levels represent a potential therapeutic target for atherosclerosis: observations from a human cohort and treatment of female mice. J. Am. Coll. Cardiol. 62(16):1446-54).

HepG2 Cell Culture Sample Preparation:

HepG2 cells ($0.5 \times 10^6$ cells/60 mm well) were incubated on H-Glucose DMEM medium containing 10% FBS and 1×penicillin/streptomycin in the presence or absence of rHsp27 (200 µg) for specified time periods at 37° C. At the end of incubation period, the medium was removed and centrifuged at 4,000 rpm for 10 min at 4° C. to remove a small amount of residual cells and debris. The supernatant fraction was stored at 4° C. until analyzed.

Meanwhile, cells were washed three times with cold PBS, scraped off the dishes (after the addition of 1 ml lysis buffer (20 mM Tris-HCl; pH 8.0; 150 mM NaCl; 0.1 mM PMSF), and sonicated; whole cell lysates were then stored at −20° C. until use.

LDL-Receptor Immunolabelling:

HepG2 cells ($10^5$ cells) were seeded in SPL Coverglass sterile dish 35×10 mm (Bio Lab) for 2 days. Cells were then treated with 17β-estradiol (100 nM) or rHSP27 (100 µg) overnight (16 hours). After washing, cells were fixed in 4% paraformaldehyde, permeabilized in 0.5% (v/v) Triton x-100 for 10 minutes, washed, blocked in 10% horse serum (1 hour), washed, then incubated in primary antibody rabbit monoclonal to LDL-R (Ab52818; ABCAM; 1:100) 4° C. overnight. After washing, cells were incubated in secondary antibody fluorescein goat Anti-Rabbit IgG antibody (FI-1000; Vector Laboratories; 1:100) for 30 min at room temperature, then mounted with mounting medium with DAPI (VectaShield Antifade Mounting Medium with DAPI; Vector Labs H-1200) for at least 24 hour in the dark before visualization. Various controls were used, and included: (i) absence of the Triton treatement, and (ii) omitting the primary or secondary antibodies used for immunolabelling.

Lipids Analyses:

For in vivo studies, plasma total cholesterol levels were determined by using an enzymatic test kit (Wako Pure Chemical Industries, Ltd; Osaka, Japan). Fast Protein Liquid Chromatography (FPLC) was used to analyze lipid subfractions. Briefly, the lipoproteins of mice sera were separated by size exclusion chromatography in AKTAPRIME® Plus fast protein liquid chromatography system (AKTAPRIME is a registered trademark of GE Healthcare Bio-Sciences AB, Uppsala, Sweden) with Superose® 6 10/30 GL Column (SUPEROSE is a registered trademark of GE Healthcare Bio-Sciences AB). 200-ul samples were loaded to columns and eluted with 0.2 ml/min PBS. The absorptions were monitored at 280 nm. 0.5 ml was collected from each sample for the analysis of cholesterol. The mix of blue dextran (2000 kD), apoferritin (443 kD), alcohol dehydrogenase from yeast (150 kD) and albumin, bovine serum (66 kD) (Sigma-Aldrich, Oakville, ON) were applied as the standards.

Protein Analysis:

Total cell or tissue lysates were prepared in lysis buffer (20 mM Tris-Hcl pH8.0, 150 mM NaCl, 0.1% SDS, 0.1 mM PMSF). Lysates were cleared by centrifugation at 4° C., 12,000 rpm for 10 min, and protein concentrations were determined using the Bradford protein assay with BSA as the standard. Samples (30 µl culture medium, 50 µg for cell and 25 µg for liver) were separated by SDS-PAGE under reducing conditions, transferred to IMMOBILON® PVDF (IMMOBILON is a registered trademark of Millipore Corp.) using IBLOT® Dry Blotting System (Life Technologies; IBLOT is a registered trademark of Invitrogen Corp., Carlsbad, Calif., USA) and subsequently membranes were immunoblotted with the following antibodies: LDL-R (Santa Cruz, 1:1000) and PCSK9 (Santa Cruz, 1:1000); β-Actin (Santa Cruz, 1:1000) was used as the loading control. Appropriate secondary HRP-conjugated antibodies were used prior to visualization by enhanced chemiluminescence (ECL, Life technologies).

PCSK9 ELISA:

Plasma PCSK9 levels were measured using ELISA kits specific to mouse PCSK9 (DY3985; R&D Systems, Inc., Minneapolis, Minn., USA) following the manufacturer's instructions.

HSP27 Polyclonal Antibody Preparation

A rabbit polyclonal antibody (Pab) mimicking human HSP27 autoantibody was produced according to standard procedures by Cedarlane Laboratories, LTD (Burlington, ON) and in accordance with the requirements of the Canadian Council on Animal Care. Briefly, two rabbits were injected with 0.2 mg of rHSP27. After 28, 48 and 66 days the rabbits were boosted using 0.2 mg rHSP27 to increase the quantity of the resulting Pab. Rabbit sera was collected on day 78. The immunization efficiency was determined by an indirect ELISA coating the plates with rHSP27. The final serum was loaded to a 5 ml Protein G affinity column (GE Healthcare) for IgG affinity purification. After a 100 ml buffer A (50 mM PBS buffer containing 200 mM NaCl) wash, the antibody was eluted by buffer B (20 ml 20 mM sodium acetate, pH=2.5) and immediately neutralized by buffer C (400 mM PBS, pH=8.0). The antibody solution was then concentrated using a 15 ml of 30 kDa molecular weight cutoff filter (Millipore, Etobicoke, ON) and the buffer exchanged with buffer A for future usage. Two milligrams of biotinylated rHSP27 was then applied to a 1 ml streptavidin affinity column (GE Healthcare) for antigen affinity purification. The antigen conjugated column was washed with 20 ml Buffer A, loaded with Pab from the Protein G purification step and incubated for 5-10 min at 4° C. before washing twice with 20 ml buffer A. The antigen-specific Pab was then eluted with buffer B and immediately neutralized by buffer C to pH ~7.0. The final purified HSP27 specific Pab was buffer exchanged with DPBS buffer and filtered through 0.2 µm filter for future usage.

Fast Protein Liquid Chromatography (FPLC)

The molecular size of the HSP27 Pab complex was determined by size exclusion chromatography in an AKTA Primer Plus fast protein liquid chromatography (FPLC) system (GE Healthcare) with Superose® 6 10/30 GL Column (GE Healthcare). Samples were diluted in PBS to 20 ug/ml and the prepared Pab was mixed with rHSP27 (or rC1 as a control) in different ratios for 30 minutes. Final samples (0.2 ml) were loaded to columns and the fractions were eluted with 0.2 ml/min PBS buffer and the absorptions were monitored at 280 nm. The mix of Blue Dextran (2000 kD), Apoferritin (443 kD), Alcohol Dehydrogenase from yeast (ADH; 150 kD) and bovine serum albumin (66 kD) (Sigma- Aldrich Canada) were applied as protein standards. The protein standards were sourced from Sigma-Aldrich Canada (Oakville, ON, CA)

Western Blotting

HepG2 cells in the 6-well plates were washed twice with phosphate-buffered saline and lifted by pipette with 1 ml PBS. Cells were sonicated and then centrifuged at 20,000×g for 2 hours to get the membrane fraction. The membrane fraction was re-suspended in PBS by sonication and the protein concentration was determined by Bradford reagent (Sigma). 50 µg whole protein was loaded onto a 10% SDS-PAGE gel and separated at 120V using gel electrophoresis. Protein was then transferred to a PVDF membrane by iBlot® dry blotting system (Life Technologies, NY). Membranes were then subjected to western blotting using the following antibodies: (i) anti-HSP27, and (ii) anti-PCSK9. Signals on the membrane were visualized by chemi-luminescence of HRP substrate.

Murine Atherosclerosis Model

All experimental procedures involving mice were approved by the Animal Care Committee of the University of Calgary (Calgary, AB, CA), which complies with Canadian guidelines for experiments involving animals. Recombinant HSP27 (rHSP27, 100 µg) or PBS was administered by subcutaneous injections to male and female ApoE−/− mice. Adjuvant was added to these subcutaneous injections to stimulate anti-HSP27 auto-antibodies that facilitate the biological effect of HSP27 following the method taught by Shi et al. (2014, *When Auto-Antibodies Potentiate: The Paradoxical Signalling Role of Anti-HSP27 Auto-Antibody Immune Complexes Improves Athero-Protection*. Circulation: A12771). Mice were maintained on a high-fat diet (HFD, 1.25% cholesterol, 15.8% fat; Harlan Teklad, Madison, Wis.) until euthanasia when blood samples were collected. At time of euthanasia, fasting mice were anaesthetized under isoflurane, and liver and whole blood was collected via cardiac puncture before systemically perfusing the mice via the left ventricle with phosphate-buffered saline (PBS) followed by 4% paraformaldehyde (PFA) in PBS, before the heart and aorta were removed and immersed in 4% PFA/PBS at 4° C. overnight.

Evaluation of "En Face" Atherosclerotic Lesion Area:

The aorta was dissected from the ascending to the thoracic segments, and after removing the adventitia, pinned and photographed for visualization of lesion burden. Thereafter, the aorta was opened longitudinally, with the primary incision following the lesser curvature of the arch. To obtain a flat preparation for imaging, a second incision was made along the greater curvature of the arch down to the level of the left subclavian artery. Lipid-rich intraluminal lesions were stained with oil red O and photographed following the procedures disclosed by Raizman et al. (2013, Heat shock protein-27 attenuates foam cell formation and atherogenesis by down-regulating scavenger receptor-A expression via NF-kappaB signaling. Biochim. Biophys. Acta. 1831(12): 1721-8). The en face atherosclerotic aortic lesions were analyzed by two independent observers blinded to the treatment status of the mice using Image-Pro software (Media Cybernetics, Silver Spring, Md.). The extent of atherosclerosis was expressed as the percentage of surface area of the entire aorta covered by lesions.

Preparation of Aortic Sinus and Evaluation of Atherosclerotic Lesion Area:

The top half of the heart containing the aortic root was embedded in paraffin or frozen in TISSUE-TEK® O.C.T. media (Sakura FineTek; Torrance, Calif., USA; TISSUE-TEK is a registered trademark of Sakura Finetek Japan Kabushiki Kauisha Corp., Tokyo, Japan). Serial 4-µm sections of the aortic sinus including the aortic valve leaflets were sectioned, beginning at the level where the aortic valve first appears, and stained with oil red O and photographed following the procedures disclosed by Rayner et al. (2008, Extracellular release of the atheroprotective heat shock protein 27 is mediated by estrogen and competitively inhibits acLDL binding to scavenger receptor-A. Circulation Res. 103(2):133-141).

Immunofluorescence $10^5$ cells were seeded ina SPL coverglass sterile dish 35×10 mm (Bio Lab) for 2 days. The cells were then treated with 17 β-estradiol (100 nM) or rHSP27 (100 µg) overnight (16 hours). After washing, the cells were fixed in 4% paraformaldehyde. Fixed cells were permeabilized with 0.5% (v/v) Triton x-100 for 10 minutes, washed and then blocked in 10% horse serum for 1 hour, washed again, and then incubated overnight at 4° C. in primary antibody with rabbit monoclonal to LDL-R (ABCAM; 1:100) and Fluorescein goat Anti-Rabbit IgG antibody (FI-1000; Vector Laboratories; 1:100) for 30 min at room temperature. Mounted with mounting medium with DAPI (VectaShield Antifade Mounting Medium with DAPI; Vector Labs H-1200) for at least 24 hour in the dark before visualization with fluorescence microscopy.

Statistical Analysis

All data represent mean±SEM. Each experiment was conducted at least 3 times. Statistical analyses were performed using t-tests and differences were considered significant at P-value<0.05.

Results

The effects of rHSP27 treatment on PCSK9 mRNA expression in HepG2 (liver) cells as measured by quantitative RT-PCR, are shown in FIG. 10A and FIG. 10B. A treatment of 200 ug/ml rHSP27 reduced PCSK9 mRNA levels after 3 and 6 hr (FIG. 10A). Co-treatment with rHSP27 (1 ug/ml) and Pab (5 ug/ml) (dark grey bars) also reduced PCSK9 mRNA compared to the control treatment (FIG. 10B).

Figure 11:
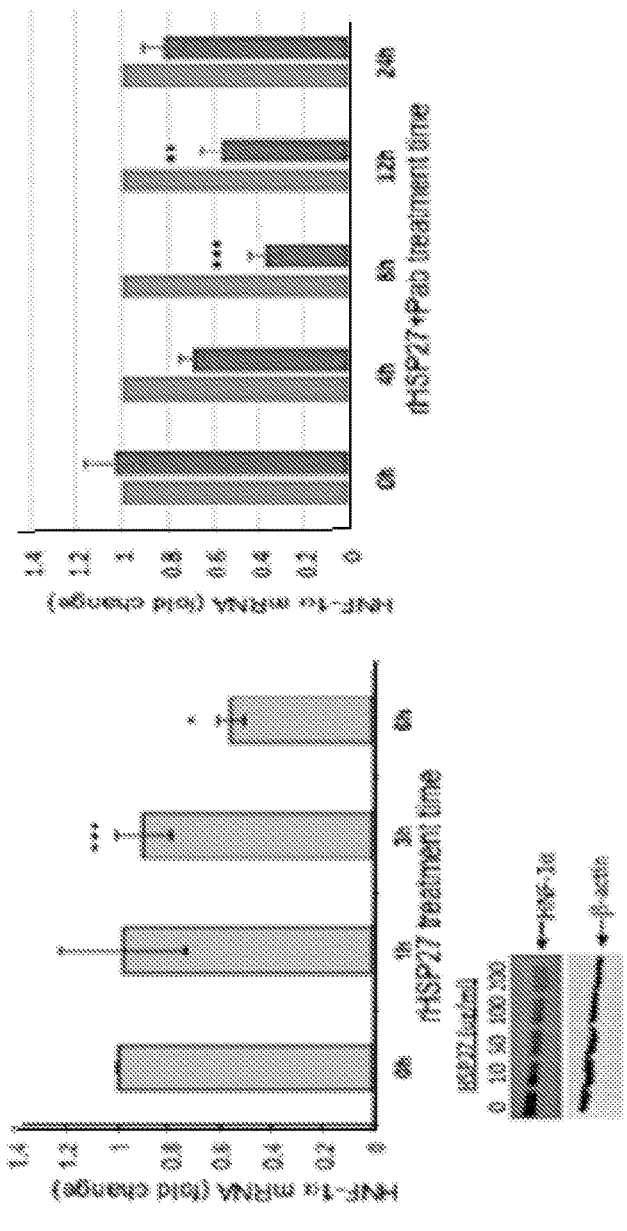
Figure 11:
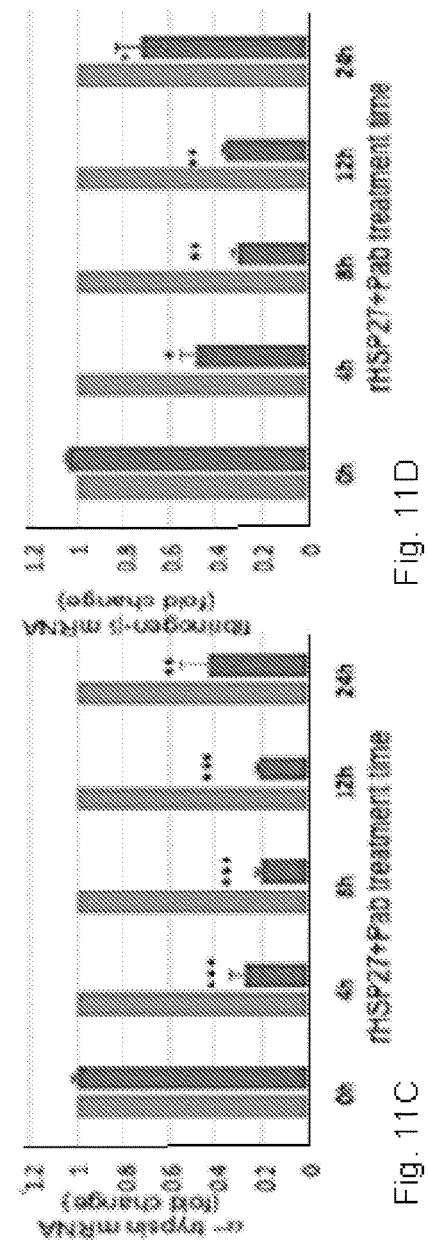

The results of quantitative RT-PCR measurement of HNF-1a regulated genes are shown in FIG. 11A FIG. 11D. Treatment with 200 ug/ml of rHSP27 reduced mRNA levels at 6 hr (FIG. 11A, top panel) and protein levels after 24 hr (bottom panel) of the PCSK9 transcription factor, HNF-1a. In addition, co-treatment with rHSP27 (1 ug/ml) and Pab (5 ug/ml) (dark grey bars) reduced HNF-1a mRNA (FIG. 11B) as well as two HNF-1a downstream target genes: α-trypsin (FIG. 11C) and fibrinogen-β (FIG. 11D) in comparison to the controls (light grey bars).

Figure 12:
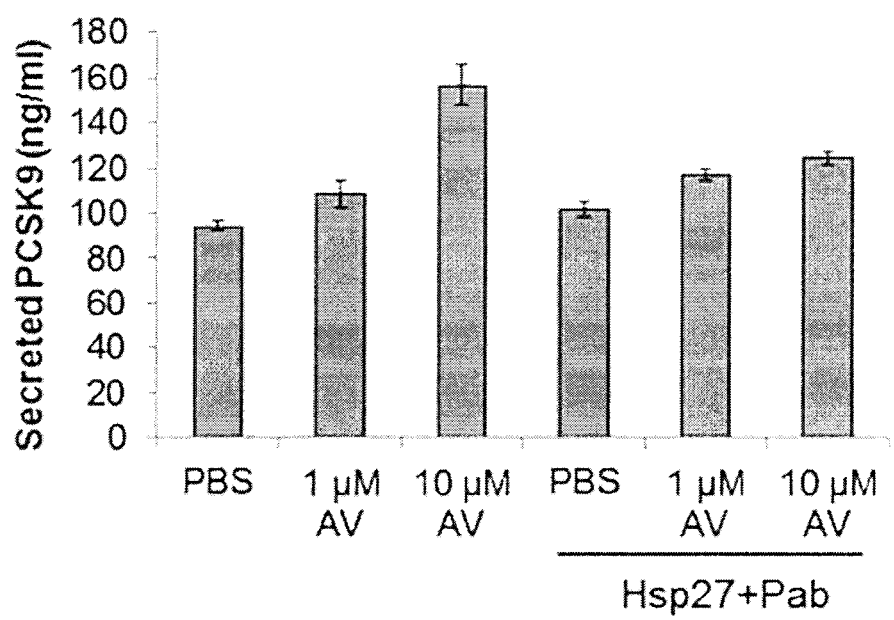
FIG. 12 is a chart showing PCSK9 secretion from HepG2 (liver) cells after treatment with Atorvastatin (AV), a HMG Co-A Reductase (HMG Co-AR) inhibitor.
Figure 13:
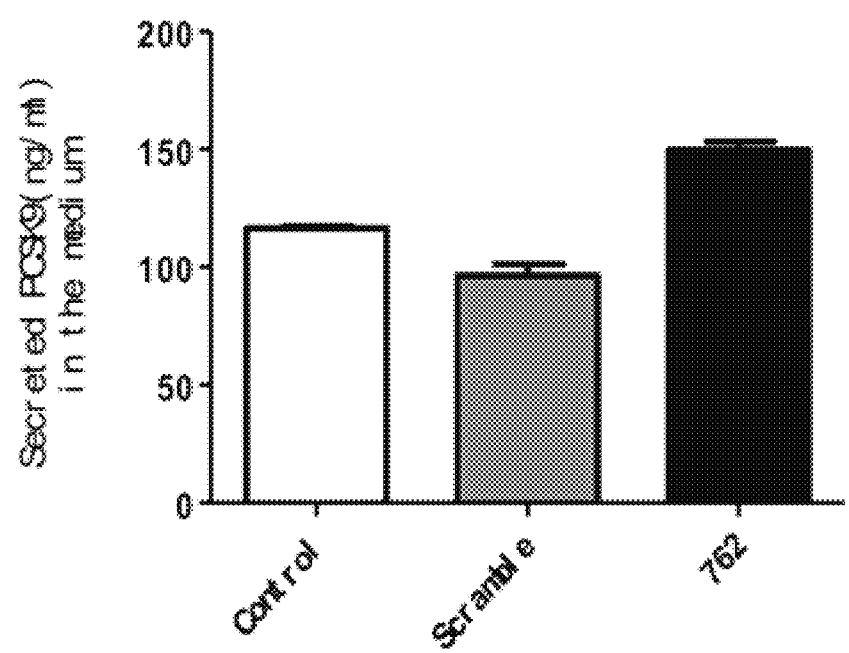
FIG. 13 is a chart showing knockdown of HSP27 expression, using silencing RNA, on PCSK9 secretion in HepG2 (liver) cells.
Figure 14:
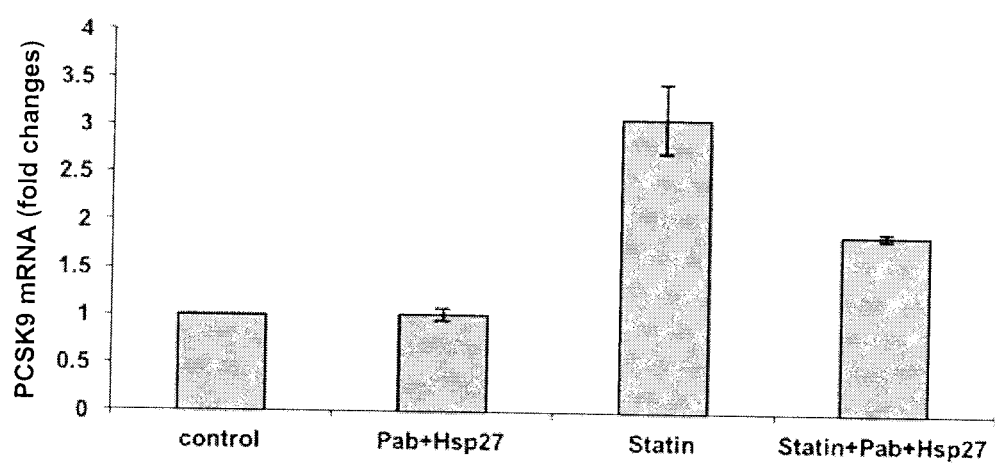
FIG. 14 is a chart showing the effects of co-treatment with rHSP27 (1 ug/ml) and Pab on statin-mediated increases in PCSK9 mRNA levels.

Atorvastatin (AV) reduces cholesterol synthesis, and therefore, intracellular cholesterol levels, which prompts the activation of the transcription factor, Sterol Regulatory Element-Binding Protein 2 (SREBP-2) that then promotes the expression of LDL-receptors and uptake of cholesterol into the cell. However, SREBP-2 is also a transcriptional regulator of PCSK9. Hence, HMG Co-AR inhibitors (or "statins") also have the undesirable effect of promoting the expression of PCSK9. The effects of adding or reducing HSP-27 levels on PCSK9 secretion were tested with increasing doses of AV. The data in FIG. 12 show that dose-dependent secretion of PCSK9 by AV was attenuated by rHSP27 plus Pab treatments. The data in FIG. 13 show that stable knockdown of HSP27 ("762" cells) increased PCSK9 secretion. The data in FIG. 14 show that while the rHSP27 plus Pab treatment did not have an effect on PCSK9 mRNA, that treatment did reverse the increase in PCSK9 expression that resulted from treatment with AV.

FIG. 15A shows Western blots and a chart (relative densitometry quantification) indicating that treating HepG2 (liver) cells for 1 h with 17 β-estradiol resulted in a 28% reduction in PCSK9 expression, while treating the HepG2 (liver) cells for 1 h with rHSP27 resulted in a 40% reduction in PCSK9 expression (FIG. 15B).

FIG. 16A shows Western blots and a chart (relative densitometry quantification) indicating that treating HepG2 (liver) cells for 6 h with 17 β-estradiol resulted in a 116% increase in LDL-Receptor expression, while treating the HepG2 (liver) cells for 6 h with rHSP27 resulted in a 126% increase in LDL-Receptor expression (FIG. 16B).

Figure 17:
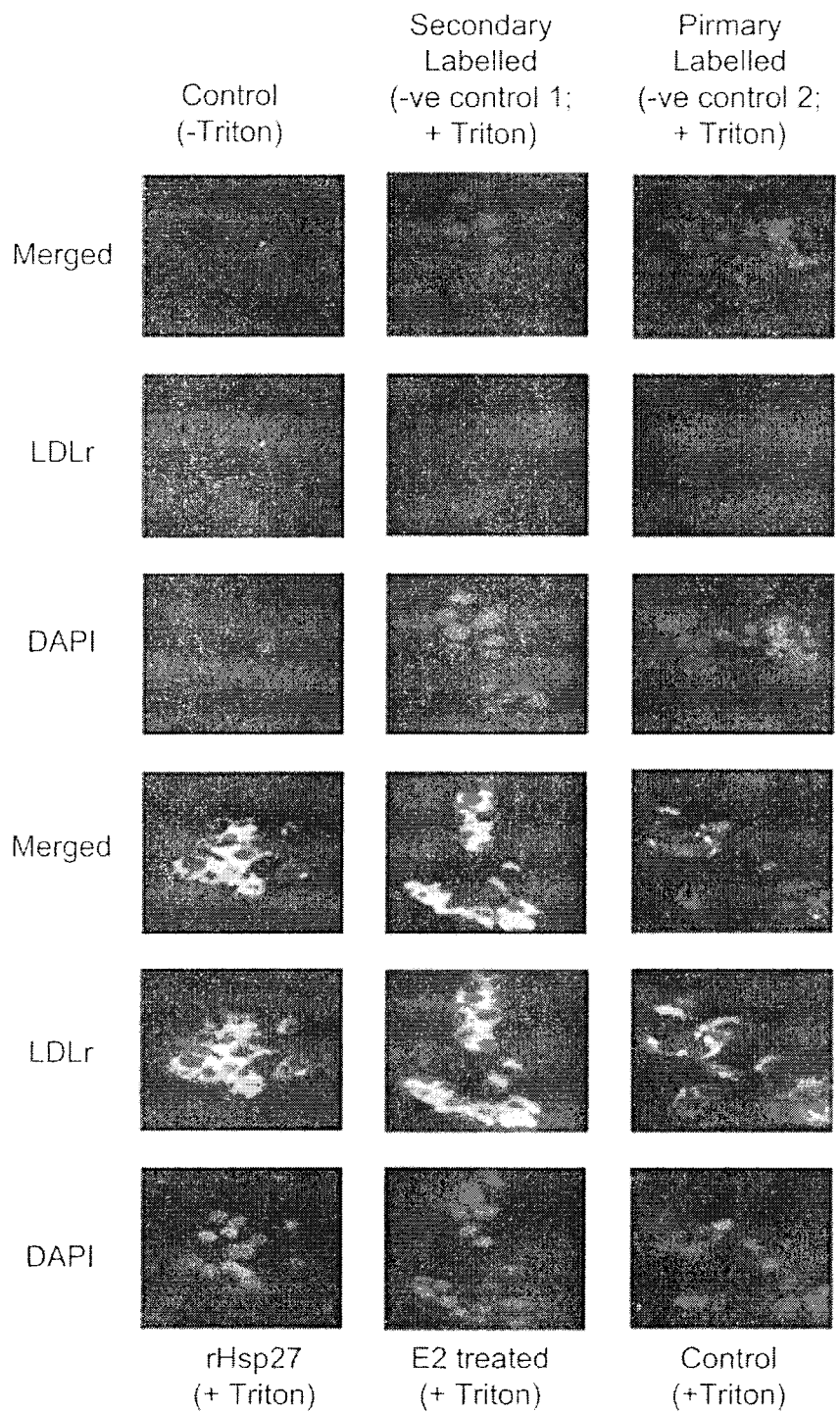
FIG. 17 shows micrographs of HepG2 (liver) cells that were (i) fluorescently immunolabelled for expression of LDL-Receptor (LDL-R) after treatment with either rHSP27 or 17 β-estradiol (E2), or nothing (control), (ii) nuclear stained with DAPI, and (iii) merged images of fluorescently immunolabelled and DAPI-stained cells.

FIG. 17 shows micrographs of HepG2 (liver) cells fluorescently immunolabelled for expression of LDL-Receptor (LDL-R) after treatment with either rHSP27 or 17 β-estradiol (E2), or nothing (control). Both rHSP27 and E2 increased the LDL-R signal. Nuclear staining using DAPI (blue). LDL-Receptor immunolabelling yielded a green fluorescence. The merged images represent a combination of DAPI staining and LDL-R immunolabelling. The right half of the FIG. 17 shows three controls, one for each row: absence of triton treatment (top row), absence of secondary or primary labeling antibodies (middle and bottom rows).

Example 4: Adjuvant Effects on the Efficacy of rHSP27

During the work done on the studies disclosed in Example 1, it was noticed that the concentration of adjuvant in the rHSP27 dosing composition may be augmenting the effects of HSP27 on reducing the expression of PCSK9 proteins. Furthermore, some observations suggested that the HSP27 were additionally stimulating an increase in production of HSP27 auto-antibodies, referred to herein as "anti-HSP27 AAbs", that were detected in the serum samples collected from the test animals. While the roles and importance of HSP27 are known, the clinical significance of anti-Hsp27 AAbs in mammalian circulatory systems is unclear (Wu et al., 2006, Antibodies against heat shock proteins in environmental stresses and diseases: friend or foe? Cell Stress Chaperones 11(1):1-12).

Accordingly, a first study was designed to assess the enhancement effects of Freund's complete adjuvant on the increase in plasma levels of HSP27 and the duration of elevated levels.

Figure 18:
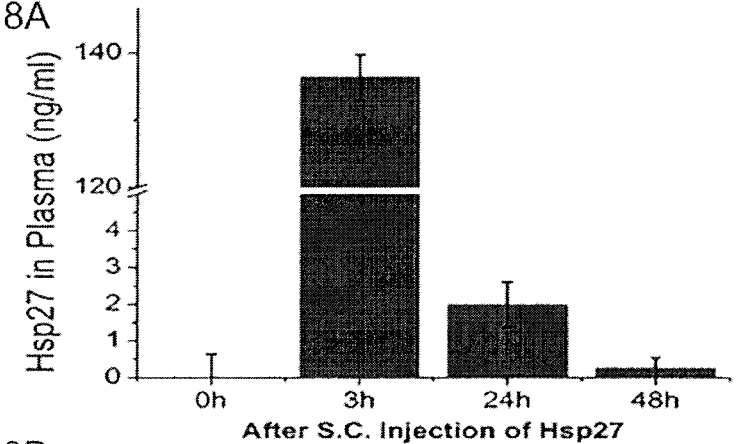
Figure 18:
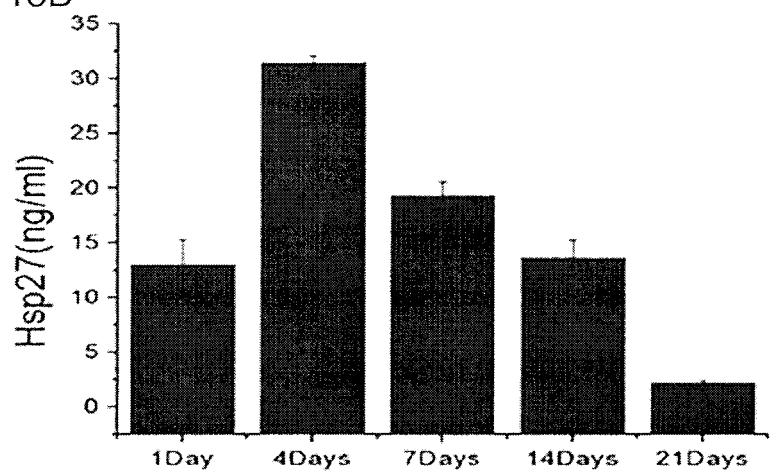
Figure 18:
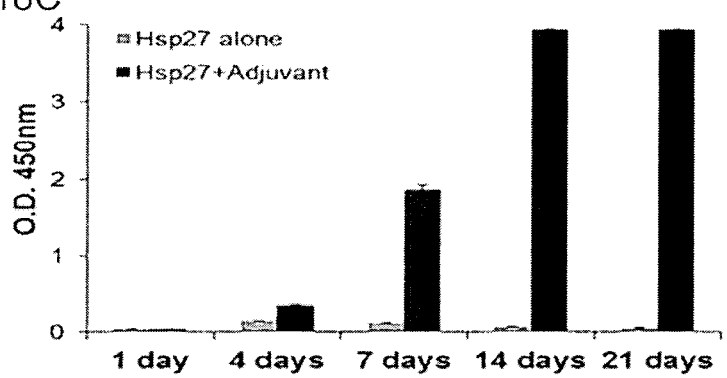

FIG. 18A shows that a solution comprising rHSP27 without adjuvant caused an immediate and significant increase in plasma HSP27 levels, i.e., within 3h, and that the elevated levels dropped considerable within 24 h and 48 h after injection. However, test animals that received an intraperitoneal injection of rHSP27 supplemented with 100 µg/mL of Freund's complete adjuvant had 5×s more HSP27 in their plasma 24 h (FIG. 18B) after injection than did the animals receiving an injection with only rHSP27 (FIG. 18A). The plasma levels of HSP27 AAb more than doubled during the second 24 h after injection with the adjuvant-supplemented rHSP27 solution, and remained elevated for three weeks whereas the HSP27 AAb levels in the animals receiving an injection of rHSP27 only declined to base levels by the second week (FIG. 18C). These data confirm that addition of an adjuvant to an injectable HSP27 immunizing solution significantly elevates the level of HSP27 AAb and maintains the elevated level for three weeks after immunization.

A second study was done to assess the effects of an alum adjuvant on rHSP27 effects on affecting increases in plasma levels of HSP27 AAb and the duration of the elevated levels. The alum adjuvant comprised aluminum hydroxide in the form of ALHYDROGEL® sourced from Invitrogen. All experimental procedures involving laboratory animals were performed with approval from the Animal Care Committee of the University of Calgary. Mice (C57BL10) were purchased from the Jackson Laboratory (Bar Harbor, Me.) and fed a normal chow diet until 12 or 32 weeks of age, wherein they received one-time subcutaneous injection of one of (i) aluminum (50 ul)+rHSP27 (50 ul, 100 µg), (ii) aluminum (25 ul)+rHSP27 (75 ul, 100 µg), (iii) aluminum (50 ul) alone, or (iv) rHSP27 (100 ul, 100 ug) alone. Four weeks later, the mice were euthanized by inhalation of carbon dioxide. Bloods were collected in tubes with K2E(K2EDTA, BD Microtainer) via the saphenous vein at before and after injection weekly, and the right ventricle using 28-gauge needle syringe (insulin syringe) at end experiment. The blood plasmas were separated by centrifugation (10,000 rpm, 10 min). The homemade enzyme-linked immunosorbent assay (ELISA kit) was employed to measure mouse plasma levels of anti-HSP27 antibody.

Figure 19:
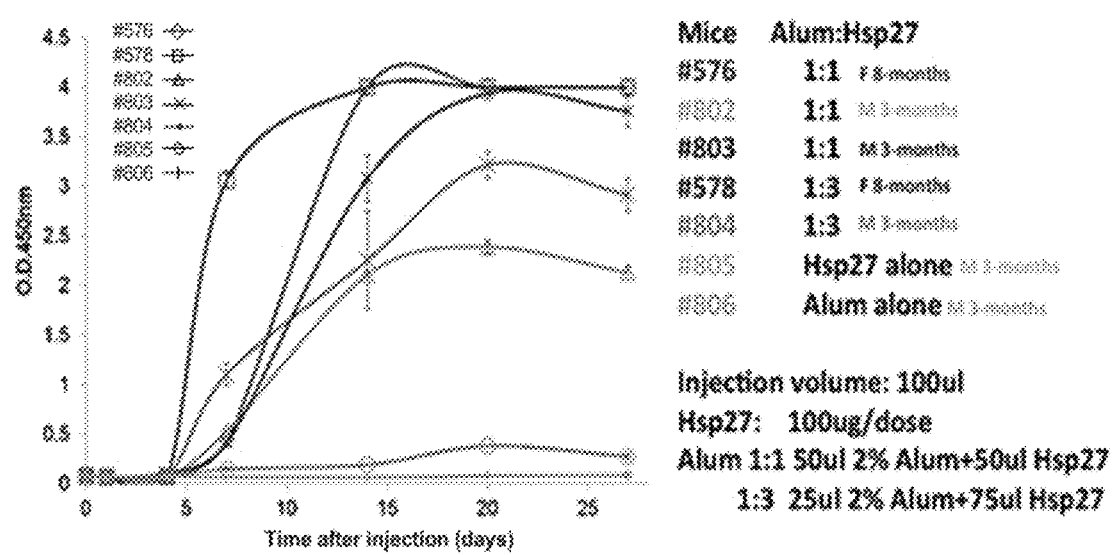
FIG. 19 is a chart showing the effects of alum adjuvant addition to HSP27 treatments on HSP27 AAb evels in apoE$^{-/-}$ mice for 4 weeks after injection.

To assess the efficacy of using alum as an adjuvant that will boost the levels of anti-HSP27 antibodies, a dose response curve was established using varying ratios of alum to recombinant HSP27. A single injection of alum and HSP27 was administered subcutaneously on day zero. The x-axis shows time in days. The y-axis shows the optical density measurement used to assess anti-HSP27 antibodies. Various mice, identified by a number, sex (M,F) and age (in months) were used for these experiments. Control injections included mice #805 and 806, with HSP27 (alone) and Alum (alone); respectively. For the other mice, the ratios of alum to HSP27 are listed (i.e., 1:1 and 1:3). The data shown in FIG. 19 confirm that both ratios of alum to HSP27 resulted in an increase in serum anti-HSP27 antibodies, that persisted over more than 3 weeks, whilst injections of alum alone, or HSP27 alone, did not produce substantial levels of anti-HSP27 antibodies.

Figure 20:
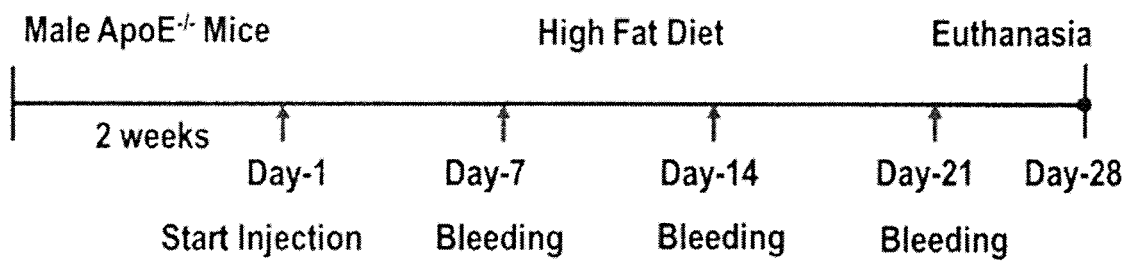
FIG. 20 is a schematic illustration of the experimental protocol for administration of recombinant HSP25 (rHSP25) plus alum adjuvant subcutaneous injection therapy and sampling of three groups of male apoE$^{-/-}$ mice.

Example 5: Effects of Compositions Comprising rHSP27 Plus Adjuvant on Plasma Cholesterol Levels FIG. 20 shows a treatment protocol for three groups of male ApoE$^{-/-}$ mice fed a high-fat diet and receiving one of three treatments. Group I mice received one dose of a composition comprising rHSP25 plus an alum adjuvant. Group II mice received an initial dosage of a composition comprising rHSP25 plus an alum adjuvant followed by weekly injections of rHSP25. Group II mice were the control group and received weekly injections of a composition comprising rHSP27-C1 plus an alum adjuvant. HSP25 is the mouse orthologue of human HSP27. rHSP27-C1 is a truncated form of the rHSP27 protein consisting of the biologically inactive C-terminus, and therefore represents a control treatment. The methods and materials used in this study followed those discussed in Examples 3 and 4, and are further elaborated below.

Immunization of rHSP25/27 in Atherogenic Mice Model

The ApoE$^{-/-}$ with C57BL/6 background and LDLR$^{-/-}$ with C57BL/6 background mice were purchased from the Jackson Laboratory (Bar Harbor, Me.). The HSP25$^{-/-}$ with C57BL/6 background mice were provided by Imperial College London, and were maintained by continuously inbreeding following the method taught by Crowe et al, (2013, Heat shock protein B1-deficient mice display impaired wound healing. PLoS One, Oct15:8(10):e77383). HSP25$^{-/-}$ females were crossed with apoE$^{-/-}$ males to generate apoE$^{+/-}$ HSP25$^{+/-}$ mice, which were crossed again generate apoE$^{-/-}$ HSP25$^{-/-}$ mice. All mice were ear-notch and genotyped. Mice were fed a normal chow diet until 8 weeks of age, wherein they received high-fat diet (1.25% cholesterol, 15.8% fat; Harlan Teklad, Madison, Wis.) for 2 weeks, and then maintained on a high fat diet for 4 weeks while receiving either the rHSP25 (25 ul, 100ug) plus alum (25 ul) adjuvant and from second day rHSP25 (100 ug) treatment twice a day (group I), the rHSP25 (25 ul, 100 ug) plus alum (25 ul) adjuvant treatment weekly (Group II), or the control alum (25 ul) adjuvant plus rHSP27-C1 (75 ul, 100 ug) treatment weekly (group III). After 4 weeks treatment, mice were euthanized by inhalation of carbon dioxide.

Blood Plasmas

The bloods were collected in tubes with K2E (K2EDTA, BD Microtainer) via the saphenous vein at before and after injection weekly, and the right ventricle using 28-gauge needle syringe (insulin syringe) at end experiment. The blood plasmas were separated by centrifugation (10000 rpm, 10 min).

Measurement of Plasma Cholesterol Levels

Total cholesterol levels were determined using an enzymatic assay kit (Wako Pure Chemical Industries, Ltd, Osaka, Japan). Pooled plasma samples were separated by FPLC to obtain lipid sub-fractions. The fasting was taken for 16 hours.

Measurement of Plasma PCSK-9 Levels

The homemade enzyme-linked immunosorbent assay (ELISA kit) was employed to measure mouse plasma levels of PCSK-9.

Evaluation of "En Face" Atherosclerotic Lesion Area

The aorta was dissected from the ascending to the thoracic segments, and after removing the adventitia, pinned and photographed for visualization of lesion burden. Thereafter, the aorta was opened longitudinally, with the primary incision following the lesser curvature of the arch. To obtain a flat preparation for imaging, a second incision was made along the greater curvature of the arch down to the level of the left subclavian artery. Lipid-rich intraluminal lesions were stained with oil red O and photographed. The en face atherosclerotic aortic lesions were analyzed by two independent observers blinded to the treatment status of the mice using Image-Pro software (Media Cybernetics, Silver Spring, Md.). The extent of atherosclerosis was expressed as the percentage of surface area of the entire aorta covered by lesions.

Immunohistochemical Expression of PCSK9 in Liver Tissues

Figure 21:
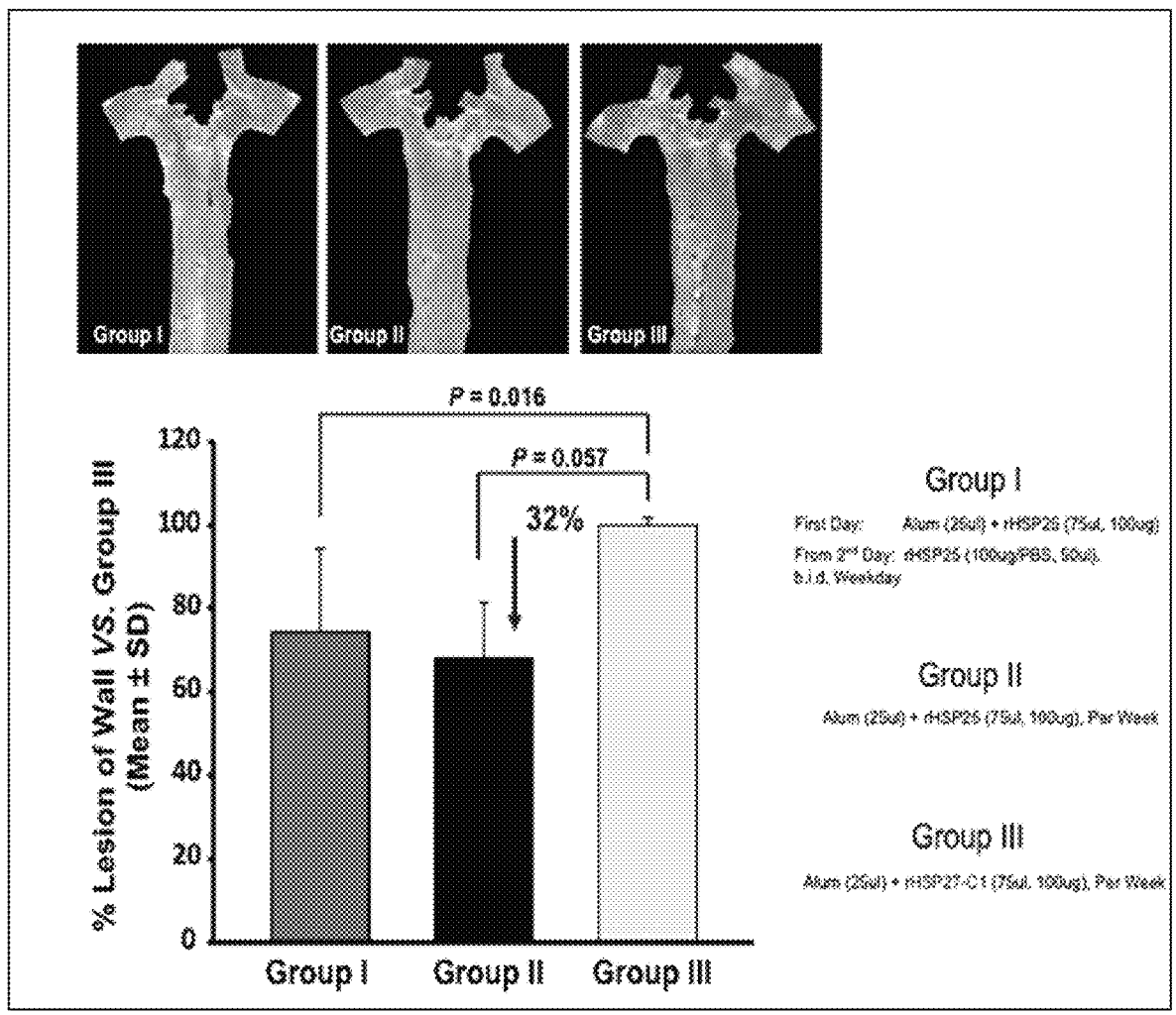
FIG. 21 top panel shows micrographs of mouse aortae from the three groups listed in FIG. 20 (en face projection) with stained with oil red ○ staining from each of the three groups, while the chart shows the % lipid lesions from each of the three groups.

Briefly, the 5-μm paraffin sections of liver tissue were deparaffinaged, rehydrated and blocked with 10% normal horse serum followed by rabbit anti-mouse PCSK9 primary antibody (ab31762, Abcam Inc. Toronto, Canada) diluted in PBS 1:250 at 4° C. overnight. Biotinylated goat anti-rabbit was used as secondary antibody (1:100, Vector Laboratories, Burlingame, Calif., USA). Endogenous peroxidase activity was quenched with 3% $H_2O_2$. Antibody reactivity was detected with an ABC kit (Vector Laboratories, Burlingame, Calif., USA) and visualized with diaminobenzidine (DAB). Sections were counterstained with hematoxylin, cleared, and mounted. Negative controls included incubation with control IgG and secondary antibody alone. The all micrographs were captured with a bright field microscope (Olympus BX53, magnification at ×400), Results The top panel of FIG. 21 shows micrographs of mouse aortae (en face projection) with oil red O staining that highlighted the presence of lipid lesions that were quantified and represented in the bar graph below. Both rHSP25 plus alum adjuvant administered either twice daily (Group I) or once weekly (Group II) had less aortic lipid burden than the control group (Group III) thereby confirming that composition comprising rHSP25 plus alum adjuvant administered by subcutaneous injection therapy attenuated atherogenesis in ApoE$^{-/-}$ mice fed a high fat diet.

Figure 22:
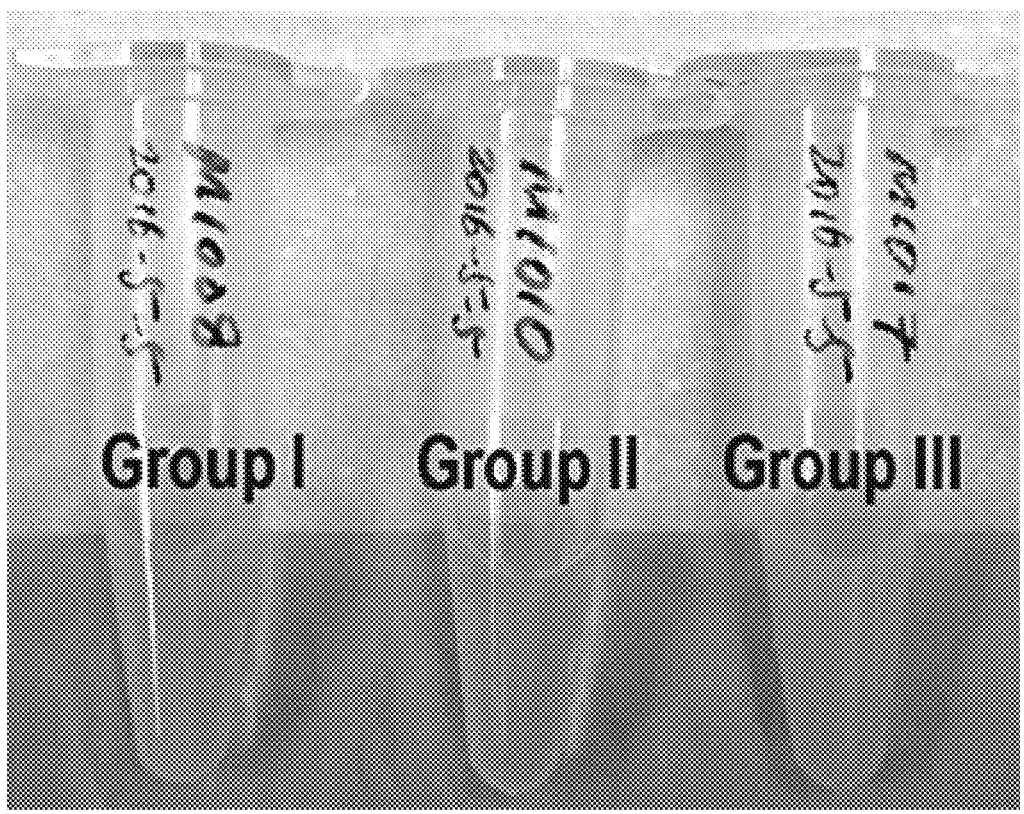
FIG. 22 is a micrograph showing the turbidity of the serum collected from each group of mice from FIG. 21 at time of euthanasia.

FIG. 22 is a micrograph of serum collected at time of euthanasia of mice from the three groups outlined in FIG. 20. The serum from the three groups of mice differ in the degree of turbidity. Turbidity is a reflection of cholesterol content. The control group (III) had the most turbid serum, followed by the twice daily treatment group (I). The least turbid serum was from the active treatment group II that was immunized once weekly with rHSP25 plus the alum adjuvant.

Figure 23:
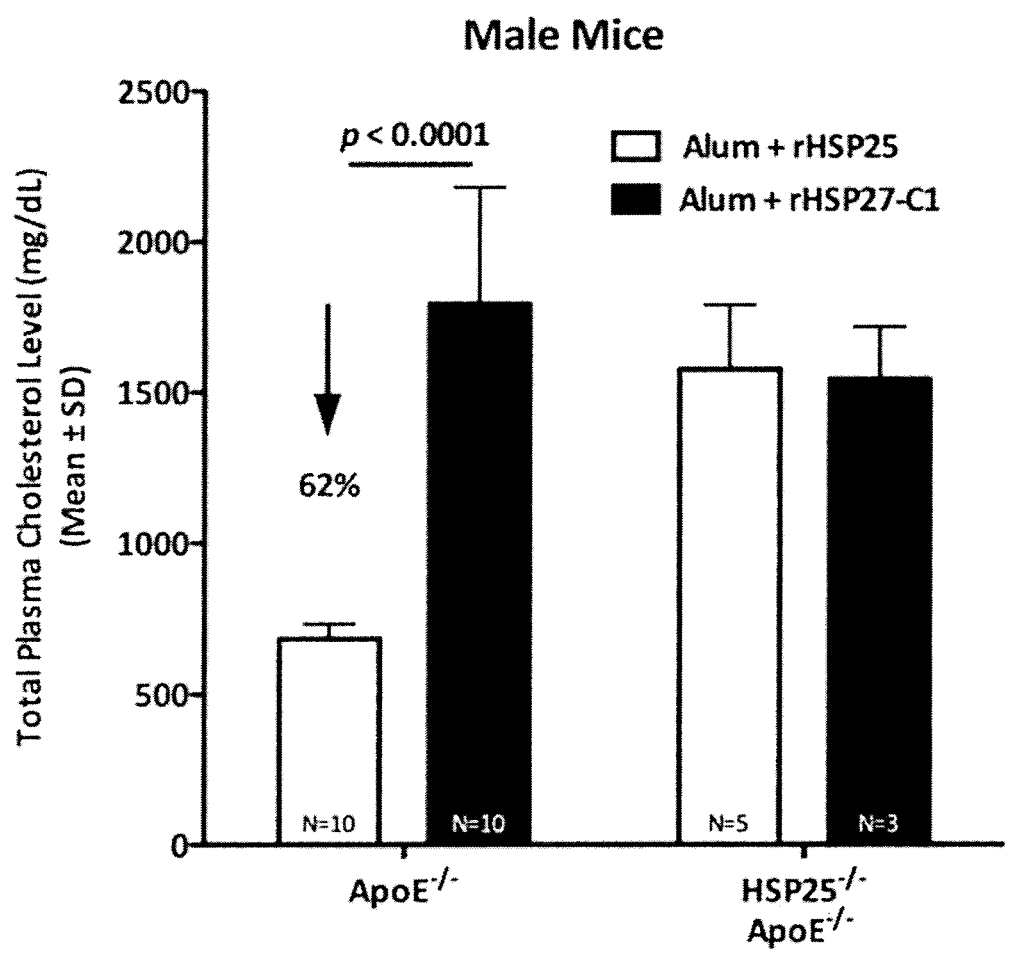
FIG. 23 is a chart showing plasma cholesterol levels in Group II mice injected with rHSP25 plus alum (left white bar) compared to Group III mice injected with rHSP27-C1 control peptide plus alum (left black bar), while mice deficient in HSP25 and ApoE (i.e., double knockout or HSP25$^{-/-}$ apoE$^{-/-}$) did not show a difference in total cholesterol levels in response to treatment with rHSP25 plus alum (right white bar) compared to rHSP27-C1 control (right black bar)

FIG. 23 shows data that indicates male mice injected with rHSP25 plus alum adjuvant once weekly (white bar on the left side) had 63% lower plasma cholesterol levels after 4 weeks of treatment compared to mice injected with rHSP27-C1 control peptide (black bar on the left side). An analogous experiment with mice that were deficient in HSP25 and ApoE (i.e., double knockout or HSP25$^{-/-}$apoE$^{-/-}$) did not show any difference in total cholesterol levels in response to treatment with rHSP25 plus alum (white bar on the right side) compared to rHSP27-C1 control (black bar on the right side).

Figure 24:
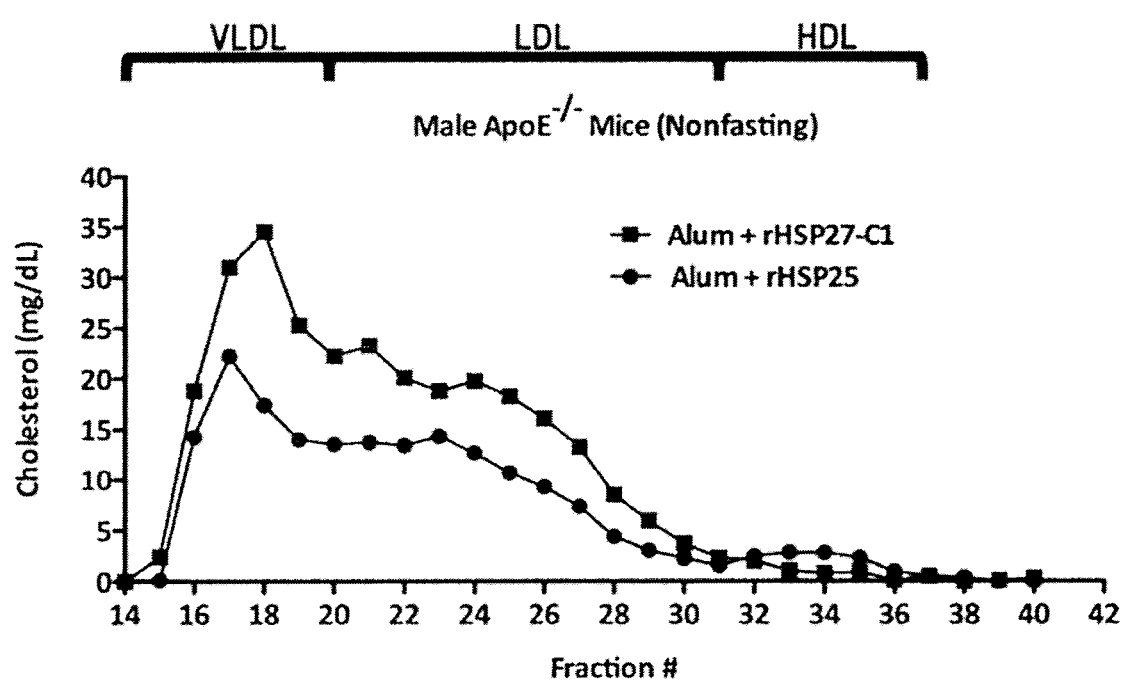
FIG. 24 is a chart showing FPLC data from non-fasting male apoE$^{-/-}$ mice maintained on a high fat diet for 4 weeks and receiving either the alum adjuvant plus rHSP25 treatment or the alum adjuvant plus rHSP27-C1 treatment (control)

FIG. 24 shows FPLC data from non-fasting male apoE$^{-/-}$ mice maintained on a high fat diet for 4 weeks. Treatment with a composition comprising rHSP27 plus an alum adjuvant resulted in lower very-low-density lipoprotein (VLDL) and low-density lipoprotein (LDL) sub-fractions compared to the control treatment comprising rHSP27-C1 plus alum adjuvant.

Figure 25:
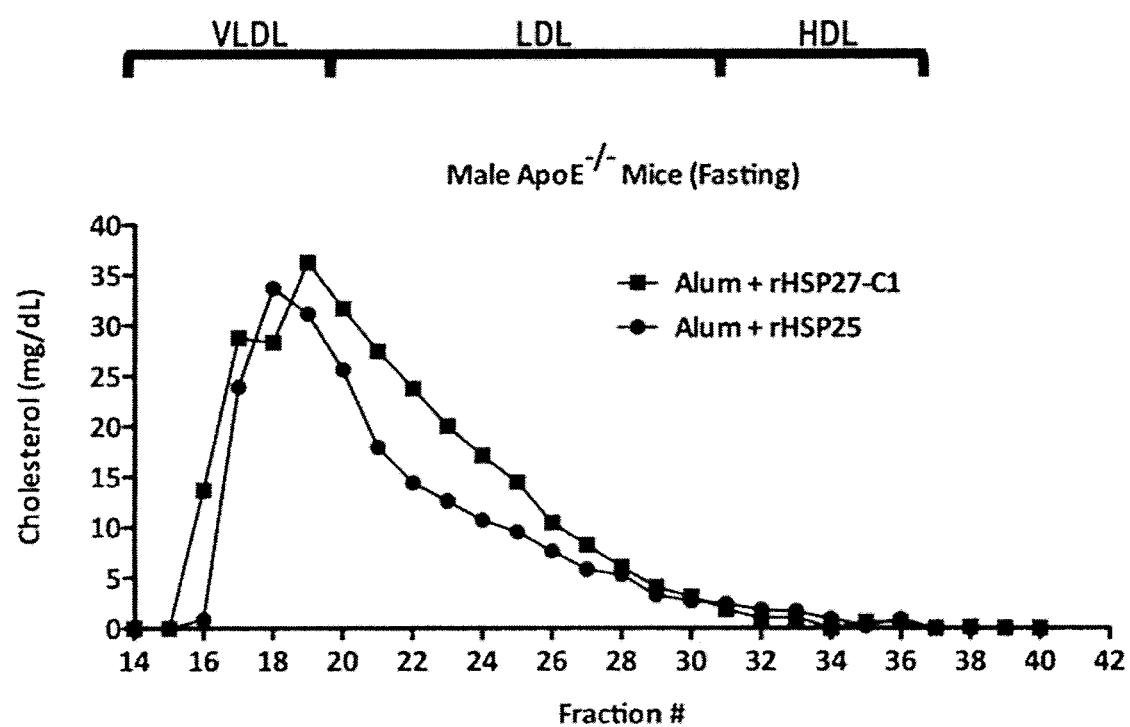
FIG. 25 is a chart showing FPLC data from fasting male apoE$^{-/-}$ mice maintained on a high fat diet for 4 weeks and receiving either the alum adjuvant plus rHSP25 treatment or the alum adjuvant plus rHSP27-C1 treatment (control)

FIG. 25 shows FPLC data from fasting male apoE$^{-/-}$ mice maintained on a high fat diet for 4 weeks. Treatment with a composition comprising rHSP27 plus an alum adjuvant resulted in lower very-low-density lipoprotein (VLDL) and low-density lipoprotein (LDL) sub-fractions compared to the control treatment comprising rHSP27-C1 plus alum adjuvant.

Figure 26:
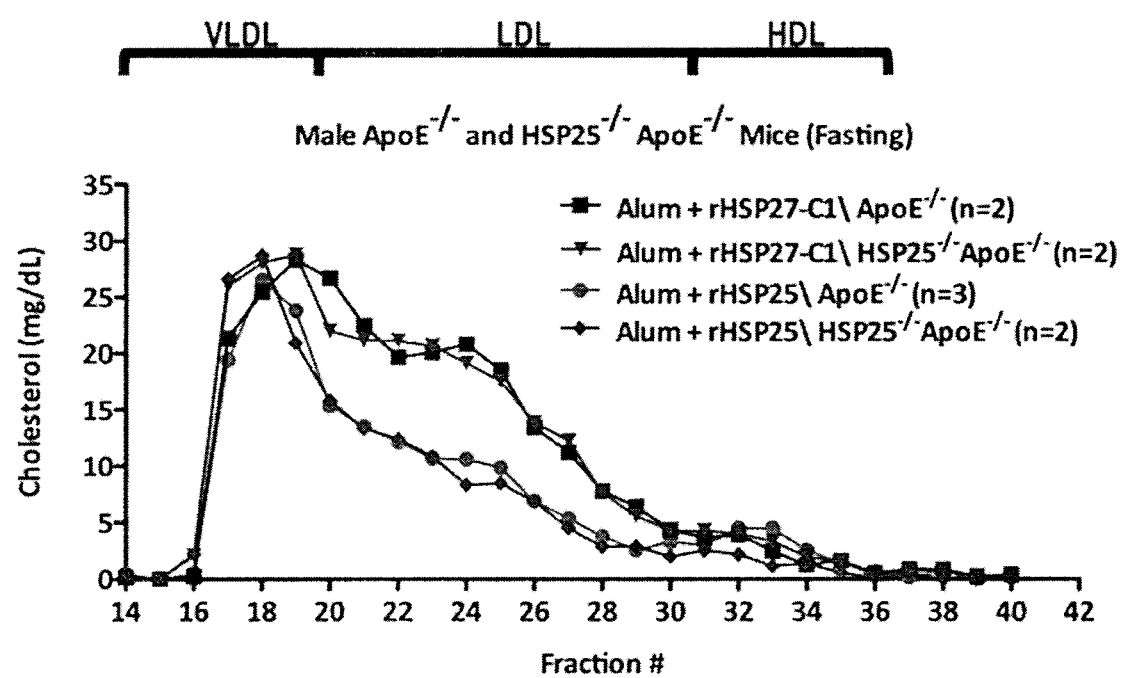
FIG. 26 is a chart showing FPLC data from fasting (i) male apoE$^{-/-}$ and (ii) apoE$^{-/-}$ HSP25$^{-/-}$ mice maintained on a high fat diet for 4 weeks and receiving either the alum adjuvant plus rHSP25 treatment or the alum adjuvant plus rHSP27-C1 treatment (control)

FIG. 26 shows FPLC data from fasting male apoE$^{-/-}$ and apoE$^{-/-}$HSP25$^{-/-}$ mice maintained on a high fat diet for 4 weeks. The LDL cholesterol sub-fraction was lower in in both groups mice treated with a composition comprising rHSP25 plus an alum adjuvant in comparison to the control groups that received a composition comprising rHSP27-C1 plus alum adjuvant.

Figure 27:
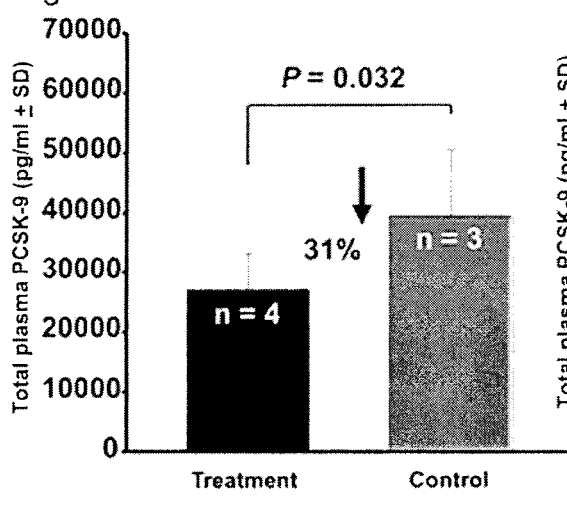
Figure 27:
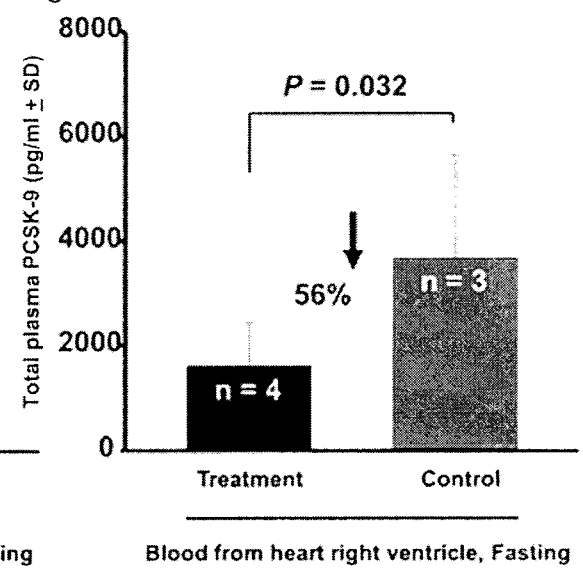

FIG. 27A shows serum PCSK9 levels in male apoE–/– mice in a non-fasting state after completing a 4 week high fat diet, while FIG. 27B shows serum PCSK9 levels in male apoE–/– mice in a fasting state after completing a 4 week high fat die. In both states, treatments with a composition comprising rHSP27 plus an alum adjuvant resulted in lower PCSK9 levels compared to control treatments comprising rHSP27-C1 plus an alum adjuvant. Of note, the differences in PCSK9 levels between the non-fasting and fasting state are approximately 10-fold.

Figure 28:
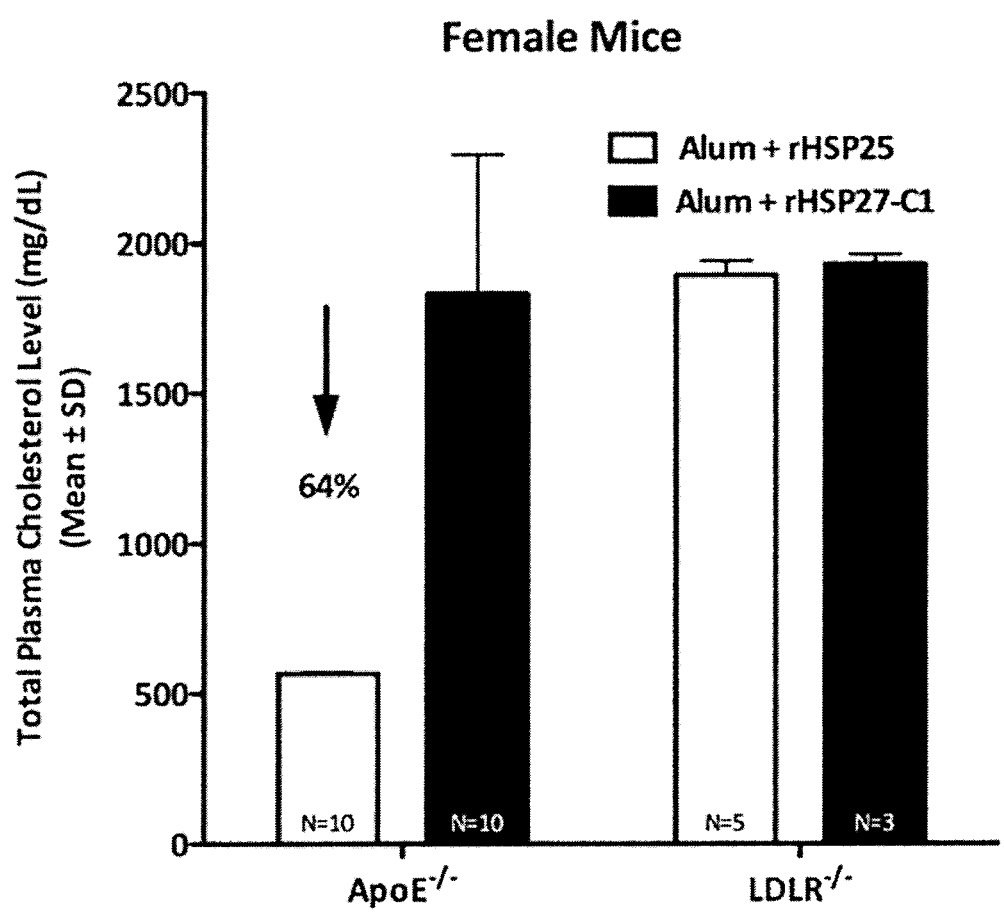
FIG. 28 is a chart wherein (i) the white bar on the left side compares the effect of weekly injections of female mice with the rHSP25 plus alum adjuvant once weekly to female mice receiving weekly injections of the alum adjuvant plus the rHSP27-C1 control peptide (black bar) on total plasma cholesterol levels, and (ii) the white bar on the right side shows the total plasma cholesterol response of female mice that are deficient in the LDL receptor (LDL-R$^{-/-}$) to the rHSP25 plus alum adjuvant in comparison to females mice receiving the control alum adjuvant plus rHSP27-C1 treatment.

FIG. 28 shows data that indicates that female mice injected with a composition comprising rHSP25 plus an alum adjuvant once weekly (white bar on the left side) had 64% lower plasma cholesterol levels after 4 weeks of treatment compared to mice injected with a control treatment comprising rHSP27-C1 plus an alum adjuvant (black bar on the left side). An analogous experiment involving female mice that are deficient in the LDL receptor (LDL-R$^{-/-}$) did not show a difference in total cholesterol levels in response to treatment with the composition comprising rHSP25 plus alum adjuvant (white bar on the right side) compared to rHSP27-C1 control treatment (black bar on the right side). These data demonstrate the requirement for LDL-receptors in order to respond to rHSP25 therapies thereby suggesting that the mechanism by which HSP25 reduces cholesterol levels may involve PCSK9, which in turn interferes with normal recycling of the LDL-R.

Figure 29:
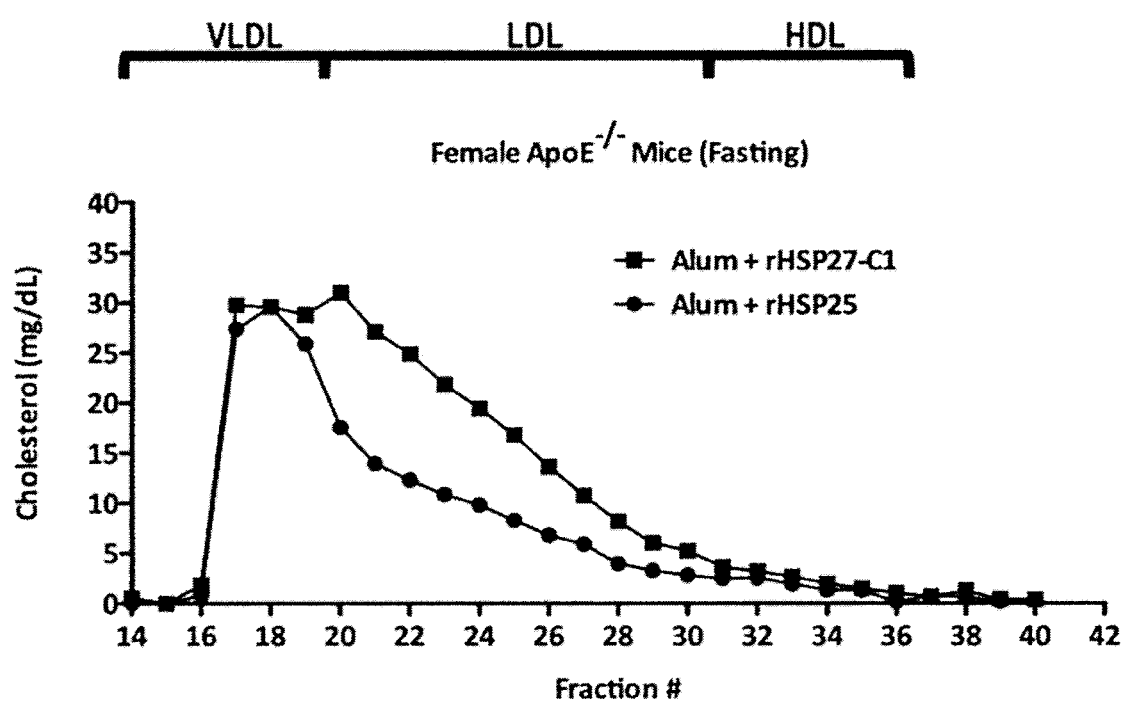
FIG. 29 is a chart showing FPLC data from fasting female apoE$^{-/-}$ mice maintained on a high fat diet for 4 weeks while receiving either the rHSP25 plus alum adjuvant treatment weekly, or the control alum adjuvant plus rHSP27-C1 treatment weekly.

FIG. 29 shows FPLC data from fasting female apoE$^{-/-}$ mice maintained on a high fat diet for 4 weeks. Treatment with a composition comprising rHSP27 alum adjuvant resulted in reduced levels of the low density lipoprotein (LDL) sub-fraction compared to the control treatment with a composition comprising rHSP27-C1 and an alum adjuvant.

Figure 30:
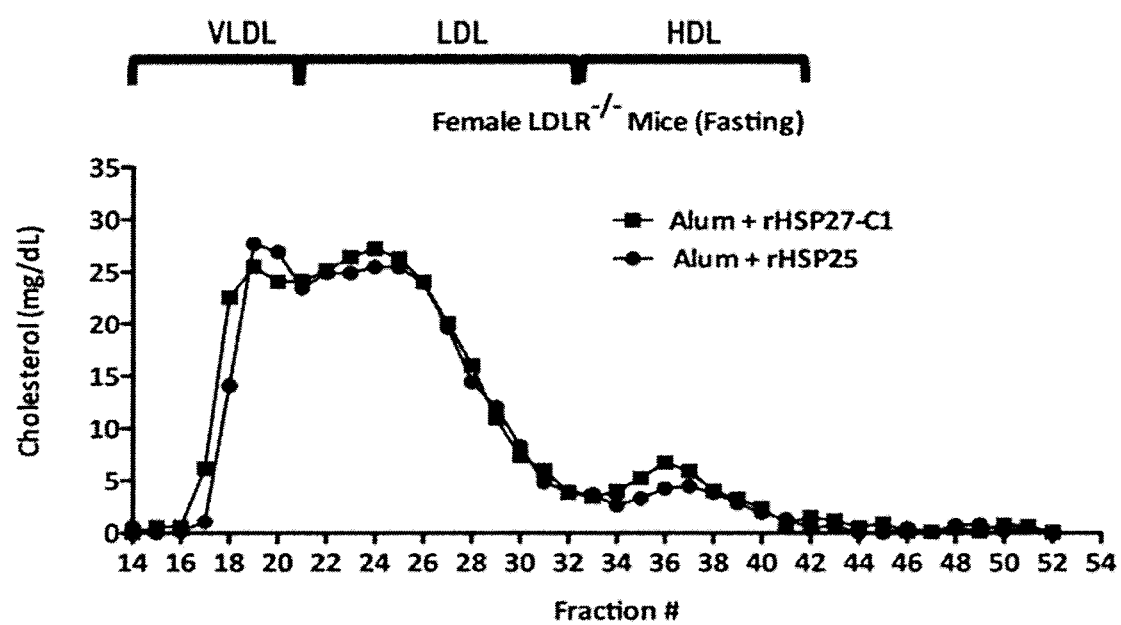
FIG. 30 is a chart showing FPLC data from fasting female LDL-R$^{-/-}$ mice maintained on a high fat diet for 4 weeks while receiving either the rHSP25 plus alum adjuvant treatment weekly, or the control alum adjuvant plus rHSP27-C1 treatment weekly.

FIG. 30 shows FPLC data from fasting female LDL-R$^{-/-}$ mice maintained on a high fat diet for 4 weeks. There are no the lipoprotein cholesterol sub-fractions in response to treatment with a composition comprising rHSP25 plus alum adjuvant compared to rHSP27-C1 control treatment. These data demonstrate the requirement for LDL-receptors in order to respond to rHSP25 therapies thereby suggesting that the mechanism by which HSP25 reduces cholesterol levels may involve PCSK9, which in turn interferes with normal recycling of the LDL-R.

Figure 31:
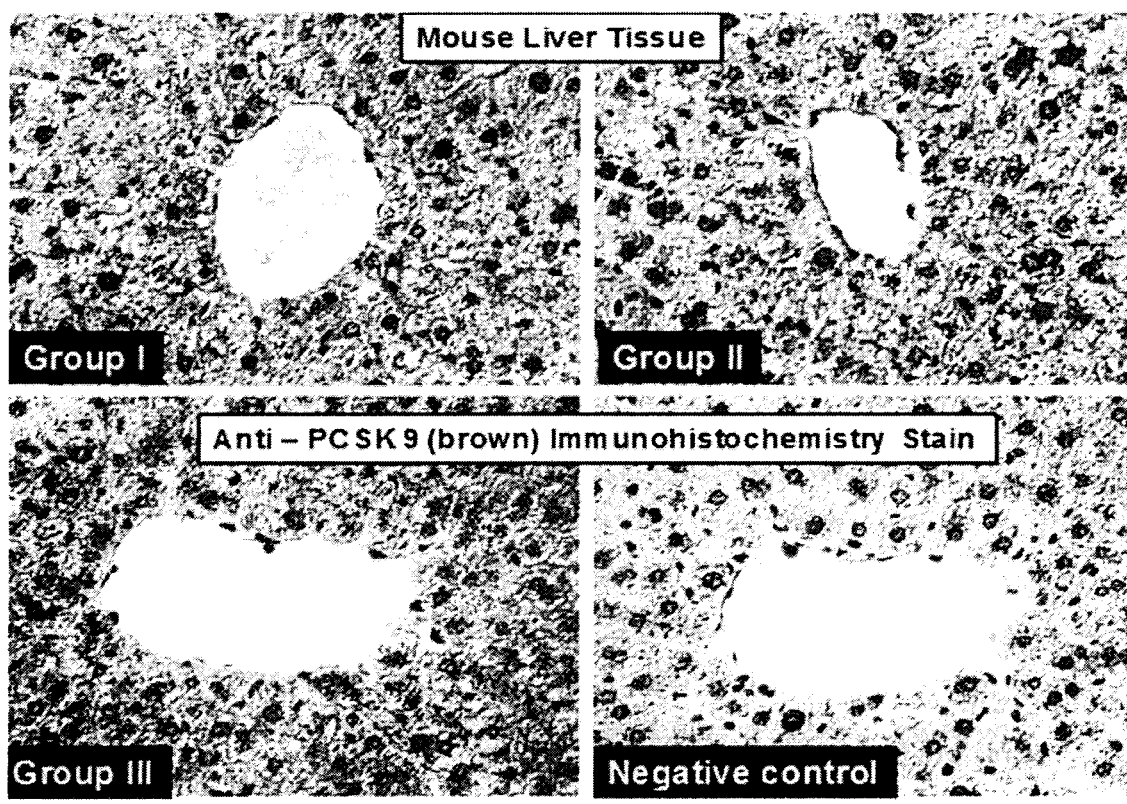
FIG. 31 shows micrographs of liver tissue from apoE$^{-/-}$ mice (treated according to the schematic process listed in FIG. 22) that were immunolabelled with an anti-PCSK9 antibody to yield a brown color reaction.

FIG. 31 shows micrographs of liver tissue from apoE-/- mice (treated according to the schematic found in FIG. 20) that are immunolabelled with an anti-PCSK9 antibody to yield a brown color reaction. The mice receiving treatment with the composition comprising rHSP25 plus alum adjuvant (Group II) had the lowest levels of PCSK9 immunolabelling, followed by mice that received only one dosage of the composition comprising rHSP25 plus alum adjuvant (Group I). The control treatment (Group III) shows abundant immunolabelling for PCSK9. For comparison purposes, omission of the primary antibody was used as a negative control for the immunolabelling.

Example 6: Effects of Compositions Comprising rHSP27 Plus Adjuvant on Plasma Cholesterol Levels Pre-Menopausal and Post-Menopausal Women Study Population for Human Serum Specimens As part of an NIH sponsored study (Project #5P20MD002314-08; Sub-Project ID: 6374) looking for biochemical markers reflective of an acute coronary syndrome, 242 patients with established or suspected coronary artery disease (CAD) were enrolled in a 5-year follow-up study that involved the collection of blood samples at various University of South Alabama-affiliated medical clinics. This population was medically underserviced and racially mixed and consisted of approximately 27% African-Americans. CAD patients were enrolled if they satisfied any of the following inclusion criteria: typical symptoms of angina pectoris lasting>20 minutes at rest, ECG changes during angina symptoms, hypertension, a diagnosis of an acute coronary syndrome or a history of coronary revascularization. Patients were excluded if they suffered from renal impairment, autoimmune or rheumatic heart disease—all factors known to alter levels of inflammatory biomarkers including heat shock proteins. A control population (HC, n=92) lacking any of the inclusion or exclusion criteria was simultaneously recruited. All CAD patients and HC subjects enrolled in this study were followed for two years or more and were excluded from the current biomarker study if their course was unstable and/or had a subsequent cardiovascular event during the follow-up period. Blood samples were drawn at baseline and at every 6 months after their diagnosis of CAD. A total of 79 CAD and 79 HC subjects were matched for age and sex using SAS software (SAS Institute, Calgary, AB), and constituted the comparison groups. For the final cohort analysis African Americans made up 15% of the control group and 37% of the CAD group (p=0.002). More patients with CAD compared to HC had a history of cigarette smoking, hypertension, dyslipidemia (treated), diabetes mellitus or an elevated BMI. Lipid levels were lower in CAD patients than HC because of frequent use of statin therapy. The Framingham Risk Scores for the HC vs. the CAD patients were 8.4+5.2 vs. 15.3+10 (p=0.004).

HSP27 Autoantibody ELISA

Serum HSP27 autoantibody levels were measured using a Enzyme Linked Immunosorbent Assay (ELISA) developed in our laboratory. A 113-amino acid long HSP27 peptide fragment was coated onto NUNC maxisorp plates at 100 ng/well. The wells were blocked with 1% BSA, washed 2× in PBS-T, and diluted sera (1:2000) was added, followed by 2 washes in PBS-T. The detection antibody for this assay was an anti-Human-HRP (Jackson lmmunoresearch, West Grove, Pa.) used at a dilution of 1:5000. To establish an internal standard for the measurement of HSP27 autoantibodies, serum from control subjects diluted 2000 times in 1% BSA/PBST was defined as 50 units.

Results

Figure 32:
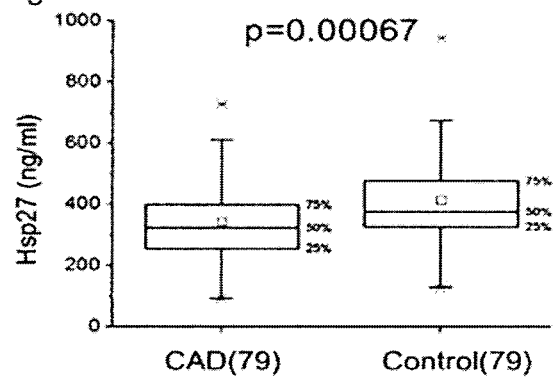
FIG. 32A-FIG. 32D are charts showing age-matched and sex-matched comparisons of human serum HSP27 and anti-HSP27 autoantibody (AAb) levels stratified according to the presence of Coronary Artery Disease (CAD) vs. Healthy Controls (HC) for females and males.
Figure 32:
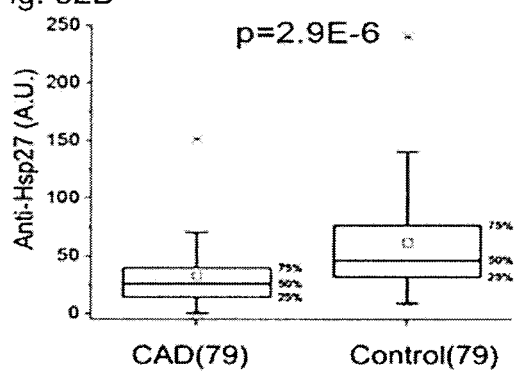
Figure 32:
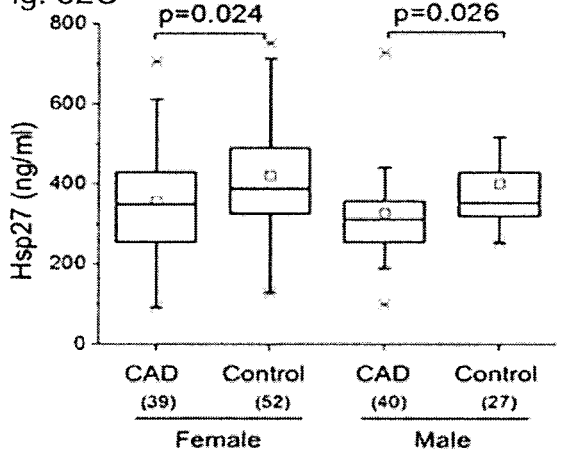
Figure 32:
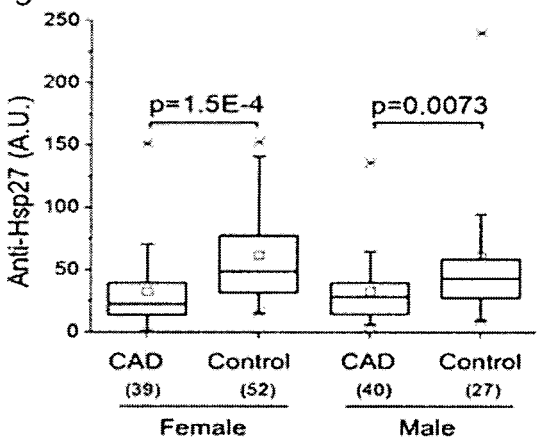
Figure 33A:
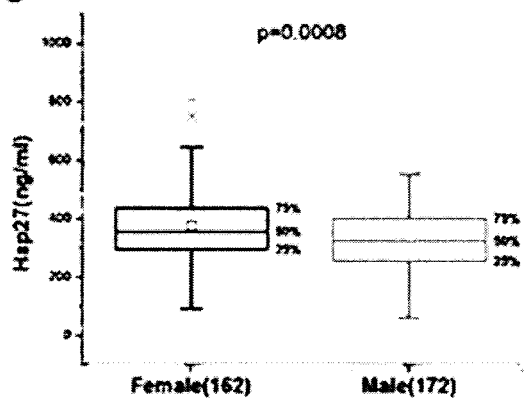
Figure 33B:
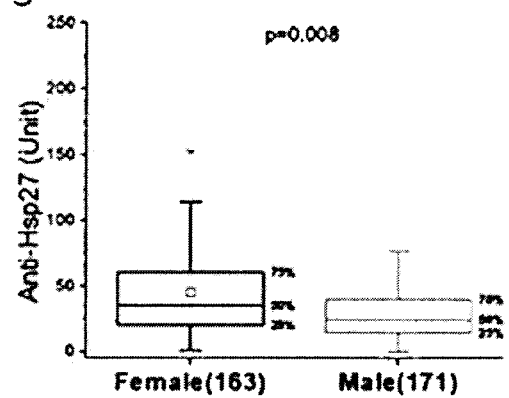
Figure 33C:
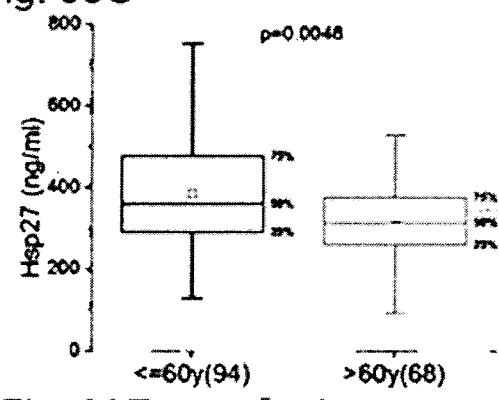
Figure 33D:
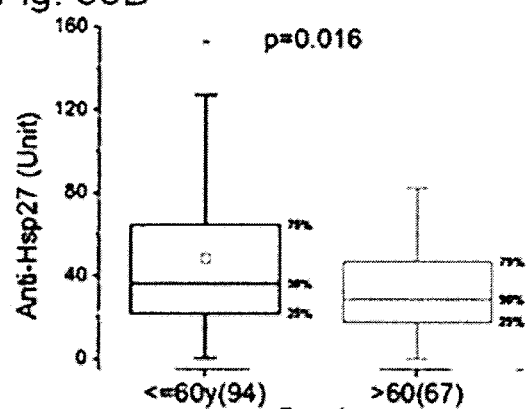
Figure 33E:
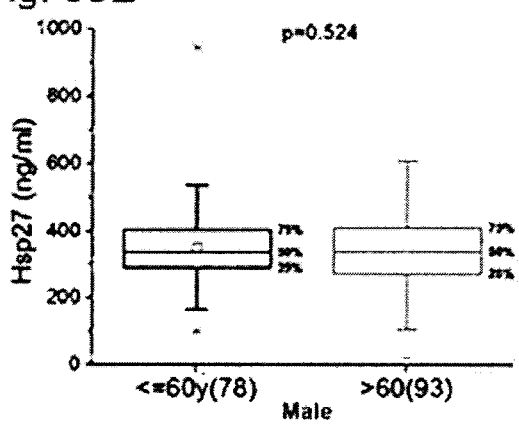
Figure 33F:
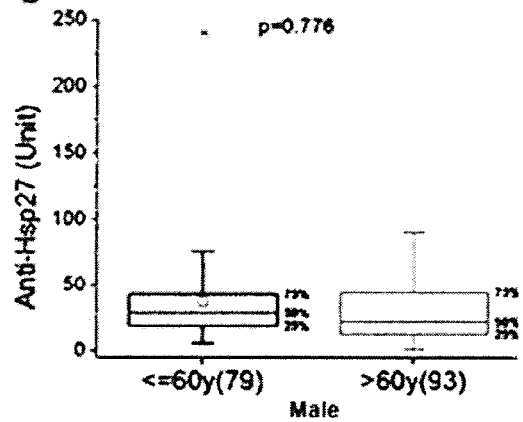
Figure 34:
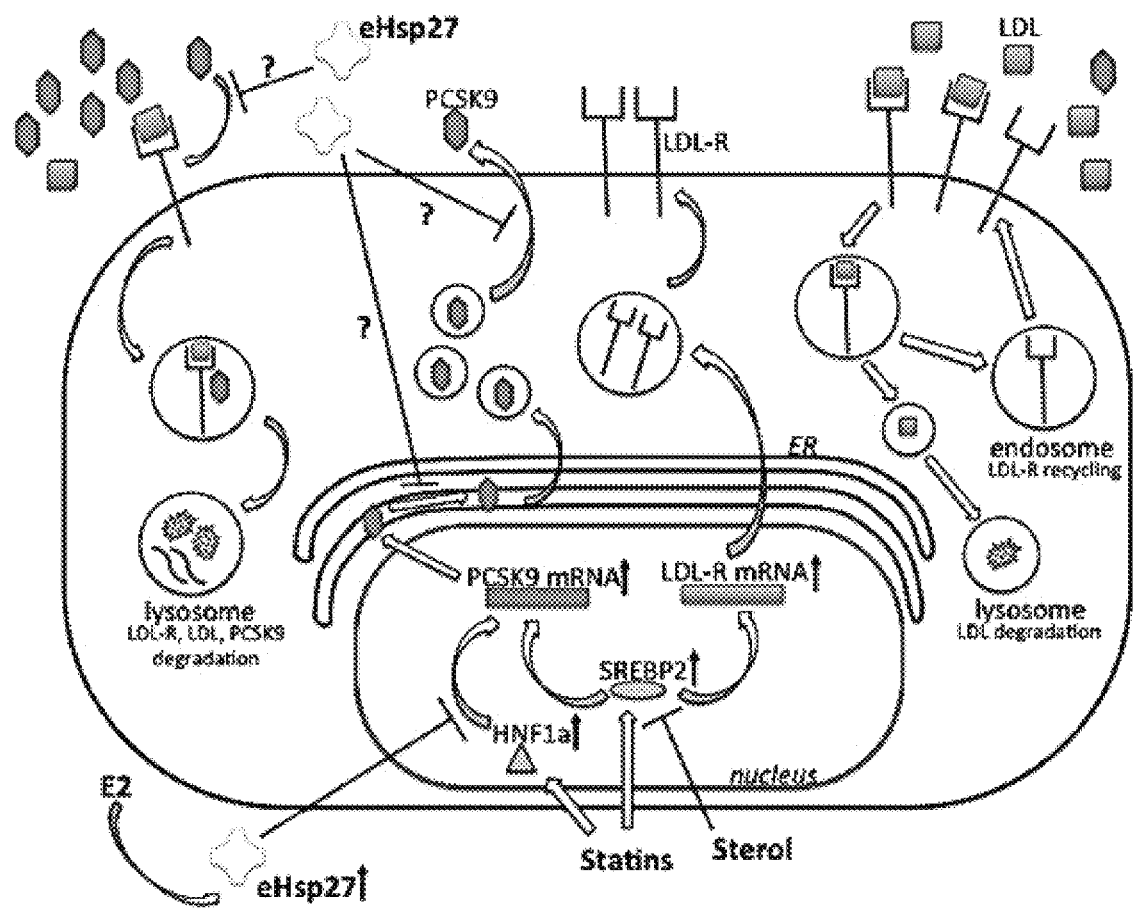
FIG. 34 is a schematic illustration of PCSK-9 and LDL-R traffic within liver cells and shows how extracellular HSP27 (eHSP27) may play an important role in reducing the expression or function of intracellular and/or extracellular PCSK9.

Serum samples were collected from a cohort of over 252 CAD patients and 92 HC subjects. Subjects were matched for age and sex resulting in subgroups of 79HC and 79CAD patients that could be compared. CAD patients had lower HSP27 (323.8 vs. 377.4 ng/ml; p=0.00067) and anti-HSP27 levels (25.8 vs. 46.3 units; p=2.9E-6) compared to HC (FIG. 32A, FIG. 32B respectively). Female CAD patients had lower HSP27 and AAbs compared HC (350.3 vs. 387.9 ng/ml, p=0.024 and 22.3 vs. 49.6 units, p=0.00015; respectively) (FIG. 32C). Male CAD patients had lower HSP27 and AAbs compared to HC (314.0 vs. 352.5 ng/ml, p=0.026 and 28.9 vs. 43.0 units, p=0.0073; respectively) (FIG. 32D). (n) indicates number of patients. Upper and lower limits of box plots demarcate the $75^{th}$ and $25^{th}$ percentiles, respectively. Median and mean are represented by a horizontal line and square, respectively. HSP27 serum levels were measured using a novel mass spectrometry (MS) based assay that separates HSP27 from AAbs. Autoantibodies were measured as arbitrary units (A.U.) using an internal ELISA standard.

Example 7: PCSK-9 and LDL-R Traffic within Liver Cells and the Effects of Extracellular HSP27 (eHSP27) on the Expression and/or Function on PCSK9

Extracellular HSP27 (eHSP27) may have several important roles in reducing the expression and/or function of intracellular and/or extracellular PCSK9. First, the expression of HSP27, as well as its release from cells, is in part due to the influence of estrogens. While not shown here, loss of ovarian function with menopause results in a marked reduction in estrogen serum levels. Accordingly, this diminution in estrogen levels may have a negative influence on the expression and release of HSP27 into the extracellular space. eHSP27 is capable of signaling from the "outside-in" via membrane receptors (e.g., TLR4). As well, eHSP27 may gain access into the cell via transfer mechanisms.

The intracellular actions of HSP27 are several fold and include:
1. Blocking the expression of HNF1a, a transcriptional factor for PCSK9,
2. Inhibiting the release of PCSK9 from cells,
3. Interfering with the PCSK9-LDL Receptor interaction, either by directly altering extracellular PCSK9 and/or the LDL receptor.

The net result of the action of HSP27 is the diminution of PCSK9 levels and/or its effects on the LDL receptor, resulting in an improvement in extracellular cholesterol levels.

SUMMARY

It is within the scope of the present disclosure for the exemplary compositions to additionally comprise sterile diluents such as water for injection, saline solution, fixed oils, polyethylene glycols, glycerine, propylene glycol or other synthetic solvents. Parenteral formulations may also include antibacterial agents such as exemplified by benzyl alcohol, methyl parabens and the like, antioxidants such as exemplified by ascorbic acid, sodium bisulfite and the like, and chelating agents exemplified by EDTA. Buffers such as exemplified by acetate buffers, citrate buffers, phosphate buffers and the like, may also be added. Agents for the adjustment of tonicity such as exemplified by sodium chloride and dextrose may also be added. The parenteral compositions may be dispensed into and contained in ampules, disposable syringes or multiple dose vials made of glass or plastic.

The present disclosure also relates to the use of the exemplary compositions to reduce serum cholesterol levels in mammalian subjects whereby the exemplary compositions cause increases in the subjects' serum levels of HSP27 and/or anti-HSP27 AAbs.

This disclosure also relates to methods for reducing serum cholesterol levels in a mammalian subject by administration of one or therapeutic doses of a composition comprising HSP27 or a mixture of HSP27 and anti-HSP27 AAbs.

This disclosure additionally relates to a method for separating out and quantifying HSP27, anti-HSP27 AAbs, PCSK9, and other proteins and peptides from a serum sample.

---

The invention claimed is:

1. A human pharmaceutical composition the composition comprising:
   a HSP27 protein that shares at least 90% sequence identity with the amino acid sequence set forth in SEQ.ID NO: 4 wherein the concentration of said HSP27 protein, is in the range of 25 µg/mL to 250 µg/mL; and
   an adjuvant wherein the concentration of said adjuvant is in the range of 25 µg/mL to 250 µg/mL;
   together with a pharmaceutically acceptable diluent or carrier.

2. A pharmaceutical composition according to claim 1, wherein the HSP27 protein is a recombinant HSP27 peptide.

3. A pharmaceutical composition according to claim 2, wherein the recombinant HSP27 protein consists of the amino acid sequence set forth in SEQ.ID NO: 4.

4. A pharmaceutical composition according to claim 1, additionally comprising an anti-HSP27 antibody.

5. A pharmaceutical composition according to claim 1, wherein the adjuvant is an aluminum hydroxide adjuvant.

6. A pharmaceutical composition according to claim 1, wherein the ratio of the HSP27 protein, to adjuvant is in the range of 1:1 (v/v) to 1:3 (v/v).

7. A pharmaceutical composition according to claim 1, wherein the composition is administrable by injection.

8. A pharmaceutical composition according to claim 1, wherein the composition is administrable by oral delivery.

9. A pharmaceutical composition according to claim 8, wherein the composition is one of a tablet or a capsule or a liquid.

* * * * *